US009279013B2

(12) United States Patent
Walker et al.

(10) Patent No.: US 9,279,013 B2
(45) Date of Patent: Mar. 8, 2016

(54) FGF-21 MUTANTS COMPRISING POLYETHYLENE GLYCOL AND USES THEREOF

(75) Inventors: Kenneth W. Walker, Newbury Park, CA (US); Colin V. Gegg, Jr., Newbury Park, CA (US); Randy I. Hecht, Thousand Oaks, CA (US); Edward J. Belouski, Camarillo, CA (US); Yue-Sheng Li, Thousand Oaks, CA (US); Mark L. Michaels, Encino, CA (US); Jing Xu, Thousand Oaks, CA (US); Murielle M. Ellison, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/123,205

(22) PCT Filed: Oct. 8, 2009

(86) PCT No.: PCT/US2009/060045
§ 371 (c)(1),
(2), (4) Date: Apr. 7, 2011

(87) PCT Pub. No.: WO2010/042747
PCT Pub. Date: Apr. 15, 2010

(65) Prior Publication Data
US 2011/0195895 A1 Aug. 11, 2011

Related U.S. Application Data

(60) Provisional application No. 61/195,761, filed on Oct. 10, 2008.

(51) Int. Cl.
A61K 38/18 (2006.01)
C07K 14/50 (2006.01)
A61K 38/00 (2006.01)

(52) U.S. Cl.
CPC C07K 14/50 (2013.01); A61K 38/00 (2013.01)

(58) Field of Classification Search
None
See application file for complete search history.

(56) References Cited

U.S. PATENT DOCUMENTS

| 3,773,919 | A | 11/1973 | Boswell et al. |
|---|---|---|---|
| 4,179,337 | A | 12/1979 | Davis et al. |
| 4,301,144 | A | 11/1981 | Iwashita et al. |
| 4,376,110 | A | 3/1983 | David et al. |
| 4,496,689 | A | 1/1985 | Mitra |
| 4,619,794 | A | 10/1986 | Hauser |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,816,567 | A | 3/1989 | Cabilly et al. |
| 4,892,538 | A | 1/1990 | Aebischer et al. |
| 4,945,050 | A | 7/1990 | Sanford et al. |
| 4,970,154 | A | 11/1990 | Chang |
| 5,011,472 | A | 4/1991 | Aebischer et al. |
| 5,106,627 | A | 4/1992 | Aebischer et al. |
| 5,217,889 | A | 6/1993 | Roninson et al. |
| 5,229,501 | A | 7/1993 | Keifer |
| 5,234,784 | A | 8/1993 | Aslam et al. |
| 5,252,714 | A | 10/1993 | Harris et al. |
| 5,272,071 | A | 12/1993 | Chappel |
| 5,288,855 | A | 2/1994 | Bergonzoni |
| 5,364,791 | A | 11/1994 | Vegeto et al. |
| 5,489,743 | A | 2/1996 | Robinson et al. |
| 5,545,807 | A | 8/1996 | Surani et al. |
| 5,557,032 | A | 9/1996 | Mak |
| 5,585,089 | A | 12/1996 | Queen et al. |
| 5,589,362 | A | 12/1996 | Bujard et al. |
| 5,593,875 | A | 1/1997 | Wurm et al. |
| 5,635,399 | A | 6/1997 | Kriegler et al. |
| 5,650,298 | A | 7/1997 | Bujard et al. |
| 5,654,168 | A | 8/1997 | Bujard et al. |
| 5,670,323 | A | 9/1997 | Nova |
| 5,672,510 | A | 9/1997 | Eglitis et al. |
| 5,676,954 | A | 10/1997 | Brigham |
| 5,679,559 | A | 10/1997 | Kim et al. |
| 5,693,762 | A | 12/1997 | Queen et al. |
| 5,707,632 | A | 1/1998 | Williams |
| 5,767,250 | A | 6/1998 | Spaete |
| 5,811,234 | A | 9/1998 | Roninson et al. |
| 6,133,426 | A | 10/2000 | Gonzalez et al. |
| 6,150,098 | A | 11/2000 | Zhang |
| 6,214,795 | B1 | 4/2001 | Benjamin |
| 6,255,454 | B1 | 7/2001 | Keifer |
| 6,344,546 | B1 | 2/2002 | Dionne et al. |

(Continued)

FOREIGN PATENT DOCUMENTS

AU 567572 B2 11/1987
EP 36676 B2 9/1981

(Continued)

OTHER PUBLICATIONS

[The] ADHR consortium (2000), "Autosomal dominant hypophosphataemic rickets is associated with mutations in FGF23." Nature Genetics 26: 345-348.
Arner et ai. (2004) "FGF21 attenuates lipolysis in human adipocytes—A possible link to improved insulin sensitivity" FEBS Letters 582: 1725-1730.
Artuc et al, (1999). "Mast cells and their mediators in cutaneous wound heating—active participants or innocent bystanders?" Exp. Dermatol. 8: 1-16.
Ausubel, et al., Current Protocols in Molecular Biology (Ausubel et al., eds., Green Publishers Inc. and Wiley and Sons 1994).
Bayer et al. (1990). "Protein biotinlyation" Meth. Enz. 184: 136-63.
Beck and Podolsky (1999), "Growth factum in inflammatory bowel disease," Inflamm, Bowel Dis. 5: 44-60.
Bishop (1996), "Chromosomal insertion of foreign DNA" Reprod. Nutr. Dev. 36(6). 607-19.

(Continued)

Primary Examiner — Christine J Saoud

(57) ABSTRACT

The invention provides nucleic acid molecules encoding FGF21 mutant polypeptides, FGF21 mutant polypeptides comprising extended in vivos half-lives, pharmaceutical compositions comprising FGF21 mutant polypeptides having extended in vivos half lives, and methods for treating metabolic disorders using such nucleic acids, polypeptides, or pharmaceutical compositions.

53 Claims, 25 Drawing Sheets

(56) References Cited

U.S. PATENT DOCUMENTS

| | | |
|---|---|---|
| 6,350,593 B1 | 2/2002 | Williams |
| 6,355,440 B1 | 3/2002 | Williams |
| 6,384,191 B1 | 5/2002 | Williams |
| 6,548,634 B1 | 4/2003 | Ballinger |
| 6,579,850 B1 | 6/2003 | Nabeshima |
| 6,639,063 B1 | 10/2003 | Edwards |
| 6,656,728 B1 | 12/2003 | Kavanaugh et al. |
| 6,716,626 B1 | 4/2004 | Itoh |
| 6,844,168 B1 | 1/2005 | Keifer |
| 7,259,248 B2 | 8/2007 | Itoh |
| 7,288,406 B2 | 10/2007 | Bogin |
| 7,381,804 B2 | 6/2008 | Osslund |
| 7,408,047 B1 | 8/2008 | Thomason |
| 7,459,540 B1 | 12/2008 | Thomason et al. |
| 7,491,697 B2 | 2/2009 | Beals |
| 7,531,304 B2 | 5/2009 | Bange |
| 7,537,903 B2 | 5/2009 | Kuro-o |
| 7,563,769 B2 | 7/2009 | Bogin |
| 7,645,857 B2 | 1/2010 | Zhou |
| 7,667,005 B2 | 2/2010 | Nabeshima |
| 7,667,008 B2 | 2/2010 | Thomason |
| 7,671,180 B2 | 3/2010 | Thomason |
| 7,678,890 B2 | 3/2010 | Bosch |
| 7,695,938 B2 | 4/2010 | Thomason |
| 7,696,153 B2 | 4/2010 | Nissen et al. |
| 7,696,172 B2 | 4/2010 | Thomason |
| 7,700,558 B2 | 4/2010 | Thomason |
| 7,704,952 B2 | 4/2010 | Thomason |
| 7,727,742 B2 | 6/2010 | Thomason |
| 7,741,078 B2 | 6/2010 | Imamura |
| 7,879,323 B2 | 2/2011 | Thomason et al. |
| 7,887,799 B2 | 2/2011 | Thomason |
| 2001/0012628 A1 | 8/2001 | Agarwal et al. |
| 2002/0081663 A1 | 6/2002 | Conklin |
| 2002/0164713 A1 | 11/2002 | Itoh |
| 2003/0220246 A1 | 11/2003 | Conklin |
| 2004/0018499 A1 | 1/2004 | Lal |
| 2004/0057950 A1 | 3/2004 | Waksal et al. |
| 2004/0063910 A1 | 4/2004 | Kavanaugh et al. |
| 2004/0185494 A1 | 9/2004 | Itoh |
| 2004/0259780 A1 | 12/2004 | Glasebrook |
| 2005/0037457 A1 | 2/2005 | Itoh |
| 2005/0176631 A1 | 8/2005 | Heuer |
| 2005/0187150 A1 | 8/2005 | Mohammadi |
| 2006/0223114 A1 | 10/2006 | Stemmer et al. |
| 2007/0036806 A1 | 2/2007 | Glaesner |
| 2007/0128619 A1 | 6/2007 | Itoh |
| 2007/0142278 A1 | 6/2007 | Beals et al. |
| 2007/0184444 A1 | 8/2007 | Abbas et al. |
| 2007/0237768 A1 | 10/2007 | Glaesner |
| 2007/0238657 A1 | 10/2007 | Itoh |
| 2007/0265200 A1 | 11/2007 | Glaesner |
| 2007/0274981 A1 | 11/2007 | Sun et al. |
| 2007/0293430 A1 | 12/2007 | Frye |
| 2007/0299007 A1 | 12/2007 | Frye |
| 2008/0071065 A1 | 3/2008 | Thomason |
| 2008/0071066 A1 | 3/2008 | Thomason |
| 2008/0103096 A1 | 5/2008 | Frye |
| 2008/0119403 A1 | 5/2008 | Imamura et al. |
| 2008/0124344 A1 | 5/2008 | Combs et al. |
| 2008/0242607 A1 | 10/2008 | DeFrees |
| 2008/0248959 A1 | 10/2008 | DeFrees |
| 2008/0253992 A1 | 10/2008 | DeFrees |
| 2008/0255040 A1 | 10/2008 | DeFrees |
| 2008/0255045 A1 | 10/2008 | Cujec |
| 2008/0261236 A1 | 10/2008 | Kuro-o |
| 2008/0261875 A1 | 10/2008 | Etgen |
| 2008/0274958 A1 | 11/2008 | DeFrees |
| 2009/0074776 A1 | 3/2009 | Itoh |
| 2009/0098131 A1 | 4/2009 | Clark et al. |
| 2009/0118190 A1 | 5/2009 | Beals et al. |
| 2009/0123462 A1 | 5/2009 | Bange |
| 2009/0192087 A1 | 7/2009 | Glass |
| 2009/0192133 A1 | 7/2009 | Horton et al. |
| 2009/0202554 A1 | 8/2009 | Berezin et al. |
| 2009/0297509 A1 | 12/2009 | Waksal et al. |
| 2009/0305986 A1 | 12/2009 | Belouski |
| 2010/0034817 A1 | 2/2010 | Abbas et al. |
| 2010/0047251 A1 | 2/2010 | Yayon et al. |
| 2010/0087627 A1 | 4/2010 | Marshall et al. |
| 2010/0158911 A1 | 6/2010 | Williams |
| 2010/0158914 A1 | 6/2010 | Desnoyers |
| 2010/0184665 A1 | 7/2010 | Suzuki |
| 2010/0226921 A1 | 9/2010 | Thomason |
| 2010/0233169 A1 | 9/2010 | Thomason |
| 2010/0285131 A1 | 11/2010 | Belouski |
| 2010/0310566 A1 | 12/2010 | Thomason |
| 2011/0003302 A1 | 1/2011 | Thomason |
| 2011/0008347 A1 | 1/2011 | Ullrich et al. |
| 2012/0003216 A1 | 1/2012 | Belouski et al. |
| 2012/0052069 A1 | 3/2012 | Belouski et al. |
| 2012/0087920 A1 | 4/2012 | Belouski et al. |
| 2012/0213779 A1 | 8/2012 | Belouski et al. |

FOREIGN PATENT DOCUMENTS

| | | |
|---|---|---|
| EP | 58481 B1 | 8/1982 |
| EP | 88046 B2 | 9/1983 |
| EP | 0133988 A1 | 3/1985 |
| EP | 143949 B1 | 6/1985 |
| EP | 154316 B1 | 9/1985 |
| EP | 401384 B1 | 12/1990 |
| EP | 505500 A1 | 9/1992 |
| EP | 0545343 A1 | 6/1993 |
| EP | 315456 B1 | 6/1994 |
| EP | 0 133 988 A2 | 8/1994 |
| EP | 546073 B1 | 9/1997 |
| EP | 1697420 A2 | 7/2005 |
| EP | 2060270 A2 | 5/2009 |
| EP | 2163626 A1 | 3/2010 |
| JP | 2002-112772 A | 4/2002 |
| JP | 2003-334088 A | 11/2003 |
| WO | 90/04036 A1 | 4/1990 |
| WO | 91/09955 A1 | 7/1991 |
| WO | 91/10425 A1 | 7/1991 |
| WO | 91/10470 A1 | 7/1991 |
| WO | 91/10741 A1 | 7/1991 |
| WO | 93/15722 A1 | 8/1993 |
| WO | 94/02602 A1 | 2/1994 |
| WO | 94/20069 A1 | 9/1994 |
| WO | 94/26122 A1 | 12/1994 |
| WO | 95/05452 A1 | 2/1995 |
| WO | 95/34670 A1 | 12/1995 |
| WO | 96/11953 A1 | 4/1996 |
| WO | 96/32478 A1 | 10/1996 |
| WO | 96/33735 A1 | 10/1996 |
| WO | 96/37609 A1 | 11/1996 |
| WO | 96/40958 A1 | 12/1996 |
| WO | 96/41865 A1 | 12/1996 |
| WO | 97/31899 A1 | 9/1997 |
| WO | 97/34631 A | 9/1997 |
| WO | 99/10494 A1 | 3/1999 |
| WO | 99/27100 C2 | 6/1999 |
| WO | 00/18921 A2 | 4/2000 |
| WO | 00/24762 A3 | 5/2000 |
| WO | 00/27885 A1 | 5/2000 |
| WO | 00/54813 A2 | 9/2000 |
| WO | 01/18172 A2 | 3/2001 |
| WO | 01/18209 A1 | 3/2001 |
| WO | 01/32678 A1 | 5/2001 |
| WO | 01/36640 A2 | 5/2001 |
| WO | 01/38357 A2 | 5/2001 |
| WO | 01/49849 A1 | 7/2001 |
| WO | 01/72957 A2 | 10/2001 |
| WO | 02/36732 C2 | 5/2002 |
| WO | 02/102854 A2 | 12/2002 |
| WO | 03/011213 A2 | 2/2003 |
| WO | 03/059270 A2 | 7/2003 |
| WO | 2004/022095 A1 | 3/2004 |
| WO | 2004/044011 A2 | 5/2004 |
| WO | 2004/083381 A2 | 9/2004 |
| WO | 2004/100976 A1 | 11/2004 |
| WO | 2004/110472 A2 | 12/2004 |
| WO | 2005/037235 A2 | 4/2005 |

(56) References Cited

FOREIGN PATENT DOCUMENTS

| WO | 2005/061712 A2 | 7/2005 |
|---|---|---|
| WO | 2005/072769 A1 | 8/2005 |
| WO | 2005/091944 A1 | 10/2005 |
| WO | 2005/113606 A2 | 12/2005 |
| WO | 2006/095559 A1 | 1/2006 |
| WO | 2006/028595 A2 | 3/2006 |
| WO | 2006/028714 A1 | 3/2006 |
| WO | 2006/050247 A2 | 5/2006 |
| WO | 2006/065582 A2 | 6/2006 |
| WO | 2006/078463 A2 | 7/2006 |
| WO | 2006/130527 A2 | 7/2006 |
| WO | 2008/153705 A2 | 12/2006 |
| WO | 2007/021423 A2 | 2/2007 |
| WO | 2007/055789 A2 | 5/2007 |
| WO | 2008/011633 A2 | 1/2008 |
| WO | 2008/066498 A1 | 6/2008 |
| WO | 2008/121563 A2 | 10/2008 |
| WO | 2008/123625 A1 | 10/2008 |
| WO | 2008/135993 A1 | 11/2008 |
| WO | 2008/149521 A1 | 12/2008 |
| WO | 2008/151258 A2 | 12/2008 |
| WO | 2009/020802 A2 | 2/2009 |
| WO | 2007/100695 A2 | 9/2009 |
| WO | 2009/117622 A2 | 9/2009 |
| WO | 2009/149171 A2 | 12/2009 |
| WO | 2010006214 A1 | 1/2010 |
| WO | 2010/129503 A1 | 11/2010 |

OTHER PUBLICATIONS

Bork (2000), "Powers and pitfalls in sequence analysis: the 70% hurdle," Genorne Res. 10(4): 398-400.

Bork et al. (1996), "Go hunting in sequence databases but watch out for the traps," Trends Genet. 12(10): 425-27.

Branch (1998), "A good an antisense molecule is hard to find." Trends Biochem Sci. 23(2): 45-50.

Brenner (1999), "Errors in genome annotation," Trends Genet, 15(4): 132-33.

Brodeur et al., Monoclonal Antibody Production Techniques and Applications 51-63 (Marcal Dekker, Inc 1987).

Bruggermann et al., (1993), "Designer mice: the production of human antibody repertoires in transgenic animals" Year in Immuno. 7: 33.

Capon et al., (1999), "Designing CD4 immunoadnesins for AIDS therapy" Nature 337: 525-31.

Cunha et al. (1996), "Keratinocyte growth factor as mediator of mesenchymal-epithelial interactions in the development of androgen target organs." Semin Cell Dev Biol 7: 203-310.

Dailey, et al. (2005), "Mechanisms underlying differential responses to FGF signaling," Cytokine & Growth Factor Reviews 16: 233-247.

Debernardez Clark E., (1998), "Refolding of recombinant proteins" Curr. Opin. Biotechnol. 9: 157-63.

Doerks et al. (1994) "Protein annotation: detective work for function prediction," Trends Genet 14(6); 248-50.

Ebadi et al. (1997), "Neurotrophins and their receptors in nerve injury and repair." Neurochem. Int. 30: 347-74.

Econs and McEnery (1997) "Autosomal dominant hypophosphatemic rickets/osteomalacia:clinical characterization of a novel renal phosphate-wasting disorder," J Clin Engocrincil Metal 82:674-581.

Ellison et al., (1982), "The nucleotide sequence of a human immunaglobulin Cyl gene" Nucleic Acids Res. 10: 4071-9).

Eppstein, et al., (1985) "Biological activity of liposome-encapsulated murine interferon y is mediated by a cell membrane receptor" Proc. Natl. Acad. Sci. U.S.A. 82:3688-92.

Eswarakumar, et al. (2005) "Cellular signaling by fibroblast growth factor receptors" Cytokine & Growth Factor Reviews 16: 139-149.

Faham. S. et al., (1998) "Diversity does make a difference: fibroblast growth factor-heparin interactions." Curr. Opin. Struct. Biol. 8(5): 578-586.

Fausto, N., "Mouse fiver tumorigenesis: models, mechanisms, and relevance to human disease," Seminars in Liver Disease 19:243-252 (1909).

Francis et al, (1992), "Protein modification and fusion proteins," Focus on Growth Factors 3:4-10.

Freiberg & Zhu, (2004) "Polymar microspheras for controlled drug release" Int J. Pharm. 262:1-16.

Fu, Ling, et al, (2004) "Fibroblast growth factor 19 increases metabolic rate and reverses dietary and ieptin-deficient diabetes," Endocroinology 145:2594-2603.

Fukumoto, Seji, and Yamashita, T., (2007). "FGF23 is a hormone-regulating phosphate metabolism-Unique Biological characteristics of FGF21," Bone 40:1190-1195.

Fukumoto, Seji, (2008) "Actions and mode of actions of FGF19 subfamily members," Endocr. J. 55:23-31.

Galzie Z. et al. (1997), "Fibroblast Growth Factors and their Receptors". Biochemistry and Cell Biology 75(6):669-685.

Ghielli et al. (1998), "Regeneration processes in the kidney after acute injury: role of infiltrating cells." Exp. Nephrol. 6: 502-507.

Goetz et al, (2007), "BBA—Molecular and Cell Biology of Lipids," Mol. Cell. Biol. 27:3417-28.

Goldfarb (1996), "Functions of fibroblast growth factors in vertebrate development," Cytokine Growth Factor Rev. 7(4): 311-325.

Harmer, Nicholas J., et al. (2004), "The crystal structure of fibroblast growth factor (FGF) 19 reveals novel features of the FGF family and offers a structural basis for its unusual receptor affinity," Biochem 43(3): 629-640.

Ho, Han Kiat, et al. (2009), "Fibroblast growth factor receptor 4 regulates proliferation, anti-apoptosis and alpha-fetoprotein secretion during hepatocellular carcinoma progression and represents a potential target for therapeutic intervention," J. Hepatol. 50:118-127.

Hoogenboom et al., (1991), "By-passing immunisation. Human antibodies from synthetic repertoires of germline VH gene segments rearranged in vitro"J. Mol. Biol. 227: 381.

Hoppenreijs et al. (1996), "Cornmeal endothelium and growth factors." Surv. Ophthalmol. 41: 155-64.

Hsu et al. (1999). "Heparin Is Essential for a Single Keratinocyte Growth Factor Molecule To Bind and Form a Complex with Two Molecules of the Extracellular Domain of Its Receptor," Biochemistry 38: 2523-34.

Beenken, Andrew and Monammadi, Moosa (2009), "The FGF family: biology,pathophysiology and therapy." Nature Reviews 8:235-253.

R&D Systems, Catelog No. MAB3738, Lot No. XRU02 (2007), "Monoclonal anti-human/mouse Klotho Beta antibody," XP-002624719.

Suzuki, Masashi et al. (2008) "Beta-klotho is required for fibroblast growth factor (FGF) 21 signalling through FGF receptor (FGFR) 1c and FGFR3c," Mol. Endocr. 22(4):1006-1014.

Li, Xiaofan, et al. (2009) "Inhibition of lipolysis may contribute to the acute regulation of plasma FFA and glucose by FGF21 in ob/ob mice," FEBS Letters 583:323-03234.

Wu, Xinle et al. (2007) "Co-receptor requirements for fibroblast growth factor-19 signaling" J. Biol. Chem. 282 (40): 29069-29012.

Wu, Xinle et al. (2010) "Selective activation of FGFR4 by an FGF19 variant does not improve glucose metabolism in ob/ob mice." PNAS 106 (34): 14379-14384.

Wu, Xinle et al (2010) "Separating milogenic and metabolic activities of fibroblast growth factor 19 (FGF19)." PNAS 107 (32): 14158-14163.

Xu, Jing et al. (2009) "Acute glucose-lowering and insulin-sensitizing action of FGF21 in insulin-resistane mouse models-association with liver and adipose tissue effects." Am. J. Physiol. Endocrinol. Metab. 297: E1105-E1114.

Podolsky (1997), "Healing the epithelium: solving the problem from two sides." J. Gastroenterol. 32: 122-6.

Polejaeva et al. (2000), "New advances in somatic cell nuclear transfer: application in transgenesis," Theriogenology 5(1): 117-26.

Ratajczak, (1997), "Fiarobtast growth factors and early hemopoietic cell development." Leuk. Lymphoma 27: 221-9.

Remington's Pharmaceutical Sciences (18th Ed., A.R. Gennaro, ed., Mack Publishing Company 1990).

Riechmann et al., (1998), "Reshaping human antibodies for therapy" Nature 332: 323-27.

Rudolph et al., (1997), "Folding proteins," Protein Function: A Practical Approach (Creighton, ed., New York. IRL, Press) 57-99.

(56) References Cited

OTHER PUBLICATIONS

Rulicke et al. (2000). "Germ line tansformation of mammals by pronuclear microinjection," Exp. Physiol. 85(6): 589-601.
Sambrook, et al. Molecular Cloning: A Laboratory Manual (Cold Spring Harbor Laboratory Press, 1989).
Schlessinger, J. et al., (2000), "Crystal Structure of a Ternary FGF-EGFR-Heparin Complex Reveals a Dual Role for Heparin in FGFR Binding and Dimerization," Mol. Cell 6:743-50.
Sidman et al., (1983), "Controlled release of macromolecules and pharmaceuticals from synthetic polypeptide based on glutamic acid" Biopolymers 22: 547-56.
Skolnick et al. (2000). "From genes to protein structure and function: novel applications of computational approaches in the genomic era," Trends Biotechnol. 18(1): 34-39.
Smallwood et al. (1996), "Fibroblast Growth Factor (FGF) homologous factors: new members of the FGF family implicated in nervous system development", PNAS 93:9850-9857.
Smith et al. (1997), "The challenges of genome sequence annotation or 'the devil is in the details,'" Nat. Biotechnol. 15(12): 1222-23.
Tomlinson, E. et al. (2002) "Transgenic mice expressing human fibroblast growth factor-19 display increased metabolic rate and decreased adiposity," Endocrinology 143:17419-1747.
Trouiller, et al. (2006) "MSH2 is essential for the preservation of genome integrity and prevents homeologous recombination in the moss Physcomitrella patens" Nucleic Acids Research vol. 34, (1):232-242.
Verhoeyen et al. (1997), "Reshaping human antibodies: grafting an antilysozyme activity" Science 239: 1534-36.
Verma et al. (1997) "Gene therapy—promises, problems, and prospects." Nature 389: 239-242. (Examiner).
Wang et al. (1999), "Rapid analysis of gene expression (RAGE) facilitates universal expression profiling." Nuc. Acids Res. 27:4609-4618.
Webster (1997), "Growth factors and myelin regeneration in multiple sclerosis." Mult. Scler. 3:113-20.
Wente et al., (2006), "Fibroblast Growth Factor-21 Improves Pancreatic B-Cell Function and Survival by Activation of Extracellular Signal-Regulated Kinase ½ and Akt Signaling Pathways" Diabetes 55:2470-2478.
Wischke & Schwendeman, 2008, "Principles of encapsulating hydrophobic drugs in PLA/PLGA microparticles" Int. J. Pharm, 364: 298-327.
Wu, Xinle et al. (2008) "C-terminal Tail of FGF19 Determines Its Specificiy toward Klotho Co-receptors," J. Biol. Chem. 283(48):33304-9.
Xu et al., (2009) "Fibroblast Growth Factor 21 Reverses Hepatic Steatosis, Increases Energy Expenditure, and Improves Insulin Sensitivity in Diet-Induced Obese Mice" Diabetes 58(1):250-9.
Yamaoka and Itakura (1999), "Development of pancreatic islets (review)," Int. J. Mol. Med. 3: 247-61.
Yie et al., 2009, "FGF21 N- and C-termini play different roles in receptor interaction and activation"FEBS Lett. 583:19-24.
Zola, Monoclonal Antibodies: A Manual of Techniques 147-158 (CRC Press, Inc., 1987).
Hu et al., (1998), "FGF-18, a novel member of the fibroblast growth factor family, stimulates hepatic and intestinal proliferation," Mol. Cell. Biol. 18(10): 6063-6074.
Hull et al (1997), "Healing with basic fibroblast growth factor is associated with reduced indomethacin induced relapse in a human model of gastric ulceration," Gut 40: 204-10.
Inagaki, T. et al. (2005) "Fibroblast growth factor 15 functions as an enterohepatic signal to regulate bile acid homeostasis," Cell. Metab. 2: 217-225.
Ishibashi et al., (2005), "Is arginine a protein-denaturant?" Protein Expr. Purif. 42: 1-6.
Itoh and Ornitz (2004), "Evolution of the FGF and FGFR gene families," Trends in Genetics 20(11): 563-569.
Jakobovits et al., (1993) "Analysis of homozygous mutant chimeric mice: deletion of the immunoglobulin heavy-chain joining region blocks B-cell development and antibody production" Proc. Natl. Acad. Sci. U.S.A. 90: 2551-55.
Jakobovits et al., (1993), "Germ-line transmission and expression of a human-derived yeast artificial chromosome"Nature 362: 255-58.
Jones et al., (1986), "Replacing the complimentarily-determining regions in a human antibody with those from a mouse" Nature 321: 522-25.
Kohler et al., (1975), "Continuous cultures of fused cells secreting antibody of predefined specificity," Nature 256: 495-97.
Kurosu, Hiroshi et al., (2007), "Tissue-specific Expression of Klotho and Fibroblast Growth Factor (FGF) Receptor Isoforms Determines Metabolic Activity of FGF19 and FGF," J. Biol. Chem. 282:26687-26695.
Bork, et al. (1998), "Predicting functions from protein sequences—where are the bottlenecks?" Nature Genetics 18(4): 313-18.
Kaufman et al. (1999), "Transgenic analysis of a 100-kb human beta-globin cluster-containing DNA fragment propagated as a bacterial artificial chromosoma." Bood 94: 3178-3184.
Kennell (1971), "Principles and practices of nucleic acid hybridization," Progr. Nucl. Acid Res. Mol. Biol. 11: 259-301.
Kharitonenkov et al, (2005), "FGF-21 as a novel metabolic regulator." J. Clin. Invest. 115: 1627-1635.
Kharitonenkov et al. (2006), "The metatabolic state of diabetic monkeys is regulated by FGF-21" Endocrinology DOI:10.1210/en.2006-1168.
Kharitonenkov et al. (2007), "The metabolic state of diabetic monkeys is regulated by FGF-21" Endocrinology 146:774-781.
Kharitonenkov et al. (2008), "Fibroblast Growth Factor-21 as a Therapeutic Agent for Metabolic Diseases" Biodrugs 22 1: 37-44.
Kornmann et al. (1998), "Role of fibrobiast growth factors and their receptors in pancreatic cancer and chronic pancreatilis." Pancreas 17: 169-75.
Kozbor, (1984) "A human hybrid myeloma for production of human monoclonal antibodies" J. Immunol. 133: 3001.
Laemmli, (1970), "Cleavage of structural proteins during the assembly of the head of bacteriophage T4" Nature 227: 680-85.
Langer et al., (1981), "Biocompatibility of polymeric delivery systems for macromolecules" J. Biomed. Mater. Res. 15: 267-277.
Langer et al., (1982), "Controlled release of macromolecules" Chem. Tech. 12: 98-105.
Ledley (1996), "Pharmaceutical Approach to Somatic Gene Therapy," Pharm. Res. 13(11): 1595-1614. (Examiner).
Lewis el al. (1997), "Angiogenesis by gene therapy: a new horizon for myocardial revascularization!" Cardiovasc. Res. 135: 490-497.
Liu et al. (2007), "FGF18 is required for early chondrocyte proliferation, hypertrophy and vascular invasion of the growth plate." Dev. Biol. 302: 80-91.
Mahairas et al. (1999), "Sequence-tagged connectors: a sequence approach to mapping and scanning the human genome." PNAS 96(17): 9736-9744.
Mannall et al., (2007), "Factors affecting protein refolding yields in a fed-batch and batch-refolding system" Biotechnol. Bioeng. 97: 1523-34.
Marks et al. (1991), "By-passing immunization. Human antibodies from V-gene libraries displayed on phage" J. Mol. Biol. 222: 551-597.
Mikkelsen (1993), "Interpreting sequence motifs: a cautionary note," Trends Genet. 9(5): 15.
Mohammadi, et al. (2005), "Structural basis for fibroblast growth factor receptor activation" Cytokine & Growth Factor Reviews 16: 107-137.
Morrison et al., (1985), "Chimeric human antibody molecules: mouse antigen-binding domains with human constant region domains" Proc. Natl. Acad. Sci. U.S.A. 81: 6851-55.
Moyers et al. (2007), "Molecular Determinants FGF-21 Activity-Synergy and Cross-Talk with PPARy Signaling" J. Cell. Phys. 210: 1-6.
Nakamura et al. (1995), "The murine lymphotoxin-beta receptor cDNA: isolation by the signal sequence trap and chromosomal mapping," Genomics 30(2): 312-19.

(56) References Cited

OTHER PUBLICATIONS

Ngo et al. (1994), "Computational complexity, protein structsure prediction, and the Levinthal paradox," in The Protein Folding Problem and Tertiary Structure Prediction, Merz & Le Grand ed., Birkhauser; Boston, pp. 491-495.

Nicholes, Katrina et al., (2002), "A mouse model of hepatocellular carcinoma: ectopic expression of fibroblast growth factor 19 in skeletal muscle of transgenic mice," Am. J. Pathol. 160:2295-2307.

Nishimura et al. (2000), "Identification of a novel FGF, FGF-21, preferentially expressed in the liver(I)." Biochim Biophys Acta 21: 203-6.

Niyogi (1969), "The influence of chain and base composition on the specific association of oligoribonucleotides with denatured deoxyribonucleic add," J. Biol. Chem. 244(6): 1575-81.

Ogawa, Y., et al. (2005) "Klotho is required for metabolic activity of fibroblast growth factor 21," Proc. Natl. Acad. Sci. USA 104:7432-7437.

Parthiban et al. (2007), "Computational modeling of protein mutant stability: analysis and optimization of statistical potentials and structural features reveal insights into prediction model development," BMC Struct. Biol. 7:54.

Parthiban et al., (2006), "MSH2 is essential for the preservation of genome integrity and prevents homeologous recombination in the moss Physcomitrella patens" Nucleic Acids Res. 34: 232-42.

Peus and Pittelkow (1996), "Growth factors in hair organ development and the hair growth cycle." Dermatol. Clin. 14:559-72.

Phillips (2001), "The challenge of gene therapy and DNA delivery." J. Pharm. Pharmacology 53: 1169-1174.

Plotnikov et al. (1999), "Structural Basis for FGF Receptor Dimerization and Activation" Cell 98: 641-650.

Plotnikov et al. (2000), "Crystal Structures of Two FGF-FGFR Complexes Reveal the Determinants of Ligand-Receptor Specificity," Cell 101: 413-24.

Wu, X. et al. (2010) "FGF19 induced hepatolocyte proliferation is mediated through FGFR4 activation." J. Biol. Chem. 285:5165.

Ogawa et al. (2007), "Beta-klotho is required for metabolic activity of fibroblast growth factor 21," PNAS 104(18) 7432-7437.

Database UniProt Q9DDNO, Accession No. 09DDNO, "Fibroblast growth factor 19," XP002596987 (2001).

Database UniProt Q76B59, Accession No. Q76B59, "Fibroblast growth factor 19," XP002596988 (2004).

Database UniProt B3DHS4, Accession No. B3DHS4, "FGF19 protein," XP002596990 (2008).

Database UniProt B7U4G3, Accession No. B7U4G3, "FGF19," XP002596989 (2009).

Gupte, J., et al. (2011) "The FGFR D3 Domain Determines Receptor Selectivity for Fibroblast Growth Factor 21," Journal of Molecular Biology, vol. 408, pp. 491-502.

Kurosu et al., (2009) "The Klotho gene family as a regulator of endocrine fibroblast growth factors," Molecular and Cellular Endocrinology, vol. 299, pp. 72-78.

Kurosu et al., (2008) "The Klotho gene family and the endocrine fibroblast growth factors," Current Opinions in Nephrology and Hypertension, vol. 17, pp. 368-372.

Lin et al., (2007) "Liver-specific Activities of FGF19 Require Klotho beta," Journal of Biological Chemistry, vol. 282, No. 37, pp. 27277-27284.

Yie et al. 2012 "Understanding the Physical Interactions in the FGF21/β-Klotho Complex: Structural Requirements and Implications in FGF21 Signaling," ChemicaBiol Drug Des, vol. 79, pp. 398-410.

Wu, X. And Li, Y. (2011) Understanding the structure-function relationship between FGF19 and its motogenic and metabolic activities. In Endocrine FGFs and Klothos, edited by Makoto Kuro-o, Landes Bioscience and Springer Science Media, pp. 1-19.

Wu, X., et al. (2009) "Role of FGF19 induced FGFR4 activation in the regulation of glucose homeostatis." Aging, vol. 1, No. 12, pp. 1023-1027.

Wu, X. et al. (2010) "FGF19 induced hepatocyte proliferation is mediated through FGFR4 activation." Journal of Biological Chemistry, vol. 285, No. 8, pp. 5165-5170.

GenBank Acc. No. AQ175436, "HS_3207_A1_H09_CIT approved human genomic sperm library D *Homo sapeins* genomic clone Plate+3207 Col+17 Row+0, genomic survey sequence," US Natl. Lib. Med., Bethesday, MD, USA, Oct. 17, 1998, accessby by PTO Nov. 18, 2005.

GenBank Acc. No. AV050323, Jun. 16, 1999, Mus musculus pancreas C57BL/6J adult Mus musculus clone 1810013H18, mRNA sequence, US Natl. Lib. Med., Bethesda, MD, USA Jun. 22, 1999, accessed by PTO Nov. 18, 2005.

GenBank Acc. No. BAA99415, Aug. 3, 2000.

GenBank Acc. No. BAA99416, Jul. 11, 2000.

GenBank Acc. No. NP 061986, Apr. 6, 2003.

GenBank Acc. No. Q9NSA1, Oct. 1, 2000.

GenBank Accession No. AB006136, Aug. 27, 1997, XP002165898.

K69C R175C Y179C

FIG. 4
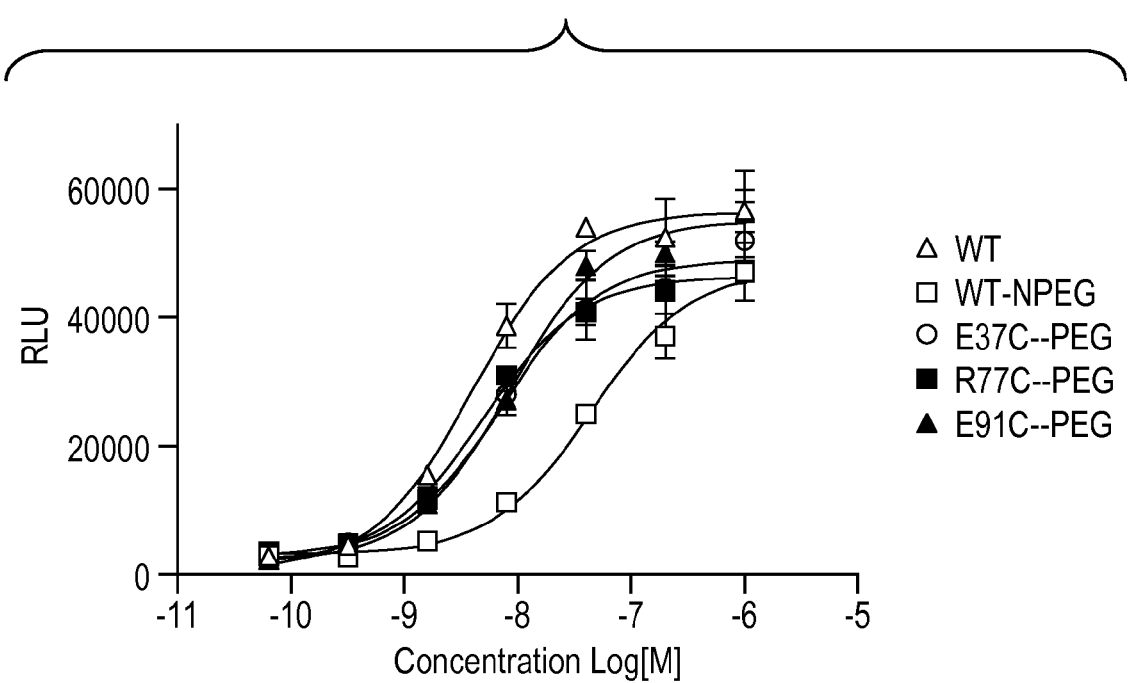
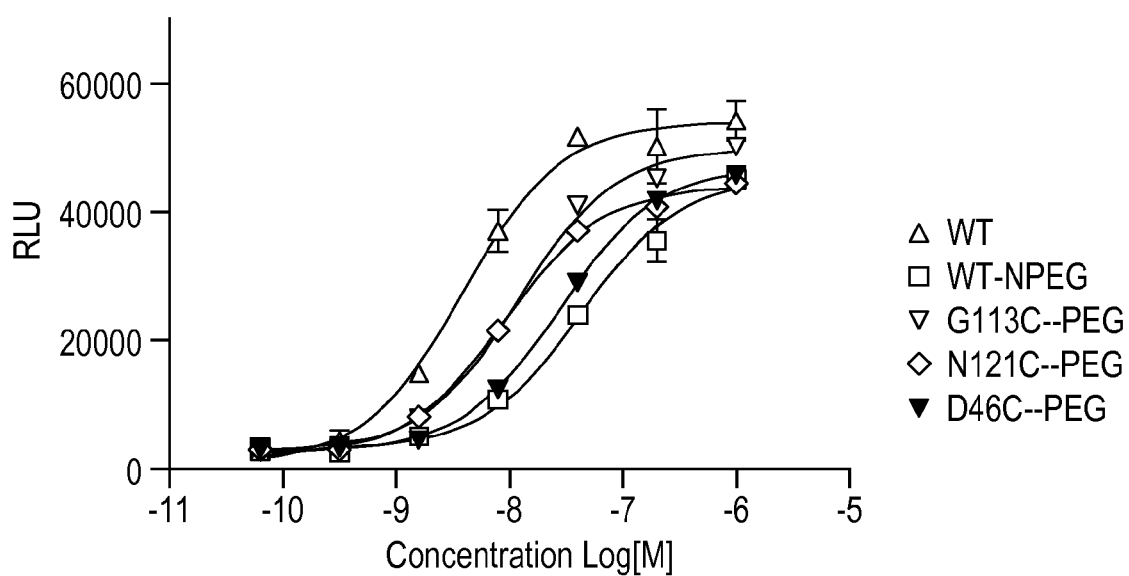

FIG. 5
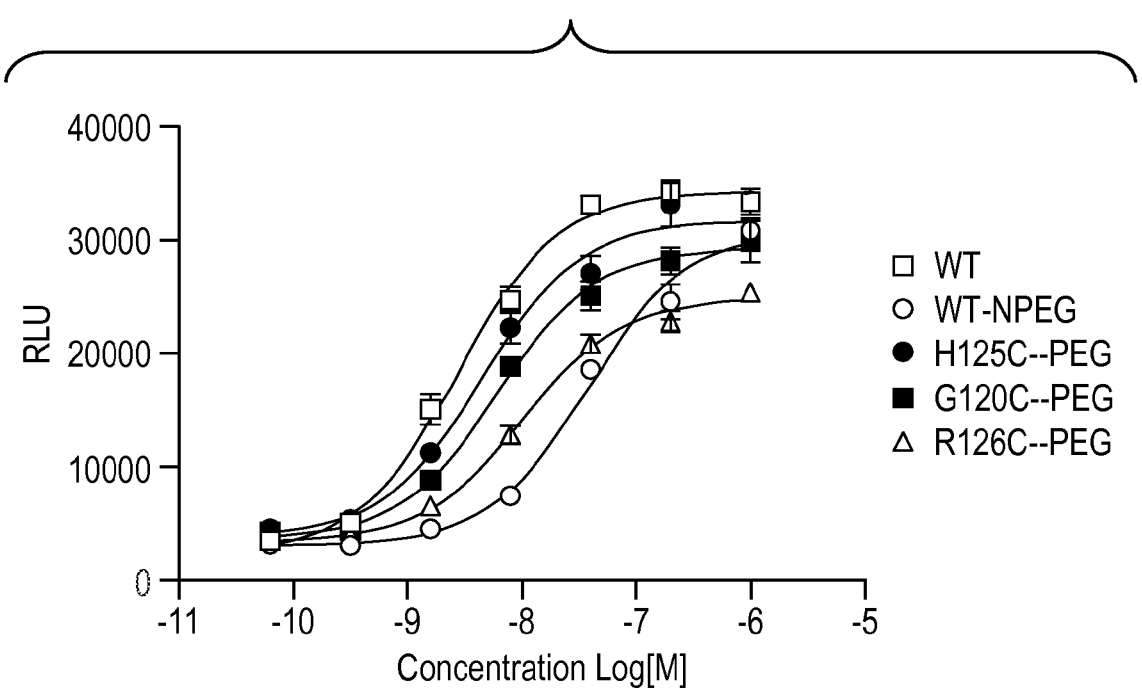
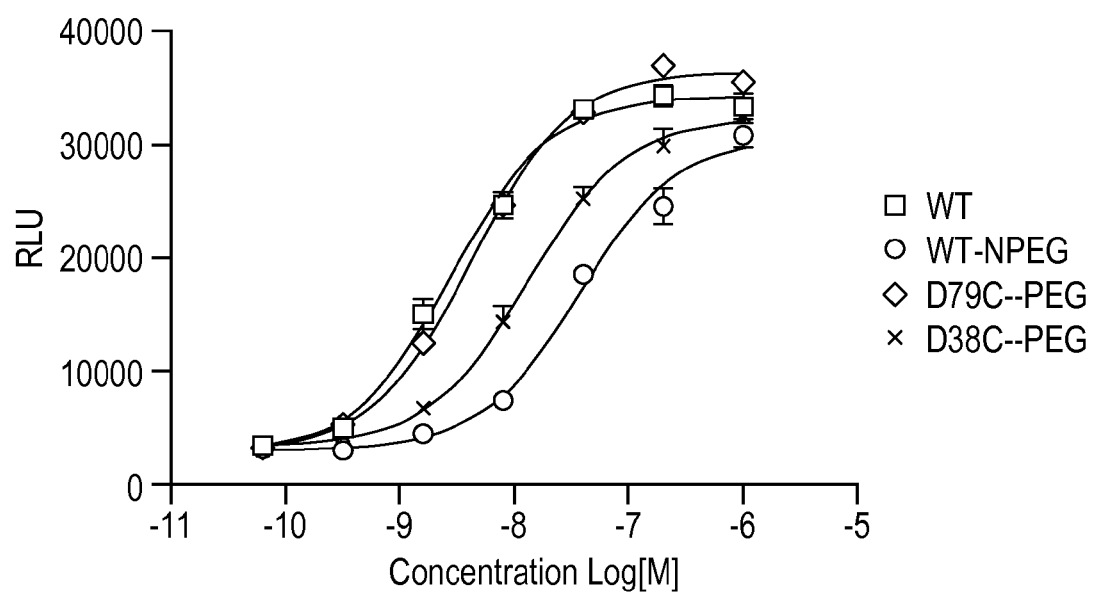

FIG. 6
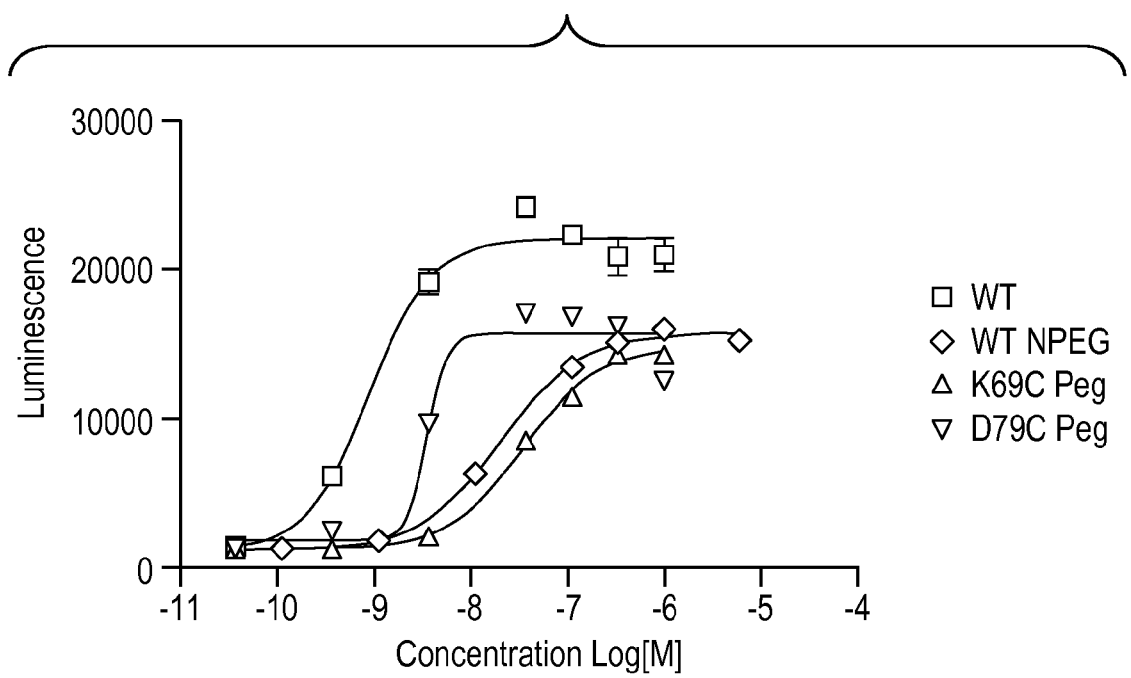
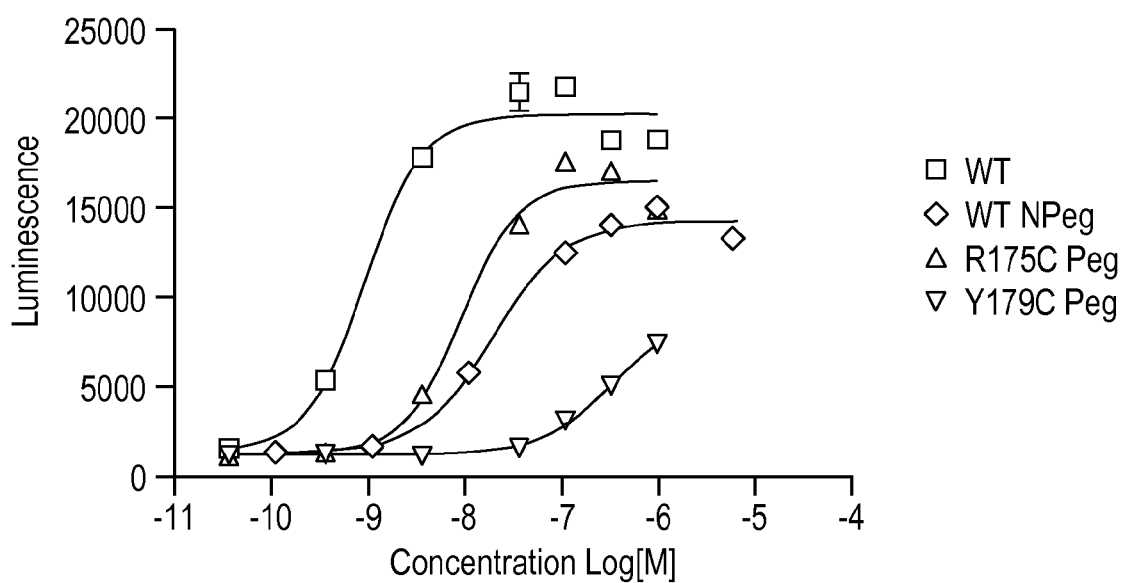

FIG. 10
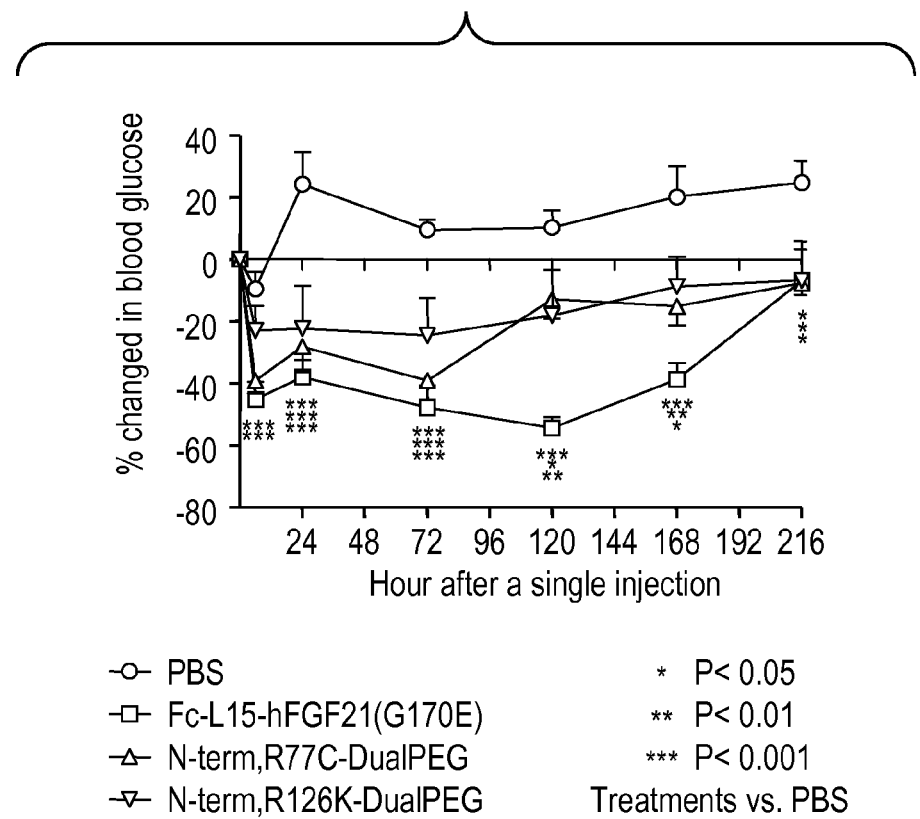
- ○ PBS
- □ Fc-L15-hFGF21(G170E)
- △ N-term,R77C-DualPEG
- ▽ N-term,R126K-DualPEG
- \* P< 0.05
- \*\* P< 0.01
- \*\*\* P< 0.001
Treatments vs. PBS
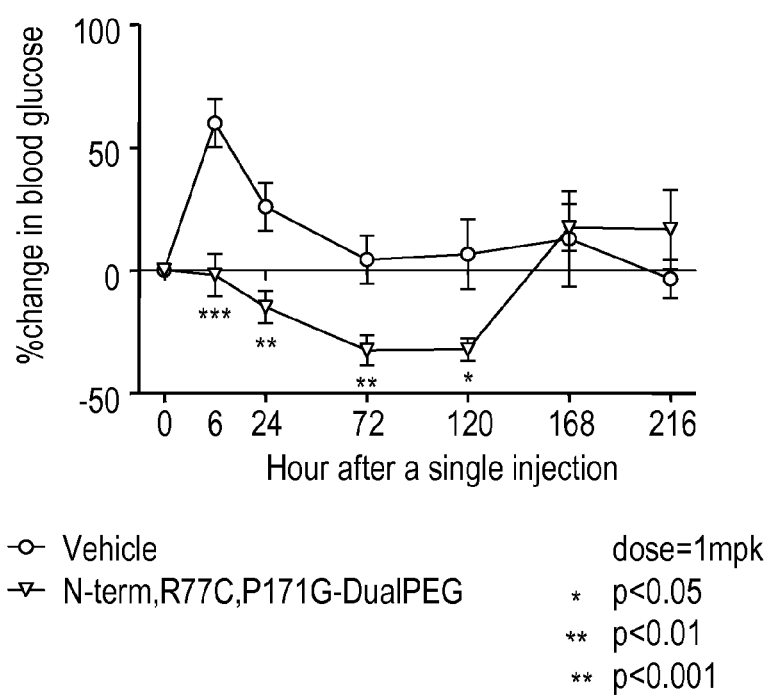
- ○ Vehicle
- ▽ N-term,R77C,P171G-DualPEG
dose=1mpk
- \* p<0.05
- \*\* p<0.01
- \*\* p<0.001

-○- vehicle
-□- E37C,R77C,P171G-DualPEG
-△- E91C,H125C,P171G-DualPEG
-◇- 2xFGF21(E37C,P171G)-Tethered molecule
-●- 2xFGF21(R77C,P171G)-Tethered molecule dose=1mpk
\* p<0.05
\*\* p<0.01
\*\*\* p<0.001

FIG. 16
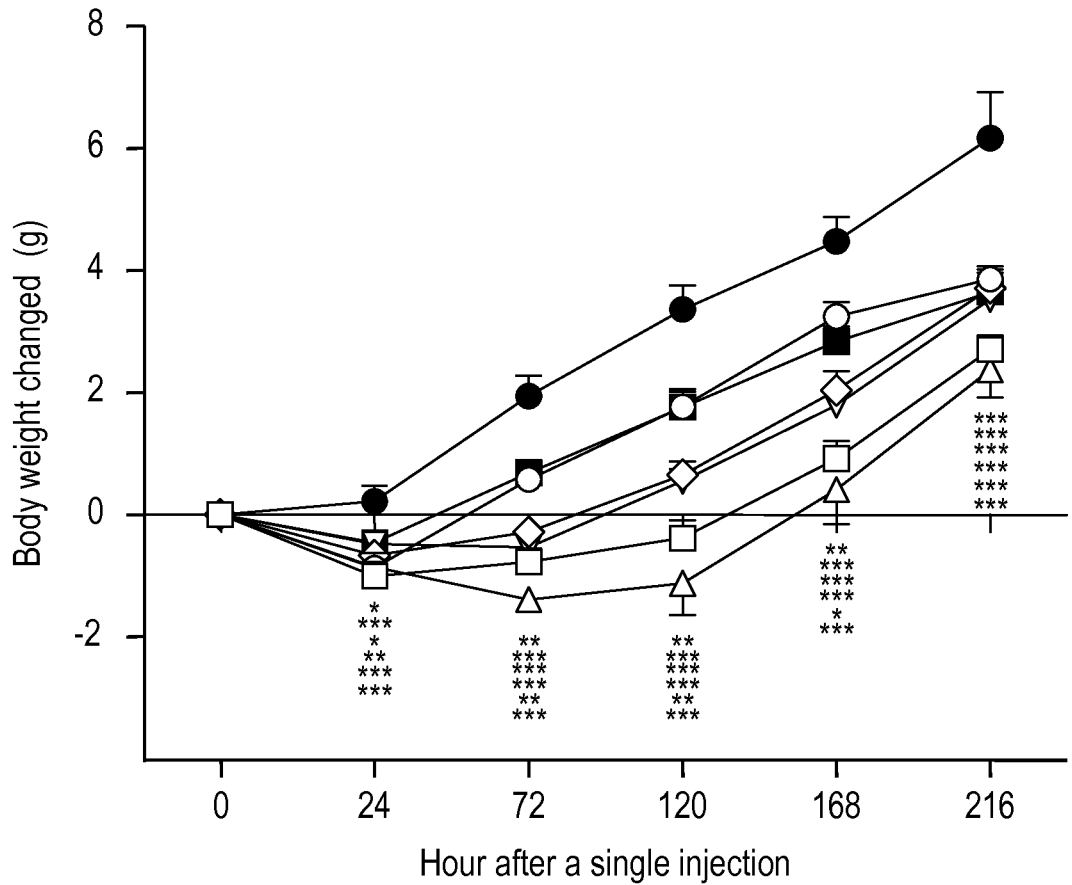
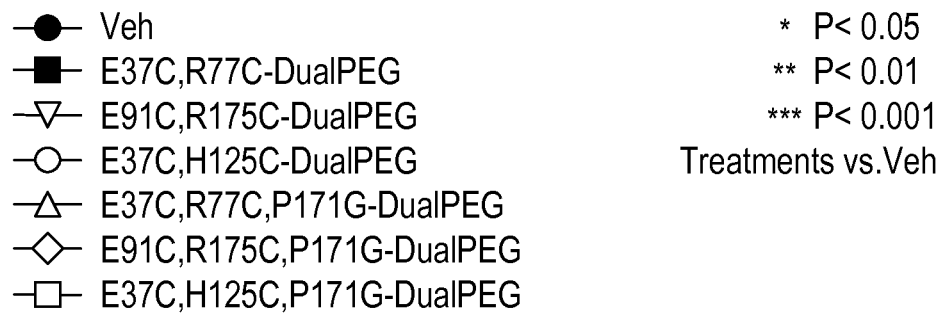

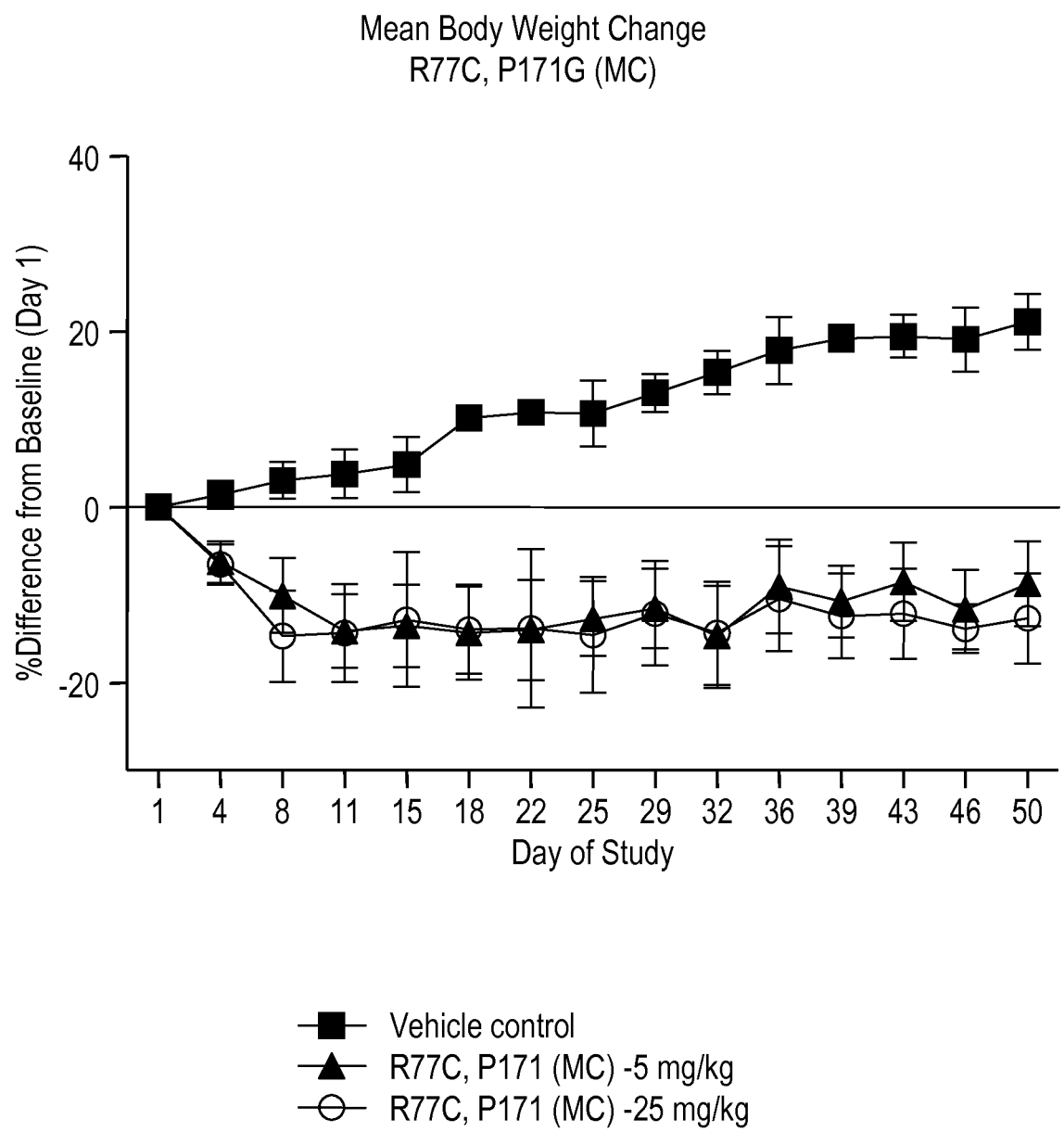

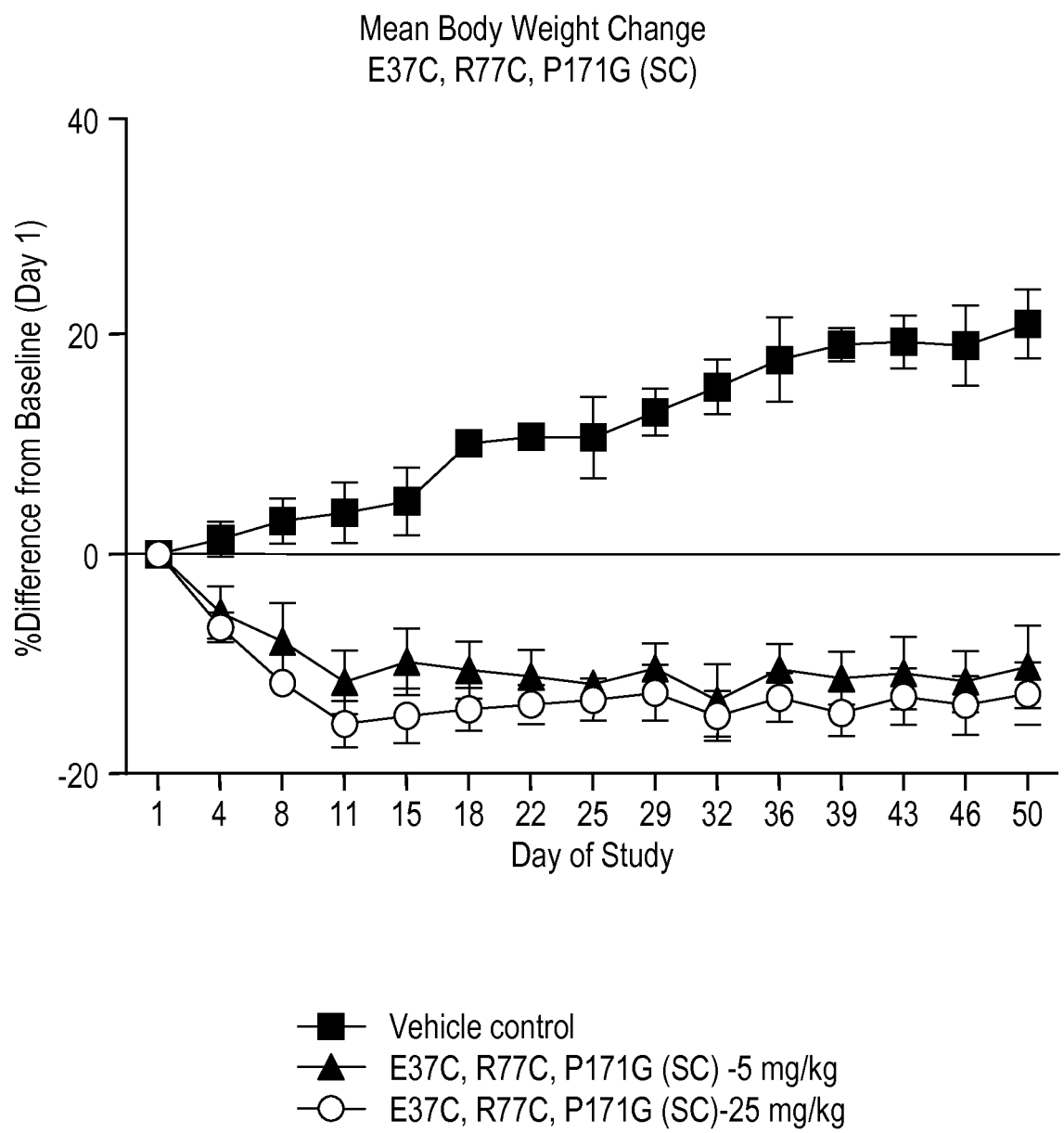

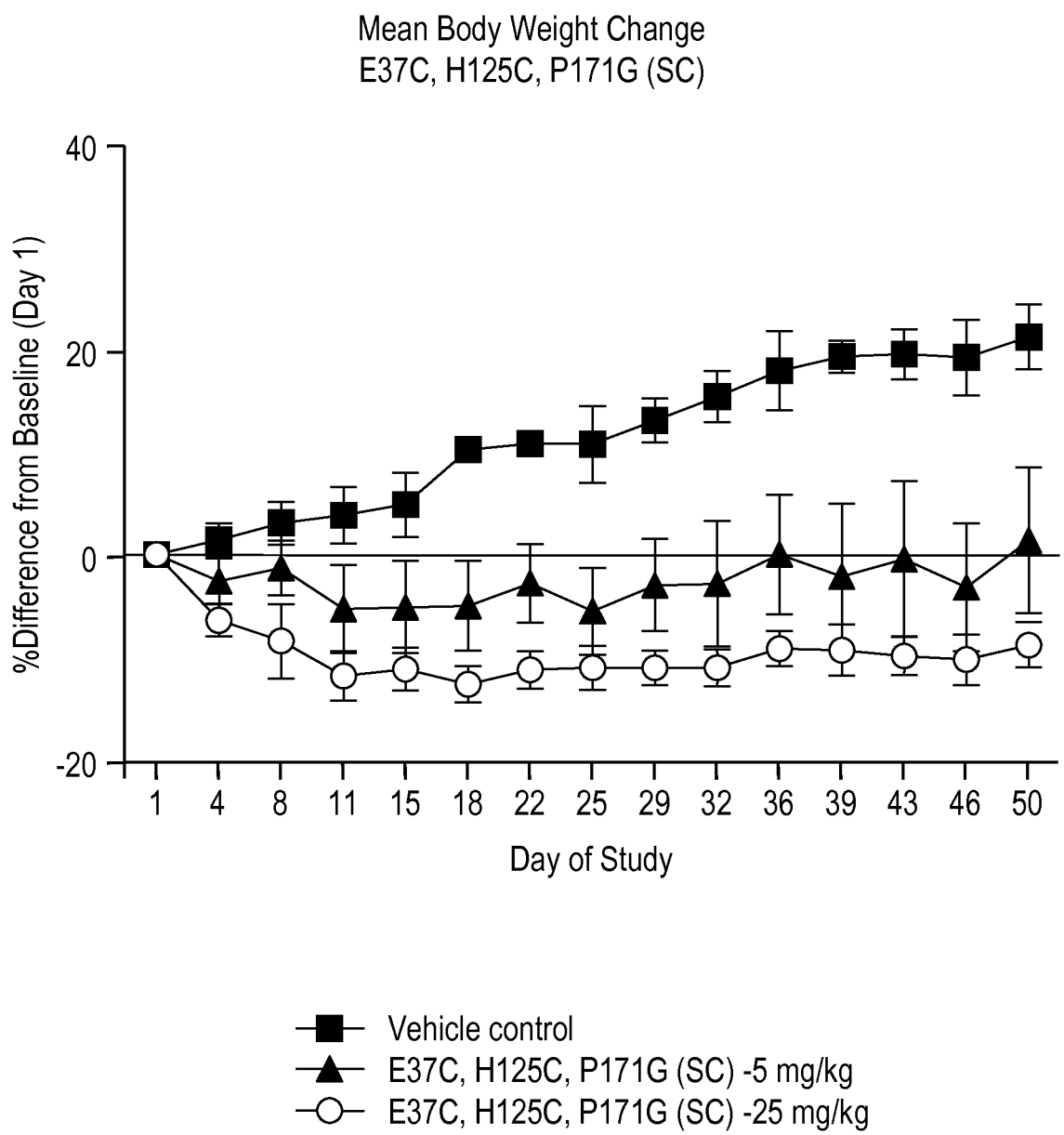

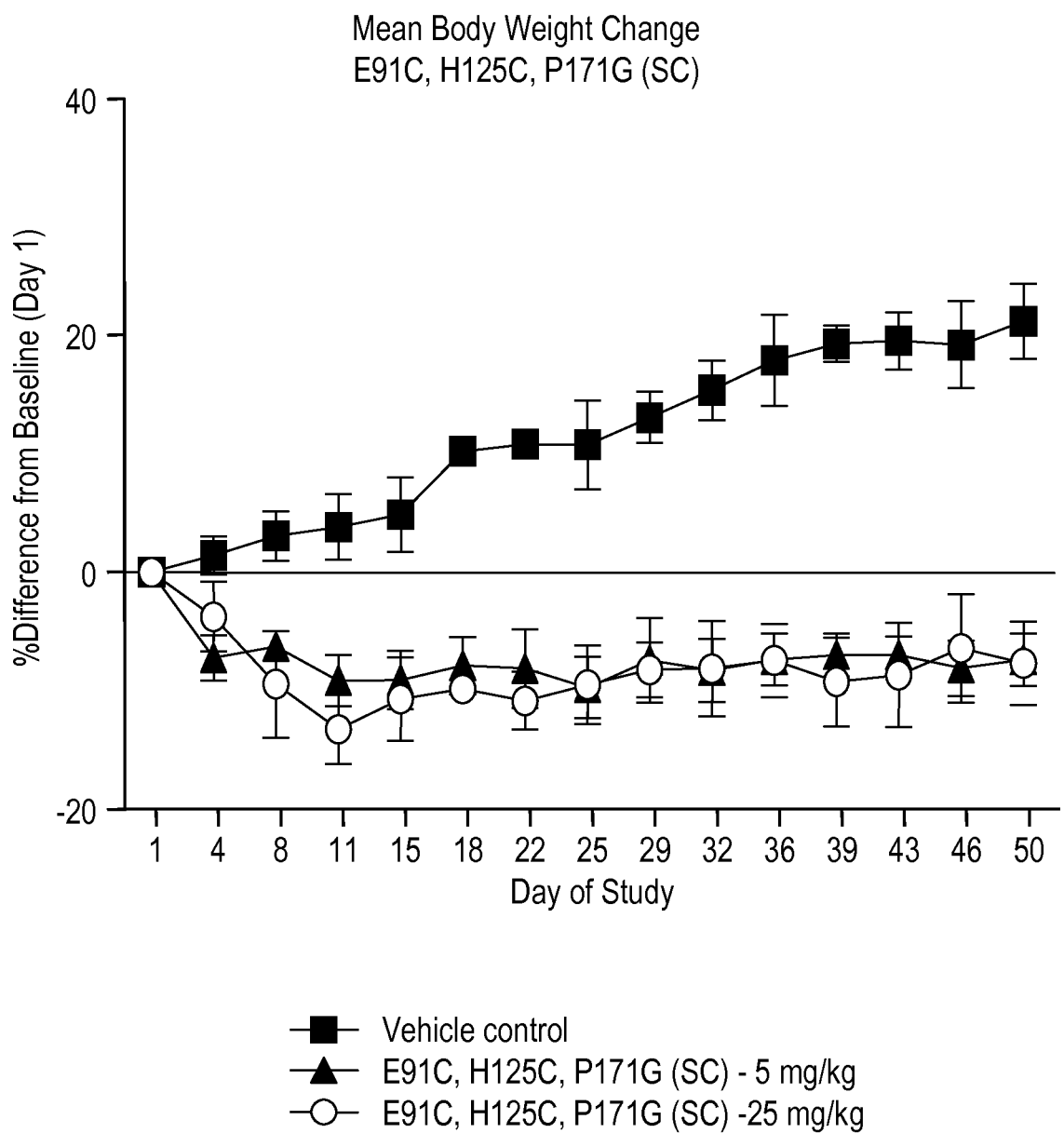

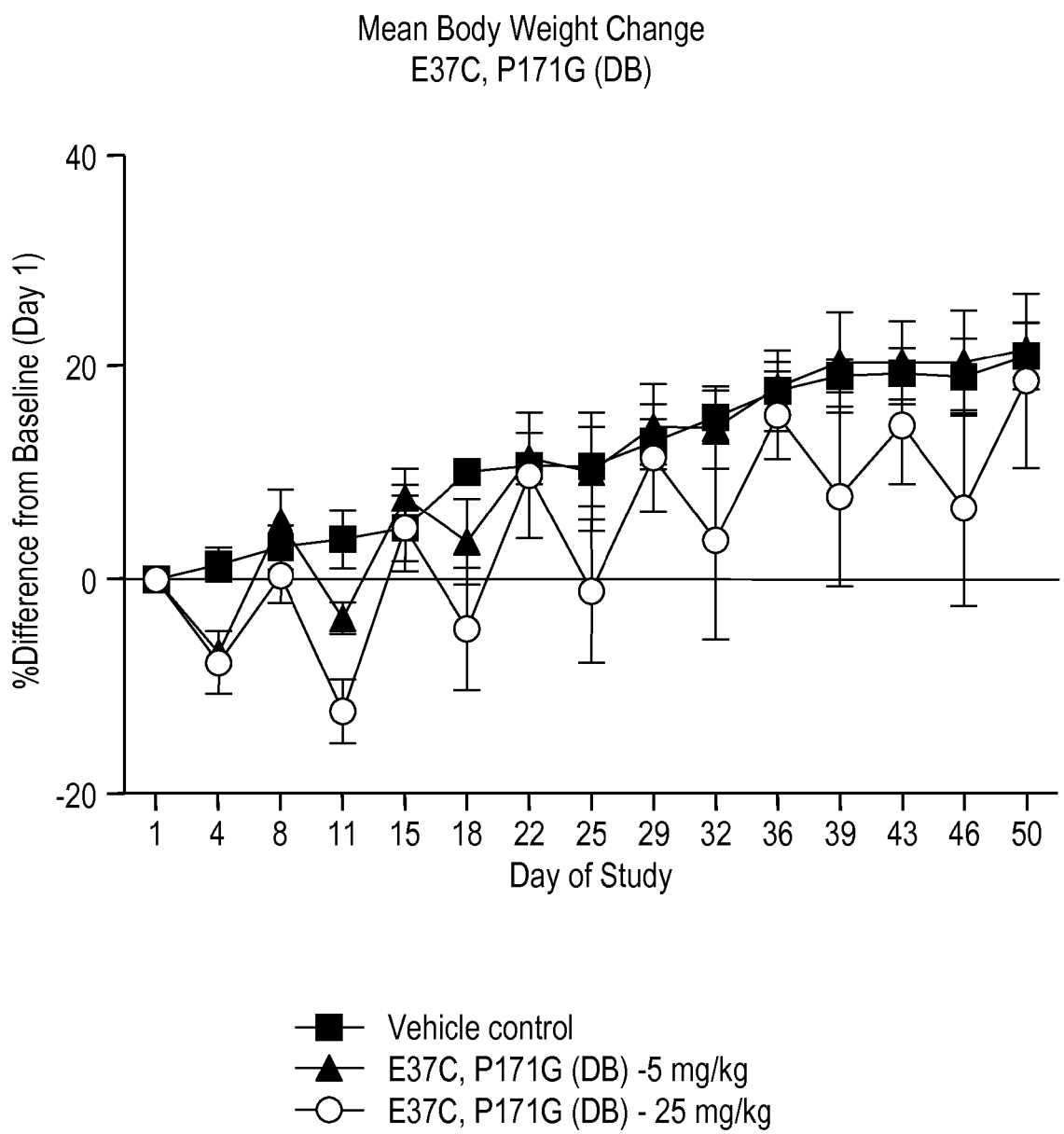

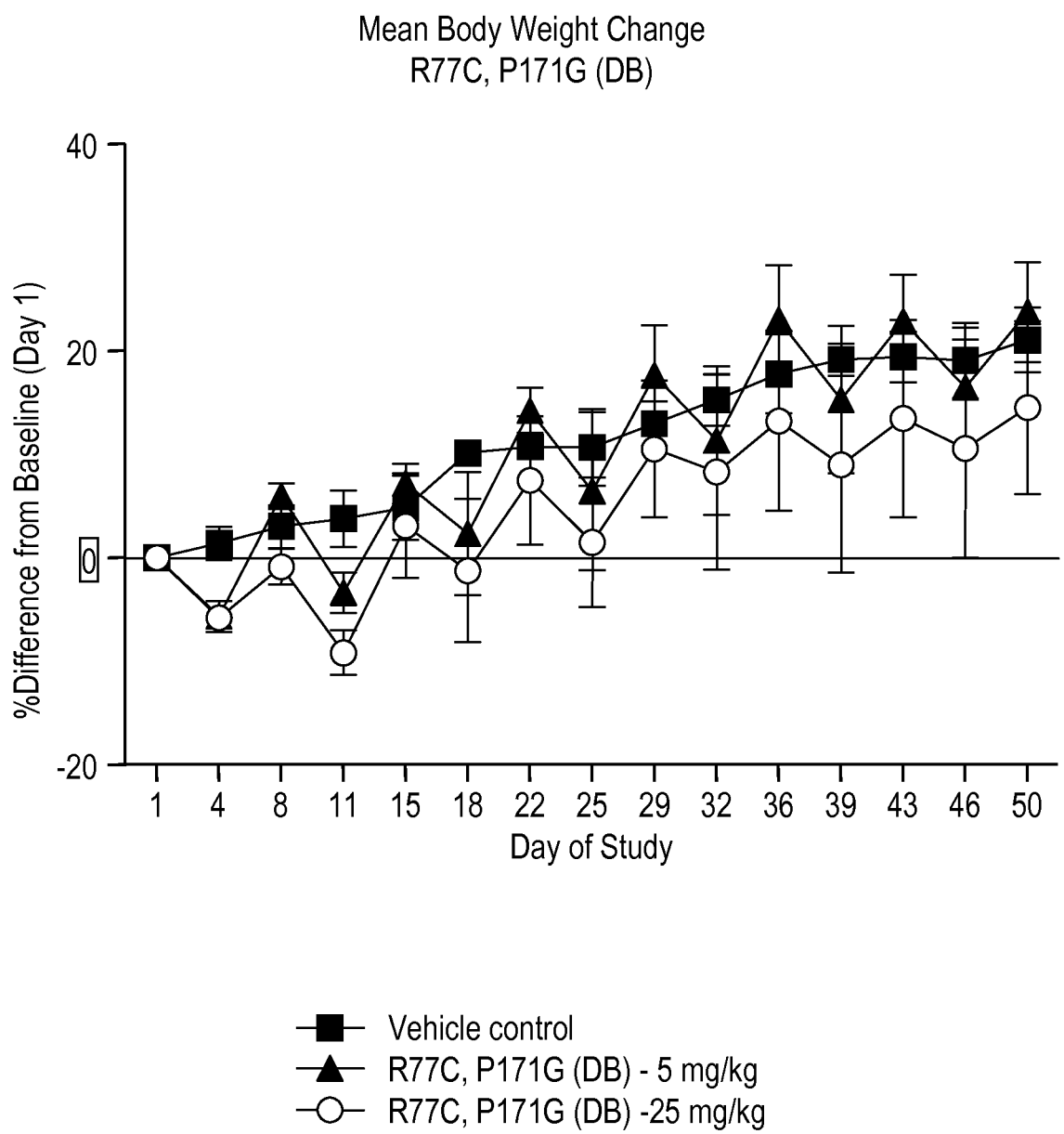

FGF-21 MUTANTS COMPRISING POLYETHYLENE GLYCOL AND USES THEREOF

CROSS-REFERENCE TO RELATED APPLICATION

This application claims the benefit of U.S. Provisional Application No. 61/195,761 filed Oct. 10, 2008.

BACKGROUND OF THE INVENTION

1. Field of the Invention

The invention relates to nucleic acid molecules encoding FGF21 mutant polypeptides, FGF21 mutant polypeptides, pharmaceutical compositions comprising FGF21 mutant polypeptides, and methods for treating metabolic disorders using such nucleic acids, polypeptides, or pharmaceutical compositions.

2. Background of the Invention

FGF21 is a secreted polypeptide that belongs to a subfamily of fibroblast growth factors (FGFs) that includes FGF19, FGF21, and FGF23 (Itoh et al., 2004, *Trend Genet.* 20: 563-69). FGF21 is an atypical FGF in that it is heparin independent and functions as a hormone in the regulation of glucose, lipid, and energy metabolism.

FGF21 was isolated from a liver cDNA library as a hepatic secreted factor. It is highly expressed in liver and pancreas and is the only member of the FGF family to be primarily expressed in liver. Transgenic mice overexpressing FGF21 exhibit metabolic phenotypes of slow growth rate, low plasma glucose and triglyceride levels, and an absence of age-associated type 2 diabetes, islet hyperplasia, and obesity. Pharmacological administration of recombinant FGF21 protein in diabetic rodent models results in normalized levels of plasma glucose, reduced triglyceride and cholesterol levels, and improved glucose tolerance and insulin sensitivity. In addition, FGF21 reduces body weight and body fat by increasing energy expenditure, physical activity, and metabolic rate. Experimental research provides support for the pharmacological administration of FGF21 for the treatment of type 2 diabetes, obesity, dyslipidemia, and other metabolic conditions or disorders in humans.

Human FGF21 has a short half-life in vivo. In mice and cynomolgus monkey, the effective half-life of human FGF21 is 1 to 2 hours. In developing an FGF21 protein for use as a therapeutic in the treatment of type 2 diabetes, an increase in half-life would be desirable. FGF21 proteins having an enhanced half-life would allow for less frequent dosing of patients being administered the protein.

SUMMARY OF THE INVENTION

In one embodiment, the present invention provides an isolated nucleic acid molecule comprising a nucleotide sequence encoding a polypeptide of SEQ ID NO: 4 having at least one amino acid substitution that is: (a) a lysine residue at one or more of positions 36, 72, 77, 126 and 175; (b) a cysteine residue at one or more of positions 37, 38, 46, 91, 69, 77, 79, 87, 91, 112, 113, 120, 121, 125, 126, 175, 170, and 179; (c) an arginine residue at one or more of positions 56, 59, 69, and 122; (d) a glycine residue at position 170; (e) a glycine residue at position 171; and combinations of (a)-(e).

In another embodiment, the present invention provides an isolated nucleic acid encoding a polypeptide comprising the amino acid sequence of SEQ ID NO: 4 having at least one amino acid substitution that is: (a) a lysine residue at one or more of positions 36, 72, 77, 126 and 175; (b) a cysteine residue at one or more of positions 37, 38, 46, 91, 69, 77, 79, 87, 91, 112, 113, 120, 121, 125, 126, 175, 170, and 179; (c) an arginine residue at one or more of positions 56, 59, 69, and 122; (d) a glycine residue at position 170; (e) a glycine residue at position 171; and combinations of (a)-(e), and which comprises additions, deletions or further substitutions that make the polypeptide at least 85% identical to SEQ ID NO:4, provided that the at least one amino acid substitution of claim 1(a)-(e) is not further modified.

The present invention also provides vectors and host cells comprising the nucleic acid molecules of the present invention.

In a further embodiment, the present invention provides an isolated polypeptide comprising the amino acid sequence of SEQ ID NO: 4 having at least one amino acid substitution that is: (a) a lysine residue at one or more of positions 36, 72, 77, 126 and 175; (b) a cysteine residue at one or more of positions 37, 38, 46, 91, 69, 77, 79, 87, 91, 112, 113, 120, 121, 125, 126, 175, 170, and 179; (c) an arginine residue at one or more of positions 56, 59, 69, and 122; (d) a glycine residue at position 170; (e) a glycine residue at position 171; and combinations of (a)-(e), In yet another embodiment, the present invention provides an isolated nucleic acid encoding a polypeptide comprising the amino acid sequence of SEQ ID NO: 4 having at least one amino acid substitution that is: (a) a lysine residue at one or more of positions 36, 72, 77, 126 and 175; (b) a cysteine residue at one or more of positions 37, 38, 46, 91, 69, 77, 79, 87, 91, 112, 113, 120, 121, 125, 126, 175, 170, and 179; (c) an arginine residue at one or more of positions 56, 59, 69, and 122; (d) a glycine residue at position 170; (e) a glycine residue at position 171; and combinations of (a)-(e), and which comprises additions, deletions or further substitutions that make the polypeptide at least 85% identical to SEQ ID NO:4, provided that the at least one amino acid substitution of claim 1(a)-(e) is not further modified.

In still another embodiment, the present invention provides an isolated polypeptide comprising the amino acid sequence of SEQ ID NO: 4 having at least one amino acid substitution that is: (a) a lysine residue at one or more of positions 36, 72, 77, 126 and 175; (b) a cysteine residue at one or more of positions 37, 38, 46, 91, 69, 77, 79, 87, 91, 112, 113, 120, 121, 125, 126, 175, 170, and 179; (c) an arginine residue at one or more of positions 56, 59, 69, and 122; (d) a glycine residue at position 170; (e) a glycine residue at position 171; and combinations of (a)-(e), and which comprises additions, deletions or further substitutions that make the polypeptide at least 85% identical to SEQ ID NO:4, provided that the at least one amino acid substitution of claim 1(a)-(e) is not further modified.

Additionally, the present invention provides a composition comprising a first polypeptide comprising the amino acid sequence of SEQ ID NO: 4 optionally having at least one amino acid substitution that is: (a) a lysine residue at one or more of positions 36, 72, 77, 126 and 175; (b) a cysteine residue at one or more of positions 37, 38, 46, 91, 69, 77, 79, 87, 91, 112, 113, 120, 121, 125, 126, 175, 170, and 179; (c) an arginine residue at one or more of positions 56, 59, 69, and 122; (d) a glycine residue at position 170; (e) a glycine residue at position 171; and combinations of (a)-(e), joined by a linker to a second polypeptide comprising a polypeptide comprising the amino acid sequence of SEQ ID NO: 4 optionally having at least one amino acid substitution that is: (a) a lysine residue at one or more of positions 36, 72, 77, 126 and 175; (b) a cysteine residue at one or more of positions 37, 38, 46, 91, 69, 77, 79, 87, 91, 112, 113, 120, 121, 125, 126, 175, 170, and 179; (c) an arginine residue at one or more of positions 56, 59, 69, and 122; (d) a glycine residue at position 170; (e) a glycine residue at position 171; and combinations of (a)-(e).

The present invention also provides chemically modified forms of the polypeptides of the present invention. The chemically modified forms of the polypeptides comprise a polymer attached to the N-terminus and/or a naturally or non-naturally occurring polymer attachment site. The present invention further provides pharmaceutical compositions and methods of treating metabolic disorders such as obesity and diabetes comprising administering the pharmaceutical compositions of the present invention to a patient in need thereof.

Specific embodiments of the present invention will become evident from the following more detailed description of certain embodiments and the claims.

BRIEF DESCRIPTION OF THE DRAWINGS

FIG. 4 comprises two plots depicting the results of an ELK-luciferase assay performed on FGF21 mutant polypeptides having a single engineered polymer attachment sites that have been chemically modified by the attachment of a 20 kDa methoxy PEG maleimide molecule, namely E37C, R77C, E91C, wild-type FGF21 and N-terminally PEGylated FGF21 (upper plot) and G113C, N121C, D46C, wild-type FGF21 and N-terminally PEGylated FGF21 (lower plot).

FIG. 5 comprises two plots depicting the results of an ELK-luciferase assay performed on FGF21 mutant polypeptides having a single engineered polymer attachment site, that have been chemically modified by the attachment of a 20 kDa methoxy-PEG maleimide, namely H125C, G120C, R126C, wild-type FGF21 and N-terminally PEGylated FGF21 (upper plot) and D79C, D38C, wild-type FGF21 and N-terminally PEGylated FGF21 (lower plot).

FIG. 6 comprises two plots depicting results of an ELK-luciferase assay performed on wild-type FGF21 and FGF21 mutant polypeptides having a single engineered polymer attachment site that has been chemically modified by the attachment of a 20 kDa methoxy PEG maleimide molecule, namely K69C, D79C, wild-type FGF21 and N-terminally PEGylated FGF21 (upper plot), and R175C, Y179C, wild-type FGF21 and N-terminally PEGylated FGF21 (lower plot).

FIG. 10 comprises two plots depicting the percent change in blood glucose levels in mice over a nine day period from time 0 after a single injection of PBS or N-terminally PEGylated FGF21 mutant polypeptides comprising the mutations R77C or R126K, which were further PEGylated at these introduced polymer attachment sites with 20 kDa methoxy PEG maleimide molecules and a fusion comprising an Fc molecule and a G170E FGF21 mutant polypeptide (upper plot); or an N-terminally PEGylated FGF21 mutant polypeptide comprising the mutations R77C, which was further PEGylated at this introduced polymer attachment site with 20 kDa methoxy PEG maleimide molecule, and P171G (lower plot).

FIG. 16 is a plot showing body weight change in mice from time 0 after a single injection of vehicle (10 mM potassium phosphate, 5% sorbitol, pH 8) or FGF21 mutant polypeptides which were dually PEGylated with 20 kDa methoxy PEG maleimide molecules at introduced polymer attachment sites, namely E37C/R77C, E91C/R175C, E37/H125C, E37C/ R77C/P171G, E91C/R77C/P171G and E37C/R125C/ P171G.

FIG. 19A-19F is a series of six plots showing the change in body weight of mice during an eight week kidney vacuole study using once weekly dosing of vehicle (squares), 5 mg/kg (triangles) and 25 mg/kg (open circles) PEGylated FGF21 molecules. Mice dosed with dual cysteine targeted PEG-FGF21 showed a sustained weight loss, while those dosed with Tethered Molecules showed primarily transient weight loss.

DETAILED DESCRIPTION OF THE INVENTION

Figure 1:
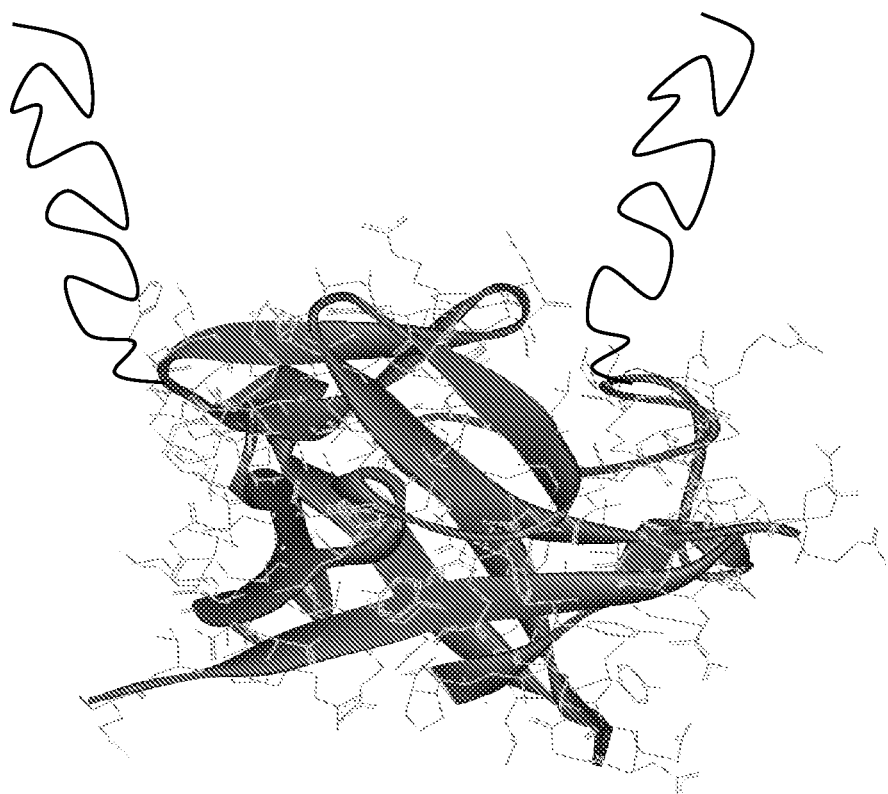
FIG. 1 is a cartoon depicting a FGF21 molecule having two polymers (e.g., PEG molecules) attached to the sequence.

A human FGF21 protein having enhanced properties such as an increased half-life can be prepared using the methods disclosed herein and standard molecular biology methods. It is known that by binding one or more water soluble polymers, such as PEG molecules, to a protein the half life of the protein can be extended. Thus, in various embodiments, the half life of native FGF21 can be extended by introducing amino acid substitutions into the protein to form points at which a polymer can be attached to the FGF21 protein. Such modified proteins are referred to herein as FGF21 mutants and form embodiments of the present invention. Polymers can also be introduced at the N-terminus of the FGF21 molecule in conjunction with the introduction of a non-naturally occurring polymer attachment site.

Recombinant nucleic acid methods used herein, including in the Examples, are generally those set forth in Sambrook et al., *Molecular Cloning: A Laboratory Manual* (Cold Spring Harbor Laboratory Press, 1989) or *Current Protocols in Molecular Biology* (Ausubel et al., eds., Green Publishers Inc. and Wiley and Sons 1994), both of which are incorporated herein by reference for any purpose.

1. General Definitions

As used herein, the term "a" means one or more unless specifically indicated otherwise.

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecules or other contaminants that are found in its natural environment that would interfere with its use in polypeptide production or its therapeutic, diagnostic, prophylactic or research use.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "naturally occurring" when used in connection with biological materials such as nucleic acid molecules, polypeptides, host cells, and the like, refers to materials which are found in nature and are not manipulated by man. Similarly, "non-naturally occurring" as used herein refers to a material that is not found in nature or that has been structurally modified or synthesized by man. When used in connection with nucleotides, the term "naturally occurring" refers to the bases adenine (A), cytosine (C), guanine (G), thymine (T), and uracil (U). When used in connection with amino acids, the term "naturally occurring" refers to the 20 amino acids alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y).

The term "FGF21 polypeptide" refers to any naturally occurring wild-type polypeptide expressed in humans. For purposes of this application, the term "FGF21 polypeptide" can be used interchangeably to refer to the full-length FGF21 polypeptide, which consists of 209 amino acid residues (SEQ ID NO: 2) and which is encoded by the nucleotide sequence of SEQ ID NO: 1; and the mature form of the polypeptide, which consists of 181 amino acid residues (SEQ ID NO: 4), which is encoded by the nucleotide sequence of SEQ ID NO: 3, and in which the 28 amino acid residues at the amino-terminal end of the full-length FGF21 polypeptide (i.e., which constitute the signal peptide) have been removed. An FGF21 polypeptide can be expressed with or without an N-terminal Methionine residue; as noted herein, an N-terminal Methionine residue can be added by design or as a function of a bacterial expression system.

The term "biologically active," as applied to an FGF21 polypeptide, including FGF21 mutant polypeptides described herein, refers to a naturally occurring activity of a wild-type FGF21 polypeptide, such as the ability to lower blood glucose, insulin, triglyceride, or cholesterol; reduce body weight; and improve glucose tolerance, energy expenditure, or insulin sensitivity. As applied to a FGF21 mutant polypeptide, the term is not dependent on the type or number of modifications that have been introduced into the FGF21 mutant polypeptide. For example, some FGF21 mutant polypeptides possess a somewhat decreased level of FGF21 activity relative to the wild-type FGF21 polypeptide but are nonetheless be considered to be biologically active FGF21 mutant polypeptides. Differences in the activity of a particular FGF21 mutant polypeptide may be observed between in vivo and in vitro assays; any such differences are related to the particular assays used. Such an observation, however, does not affect the meaning of the term "biologically active," and FGF21 mutant polypeptides showing a naturally occurring activity of a wild-type FGF21 polypeptide, such as the ability to lower blood glucose, insulin, triglyceride, or cholesterol; reduce body weight; and improve glucose tolerance, energy expenditure, or insulin sensitivity, in any in vivo or in vitro assay are "biologically active."

The terms "effective amount" and "therapeutically effective amount" are used interchangeably and refer to the amount of an FGF21 mutant polypeptide used to support an observable level of one or more biological activities of the wild-type FGF21 polypeptide, such as the ability to lower blood glucose, insulin, triglyceride, or cholesterol levels; reduce body weight; or improve glucose tolerance, energy expenditure, or insulin sensitivity.

The term "pharmaceutically acceptable carrier" or "physiologically acceptable carrier" as used herein refers to one or more formulation materials suitable for accomplishing or enhancing the delivery of an FGF21 mutant polypeptide. Examples of such materials can be found in *Remington*, supra, incorporated herein by reference.

The term "Tethered Molecule" refers to a construct comprising two or more FGF21 molecules tethered together by a linker molecule. A Tethered Molecule comprises at least two FGF21 polypeptides, at least one of which is an FGF21 mutant polypeptide as described herein, but can comprise three, four or more FGF21 or FGF21 mutant polypeptides joined together by linkers. Thus, the term Tethered Molecule is not restricted to a molecule comprising combinations of only one or two FGF21 or FGF21 mutant polypeptides.

The term "polymer attachment site" refers to a region of the primary amino acid sequence of a polypeptide (e.g., an FGF21 polypeptide) that is chemically adaptable to covalent association with a polymer (e.g., PEG molecules of all molecular weights, polymeric mannose, glycans, etc). A polymer attachment site can mean a single amino acid (e.g., cysteine, lysine, arginine or a suitable non-naturally occurring amino acid) or the term can refer to two or more amino acids that are adjacent to each other either in sequence or in space.

The term "chemically modified," when used in relation to a FGF21 wild-type or FGF21 mutant polypeptide as disclosed herein, refers to a FGF21 polypeptide that has been modified from its naturally occurring state by the covalent attachment of one or more heterologous molecules. Examples of heterologous molecules include polyethylene glycol (PEG), monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, hydroxyl ethyl starch (HES), and polyvinyl alcohol. Examples of chemically modified FGF21 polypeptides include PEGylated wild-type FGF21 and FGF21 mutant polypeptides.

2. FGF21 Mutant Polypeptides

In various aspects, the present invention discloses a series of methods for the site-directed PEGylation of FGF21 and FGF21 mutant polypeptides, which can enhance the pharmacokinetic properties of the FGF21 molecule while minimizing the impact on the in vitro activity. The enhanced pharmacokinetic profile of these PEGylated FGF21 molecules has an impact on the in vivo efficacy of the molecule by increasing exposure to the therapeutic agent. In addition, the strategies described herein are compatible with creating multiple PEGylation sites, which may both further enhance the pharmacokinetic properties of the molecule, and lower their vacuole-forming potential. Two principle strategies were employed to accomplish this, as described herein.

In one aspect, the present invention relates to FGF21 sequences into which one or more modifications have been introduced. Thus, the terms "FGF21 mutant polypeptide" and "FGF21 mutant," which can be used interchangeably, refer to an FGF21 polypeptide in which a wild-type FGF21 amino acid sequence (e.g., SEQ ID NOs 2 or 4) has been modified. Such modifications include, but are not limited to, one or more amino acid substitutions, including substitutions with non-naturally occurring amino acid analogs, insertions and truncations. Thus, FGF21 polypeptide mutants include, but are not limited to, site-directed FGF21 mutants, such as those introducing a non-naturally occurring polymer attachment site, or which impart a degree of resistance to proteolysis, as described herein. For the purpose of identifying the specific amino acid substitutions of the FGF21 mutants of the present invention, the numbering of the amino acid residues truncated or mutated corresponds to that of the mature 181-residue FGF21 polypeptide (i.e., the N terminus of the sequence begins HPIPD, and these residues are designated as residues 1, 2, 3, 4 and 5, respectively). An N-terminal methionine residue can but does not need to be present; this N-terminal methionine residue is not included in the numbering scheme of the protein.

As stated, FGF21 mutants, including truncated forms of FGF21 comprising one or more substitutions or insertions, which comprise non-naturally occurring amino acids form an embodiment of the present invention. Such insertions or substitutions can impart various properties, including acting as sites for polymer attachment. In such cases, non-naturally occurring amino acids can be incorporated into an FGF21 sequence in addition to the various mutations described herein. Accordingly, an FGF21 mutant can comprise one or more of the mutations described herein and can further comprise one or more non-naturally occurring amino acids. A non-limiting lists of examples of non-naturally occurring amino acids that can be inserted into an FGF21 sequence or substituted for a wild-type residue in an FGF21 sequence include β-amino acids, homoamino acids, cyclic amino acids and amino acids with derivatized side chains. Examples include (in the L-form or D-form; abbreviated as in parentheses): para-acetyl-phenylalanine, para-azido-phenylalanine, para-bromo-phenylalanine, para-iodo-phenylalanine and para-ethynyl-phenylalanine, citrulline (Cit), homocitrulline (hCit), Nα-methylcitrulline (NMeCit), Nα-methylhomocitrulline (Nα-MeHoCit), ornithine (Orn), Nα-Methylornithine (Nα-MeOrn or NMeOrn), sarcosine (Sar), homolysine (hLys or hK), homoarginine (hArg or hR), homoglutamine (hQ), Nα-methylarginine (NMeR), Nα-methylleucine (Nα-MeL or NMeL), N-methylhomolysine (NMeHoK), Nα-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl)alanine (1-Nal), 3-(2-naphthyl)alanine (2-Nal), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), glycyllysine (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α,β-diaminopropionoic acid (Dpr), α,γ-diaminobutyric acid (Dab), diaminopropionic acid (Dap), cyclohexylalanine (Cha), 4-methyl-phenylalanine (MePhe), β,β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, 4-Amino-O-Phthalic Acid (4APA), and other similar amino acids, and derivatized forms of any of those specifically listed.

In other embodiments of the present invention, an FGF21 mutant polypeptide comprises an amino acid sequence that is at least about 85 percent identical to a wild-type FGF21 amino acid sequence (e.g., SEQ ID NOs: 2 or 4), but wherein the specific residues introducing non-naturally occurring polymer attachment sites in the FGF21 mutant polypeptide have not been further modified. In other words, with the exception of residues in the FGF21 mutant sequence that have been modified in order to introduce a non-naturally occurring polymer attachment site or a mutation to increase resistance to proteolysis, about 15 percent of all other amino acid residues in the FGF21 mutant sequence may be modified. For example, in the FGF21 mutant polypeptide G170C, up to 15 percent of all amino acid residues other than the glycine residue at position 170 could be modified. In still other embodiments, an FGF21 polypeptide mutant comprises an amino acid sequence that is at least about 90 percent, or about 95, 96, 97, 98, or 99 percent identical to a wild-type FGF21 amino acid sequence (e.g., SEQ ID NO: 2, 4, 6 or 8), but wherein the specific residues that have been modified to introduce a non-naturally occurring polymer attachment site or enhance proteolysis resistance have not been further modified. Such FGF21 mutant polypeptides possess at least one activity of the wild-type FGF21 polypeptide.

FGF21 mutant polypeptides can be generated by introducing amino acid substitutions, either conservative or non-conservative in nature and using naturally or non-naturally occurring amino acids, at particular positions of the FGF21 polypeptide. Such substitutions can be made in addition to substitutions designed or observed to impart a desirable property to the FGF21 polypeptide. By way of example, a FGF21 mutant polypeptide can comprise a substitution designed to achieve a desirable property, such as introducing a non-naturally occurring polymer attachment site or enhancing resistance to proteolysis, and can further comprise one or more conservative or non-conservative substitutions which may, but need not, maintain the biological activity of the wild-type FGF21 polypeptide.

FGF21 mutations can be conservative or non-conservative. A "conservative amino acid substitution" can involve a substitution of a native amino acid residue (i.e., a residue found in a given position of the wild-type FGF21 polypeptide sequence) with a normative residue (i.e., a residue that is not found in a given position of the wild-type FGF21 polypeptide sequence) such that there is little or no effect on the polarity or charge of the amino acid residue at that position. Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues can be divided into classes based on common side chain properties:
(1) hydrophobic: norleucine, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

Conservative substitutions can involve the exchange of a member of one of these classes for another member of the same class. Non-conservative substitutions can involve the exchange of a member of one of these classes for a member from another class.

Desired amino acid substitutions (whether conservative or non-conservative) can be determined by those skilled in the art at the time such substitutions are desired. An exemplary (but not limiting) list of amino acid substitutions is set forth in Table 1.

TABLE 1

Amino Acid Substitutions

| Original Residue | Exemplary Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

2.A. FGF21 Mutant Polypeptides Comprising a Proteolysis-Resistant Mutation

It has been determined that the mature form of FGF21 (i.e., the 181 residue form) undergoes in vivo degradation, which was ultimately determined to arise from proteolytic attack. The in vivo degradation of mature FGF21 has been found to lead to a shorter effective half-life, which can adversely affect the therapeutic potential of the molecule. Accordingly, a directed study was performed to identify FGF21 mutants that exhibit a resistance to proteolysis. As a result of this investigation, the sites in the mature FGF21 polypeptide that were determined to be particularly susceptible to proteolysis include the peptide bond between the amino acid residues at positions 4-5, 20-21, 151-152, and 171-172.

A non-limiting list of exemplary substitutions that eliminate the proteolytic effect observed in mature FGF21 while not affecting the biological activity of the protein to an unacceptable degree that can be employed in the present invention is presented in Table 2. Table 2 is demonstrative only and other proteolysis resistant substitutions can be identified and employed in the present invention. These proteolysis-resistant substitutions can be made in addition to substitutions that introduce one or more non-naturally occurring polymer attachment sites, thus generating a FGF21 mutant polypeptide exhibiting the desirable characteristics imparted by each type of mutation.

TABLE 2

Representative Substitutions that Provide Proteolysis Resistance

| Amino Acid Position | Native Residue | Mutations |
| --- | --- | --- |
| 19 | Arg | Gln, Ile, Lys |
| 20 | Tyr | His, Leu, Phe |
| 21 | Leu | Ile, Phe, Tyr, Val |
| 22 | Tyr | Ile, Phe, Val |
| 150 | Pro | Ala, Arg |
| 151 | Gly | Ala, Val |
| 152 | Ile | His, Leu, Phe, Val |
| 170 | Gly | Ala, Asn, Asp, Cys, Gln, Glu, Pro, Ser |
| 171 | Pro | Ala, Arg, Asn, Asp, Cys, Glu, Gln, Gly, His, Lys, Ser, Thr, Trp, Tyr |
| 172 | Ser | Leu, Thr |
| 173 | Gln | Arg, Glu |

Preferably, but not necessarily, FGF21 mutant polypeptides comprising a proteolysis-resistant mutation have biological activity essentially the same as, or greater than, the activity of wild-type FGF21. Therefore, another embodiment of the present invention is directed to FGF21 mutant polypeptides that comprise one or more non-naturally occurring polymer attachment sites and are resistant to proteolysis, yet still retain biological activity that is the same as, or greater than, wild-type FGF21. Although less desirable in some cases, FGF21 mutants that comprise one or more non-naturally occurring polymer attachment sites and are resistant to proteolysis but exhibit somewhat decreased biological activity form another embodiment of the present invention. In some cases it can be desirable to maintain a degree of proteolysis, and consequently, FGF21 mutants comprising one or more non-naturally occurring polymer attachment sites and which are resistant to proteolysis and yet still allow some degree of proteolysis to occur also form another embodiment of the present invention.

As with all FGF21 mutant polypeptides of the present invention, proteolysis-resistant FGF21 mutant polypeptides comprising one or more non-naturally occurring polymer attachment sites can be prepared as described herein. Those of ordinary skill in the art, for example, those familiar with standard molecular biology techniques, can employ that knowledge, coupled with the instant disclosure, to make and use the proteolysis-resistant FGF21 mutants comprising one or more non-naturally occurring polymer attachment sites of the present invention. Standard techniques can be used for recombinant DNA, oligonucleotide synthesis, tissue culture, and transformation (e.g., electroporation, lipofection). See, e.g., Sambrook et al., *Molecular Cloning: A Laboratory Manual*, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses; chemical analyses; pharmaceutical preparation, formulation, and delivery; and treatment of patients.

Proteolysis-resistant FGF21 mutants comprising one or more non-naturally occurring polymer attachment sites which are resistant to proteolysis can be chemically modified using methodology known in the art and described herein. Chemically modifying (e.g., PEGylating) a proteolysis-resistant FGF21 mutant polypeptide comprising one or more non-naturally occurring polymer attachment sites can generate molecules that exhibit both proteolysis resistance and desirable pharmacokinetic and pharmacodynamic properties.

2.B. FGF21 Mutant Polypeptides Comprising a Non-Naturally Occurring Polymer Attachment Site In various aspects of the present invention, FGF21 mutant polypeptides are disclosed. In another aspect, the FGF21 mutant polypeptides of the present invention include FGF21 polypeptides into which a non-naturally occurring polymer (e.g., PEGylation) attachment site(s) has been introduced. In yet another aspect of the present invention, truncated forms of FGF21 mutant polypeptides into which a non-naturally occurring polymer (e.g., PEG) attachment site(s) has been introduced are disclosed. FGF21 mutant polypeptides comprising a non-naturally occurring polymer attachment site and one or more conservative or non-conservative substitutions, which may but need not maintain the biological activity of the wild-type FGF21, form another aspect of the invention. The various FGF21 polypeptide mutants of the present invention can be prepared as described herein and in references provided herein.

In one embodiment, FGF21 polypeptide mutants of the present invention are modified by introducing a non-naturally occurring polymer attachment site. Indeed, in one aspect this is a goal of the FGF21 mutants of the present invention, namely the introduction of one or more non-naturally occurring polymer attachment sites such that half life-extending polymers can be attached to the FGF21 polypeptide mutant at desired locations. The polymer selected is typically, but not necessarily, water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable, such as PEG of a suitable molecular weight. Non-water soluble polymers, such as PEG fatty acid block copolymers can also be conjugated to FGF21 polypeptide mutants of the present invention and forms an aspect of the invention.

The activity of the FGF21 mutant polypeptides of the present invention can be assayed in a variety of ways, for example, using an in vitro ELK-luciferase assay as described herein in Example 10.

The activity of the FGF21 mutant polypeptides of the present invention can also be assessed in an in vivo assay, such as with ob/ob mice as shown in Example 12. Generally, to assess the in vivo activity of one or more of these polypeptides, the polypeptide can be administered to a test animal intraperitoneally. After one or more desired time periods, a blood sample can be drawn, and blood glucose levels can be measured.

As with all FGF21 mutant polypeptides of the present invention, these polypeptides can optionally comprise an amino-terminal methionine residue, which can be introduced by directed mutation or as a result of a bacterial expression process.

The FGF21 mutant polypeptides of the present invention can be prepared as described in Example 7. Those of ordinary skill in the art, familiar with standard molecular biology techniques, can employ that knowledge, coupled with the instant disclosure, to make and use the FGF21 mutant polypeptides of the present invention. Standard techniques can be used for recombinant DNA, oligonucleotide synthesis, tissue culture, and transformation (e.g., electroporation, lipofection). See, e.g., Sambrook et al., *Molecular Cloning: A Laboratory Manual*, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses; chemical analyses; pharmaceutical preparation, formulation, and delivery; and treatment of patients.

Following the preparation of a FGF21 mutant polypeptide, the polypeptide can be chemically modified by the attachment of a polymer, as described herein in Example 9.

3. Truncated FGF21 Mutant Polypeptides Comprising a Non-Naturally Occurring Polymer Attachment Site One embodiment of the present invention is directed to truncated forms of a mutant FGF21 polypeptide comprising one or more non-naturally occurring polymer attachment sites. Such truncated mutant polypeptides can, but need not, be chemically modified.

As used herein, the term "truncated FGF21 mutant polypeptide" refers to an FGF21 mutant polypeptide or chemically modified FGF21 mutant polypeptide in which one or more amino acid residues have been removed from the amino-terminal (or N-terminal) end of the FGF21 polypeptide, one or more amino acid residues have been removed from the carboxyl-terminal (or C-terminal) end of the FGF21 mutant polypeptide or chemically modified FGF21 polypeptide, or one or more amino acid residues have been removed from both the N-terminal and C-terminal ends of the FGF21 mutant polypeptide or chemically modified FGF21 polypeptide.

The activity of N-terminally truncated mutant FGF21, C-terminally truncated mutant FGF21 and mutant FGF21 molecules truncated at both the N- and C-terminal ends of the molecule, as well as chemically modified forms of these mutants, can be assayed in a variety of ways, for example, using an in vitro ELK-luciferase assay as described herein in Example 10.

The activity of the truncated mutant FGF21 polypeptides and chemically modified truncated mutant FGF21 polypeptides of the present invention can also be assessed in an in vivo assay, such as with ob/ob mice as shown in Example 12. Generally, to assess the in vivo activity of one or more of these polypeptides, the polypeptide can be administered to a test animal intraperitoneally. After one or more desired time periods, a blood sample can be drawn, and blood glucose levels can be measured.

As with all FGF21 mutants of the present invention, truncated mutant FGF21 and chemically modified truncated mutant FGF21 polypeptides can optionally comprise an amino-terminal methionine residue, which can be introduced by directed mutation or as a result of a bacterial expression process.

The truncated FGF21 mutant polypeptides of the present invention can be prepared as described in Examples 7. Those of ordinary skill in the art, familiar with standard molecular biology techniques, can employ that knowledge, coupled with the instant disclosure, to make and use the truncated mutant FGF21 polypeptides of the present invention. Standard techniques can be used for recombinant DNA, oligonucleotide synthesis, tissue culture, and transformation (e.g., electroporation, lipofection). See, e.g., Sambrook et al., *Molecular Cloning: A Laboratory Manual*, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses; chemical analyses; pharmaceutical preparation, formulation, and delivery; and treatment of patients.

Following the preparation of a truncated mutant FGF21 polypeptide, the polypeptide can be chemically modified by the attachment of a polymer, as described in Example 9.

4. Capped and C-terminal FGF21 Mutant Polypeptides

In another embodiment, the present invention is directed to mutant FGF21 polypeptides comprising one or more non-naturally occurring polymer attachment sites which have been capped by the addition of another one or more residues to the C-terminus of the polypeptide, extending the amino acid sequence beyond that of the wild-type protein. In yet another embodiment, the present invention is directed to FGF21 mutant polypeptides comprising one or more non-naturally occurring polymer attachments sites that further comprise one or more C-terminal mutations. Such capped and C-terminally mutated FGF21 mutant polypeptides can, but need not, be chemically modified.

As used herein, the term "capped FGF21 mutant polypeptide" refers to an FGF21 mutant polypeptide or chemically modified FGF21 mutant polypeptide in which one or more amino acid residues have been added to the C terminus of the FGF21 mutant polypeptide or chemically modified FGF21 mutant polypeptide. Any naturally or non-naturally occurring amino acid can be used to cap an FGF21 mutant polypeptide, including one or more proline residues and one or more glycine residues. Although the wild-type FGF21 sequence is only 181 residues long, a capped FGF21 mutant polypeptide extends the length of the polypeptide one residue for each added capping residue; consistent with the numbering scheme of the present disclosure, cap residues are numbered beginning with 182. Thus, a single proline capping residue is indicated as P182. Longer caps are possible and are numbered accordingly (e.g., X182, Y183, Z184, where X, Y and Z are any naturally or non-naturally occurring amino acid). Capping residues can be added to a mutant FGF21 polypeptide using any convenient method, such as chemically, in which an amino acid is covalently attached to the C-terminus of the polypeptide by a chemical reaction. Alternatively, a codon encoding a capping residue can be added to the FGF21 mutant polypeptide coding sequence using standard molecular biology techniques. Any of the mutant FGF21 polypeptides described herein can be capped with one or more residues, as desired.

C-terminal mutations form another aspect of the present invention. As used herein, the term "C-terminal mutation" refers to one or more changes in the region of residues 91-181 (or longer if the polypeptide is capped) of a mutant FGF21 polypeptide. A C-terminal mutation introduced into a FGF21 mutant polypeptide sequence will be in addition to one or more mutations which introduce a non-naturally occurring polymer attachment site. Although C-terminal mutations can be introduced at any point in the region of 91-181 of the FGF21 mutant polypeptide sequence, exemplary positions for C-terminal mutations include positions 171, 172, 173, 174, 175, 176, 177, 178, 179, 180 and 181. C-terminal mutations can be introduced using standard molecular biological techniques, such as those described herein. Any of the mutant FGF21 polypeptides described herein can comprise a C-terminal mutation.

Examples of positions and identities for capped and/or C-terminally mutations are shown in Table 3:

TABLE 3

Examples of Capping Positions and/or C-terminally Mutations

E37C, R77C, P171G, P182
P171G, S181P, P182
P171G, S181P
P171G, S181T
P171G, S181G
P171G, S181A
P171G, S181L
P171G, A180P
P171G, A180G
P171G, A180S
P171G, Y179P
P171G, Y179G
P171G, Y179S
P171G, Y179A
P171G, L182
P171G, G182
P171G, P182
P171G, G182, G183
P171G, G182, G183, G184, G185, G186

The activity of capped and/or C-terminally mutated FGF21 mutant polypeptides, as well as chemically modified forms of these mutants, can be assayed in a variety of ways, for example, using an in vitro ELK-luciferase assay as described herein in Example 10.

The activity of the capped and/or C-terminally mutated FGF21 mutant polypeptides, and chemically modified capped and/or C-terminally mutated FGF21 mutant polypeptides, of the present invention can also be assessed in an in vivo assay, such as ob/ob mice as shown in Example 12. Generally, to assess the in vivo activity of one or more of these polypeptides, the polypeptide can be administered to a test animal intraperitoneally. After one or more desired time periods, a blood sample can be drawn, and blood glucose levels can be measured.

As with all FGF21 mutants of the present invention, capped and/or C-terminally mutated FGF21 mutant polypeptides, and chemically modified capped and/or C terminally mutated FGF21 mutant polypeptides, can optionally comprise an amino-terminal methionine residue, which can be introduced by directed mutation or as a result of a bacterial expression process.

The capped and/or C-terminally mutated FGF21 mutant polypeptides of the present invention can be prepared as described in Example 7. Those of ordinary skill in the art, familiar with standard molecular biology techniques, can employ that knowledge, coupled with the instant disclosure, to make and use the capped and/or C-terminally mutated FGF21 mutant polypeptides of the present invention. Standard techniques can be used for recombinant DNA, oligonucleotide synthesis, tissue culture, and transformation (e.g., electroporation, lipofection). See, e.g., Sambrook et al., *Molecular Cloning: A Laboratory Manual*, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses; chemical analyses; pharmaceutical preparation, formulation, and delivery; and treatment of patients.

Following the preparation of a capped and/or C terminally mutated FGF21 mutant polypeptide, the polypeptide can be chemically modified by the attachment of a polymer, as described in Example 9.

5. FGF21 Mutant Polypeptides Containing No Naturally Occurring Cysteine Residues In a further aspect of the present invention, FGF21 mutant polypeptides can be prepared in which both cysteine residues in the wild-type FGF21 polypeptide sequence are replaced with residues that do not form disulfide bonds and do not serve as polymer attachment sites, such as alanine or serine. Subsequently, substitutions can be made in the FGF21 mutant polypeptide sequence that introduce non-naturally occurring polymer attachment sites, in the form of thiol-containing residues (e.g., cysteine residues or non-naturally occurring amino acids having thiol groups) or free amino groups (e.g., lysine or arginine residues or non-naturally occurring amino acids having free amino groups). Polymers that rely on thiol or free amino groups for attachment, such as PEG, can then be targeted to cysteine, lysine or arginine residues that have been introduced into the FGF21 mutant polypeptide sequence at known positions. This strategy can facilitate more efficient and controlled polymer placement.

In one approach, the two naturally occurring cysteine residues in the wild-type FGF21 polypeptide, which are located at positions 75 and 93, can be substituted with non-thiol containing residues. Subsequently, a cysteine residue can be introduced at a known location. The FGF21 mutant polypeptide can also comprise other mutations, which can introduce still more polymer attachments sites (e.g., cysteine residues)

or can be designed to achieve some other desired property. Examples of such FGF21 mutant polypeptides include C75A/E91C/C93A/H125C/P171G and C75S/E91C/C93S/H125C/P171G. In these examples, the naturally occurring cysteines at positions 75 and 93 have been mutated to alanine or serine residues, polymer attachment sites have been introduced at positions 91 and 125 (in this case for a thiol-reactive polymer such as PEG) and an additional mutation has been made at position 171, namely the substitution of proline 171 with a glycine residue.

Like all of the FGF21 mutant polypeptides disclosed herein, the activity of FGF21 mutant polypeptides which contain neither of the cysteines found in the wild-type FGF21 polypeptide sequence but instead comprise an introduced polymer attachment site and optionally one or more additional mutations, as well as chemically modified forms of these mutants, can be assayed in a variety of ways, for example, using an in vitro ELK-luciferase assay as described herein in Example 10. The in vivo activity of these polypeptides can be assessed in an in vivo assay, such as with ob/ob mice as shown in Example 12 and as described herein As with all FGF21 mutants of the present invention, the activity of FGF21 mutant polypeptides which contain neither of the cysteines found in the wild-type FGF21 polypeptide sequence but instead comprise an introduced polymer attachment site and optionally one or more additional mutations and chemically modified forms of these FGF21 mutant polypeptides can optionally comprise an amino-terminal methionine residue, which can be introduced by directed mutation or as a result of a bacterial expression process.

FGF21 mutant polypeptides which contain neither of the cysteines found in the wild-type FGF21 polypeptide sequence but instead comprise an introduced polymer attachment site and optionally one or more additional mutations can be prepared as described herein, for example in Example 7. Those of ordinary skill in the art, familiar with standard molecular biology techniques, can employ that knowledge, coupled with the instant disclosure, to make and use these FGF21 mutant polypeptides. Standard techniques can be used for recombinant DNA, oligonucleotide synthesis, tissue culture, and transformation (e.g., electroporation, lipofection). See, e.g., Sambrook et al., *Molecular Cloning: A Laboratory Manual*, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses; chemical analyses; pharmaceutical preparation, formulation, and delivery; and treatment of patients.

Following the preparation of FGF21 mutant polypeptides which contain neither of the cysteines found in the wild-type FGF21 polypeptide sequence but instead comprise an introduced polymer attachment site and optionally one or more additional mutations, the polypeptide can be chemically modified by the attachment of a polymer, as described in Example 9.

6. "Tethered Molecules"

In still another aspect of the present invention, a "Tethered Molecule" can be prepared as described herein. A "Tethered Molecule" is a molecule comprising two FGF21 polypeptides tethered together by a linker molecule. By joining two FGF21 polypeptides together, the effective half-life and potency of a Tethered Molecule can be extended beyond the half-life and potency of a single FGF21 polypeptide.

A Tethered Molecule of the present invention comprises a linker and two FGF21 polypeptides, which can be two naturally occurring FGF21 polypeptides into which no mutations have been introduced, two FGF21 mutant polypeptides having a linker attachment site introduced into the FGF21 polypeptides or a combination of one naturally occurring FGF21 polypeptide and one FGF21 mutant polypeptide. Tethered Molecules comprising at least one FGF21 polypeptide having a non-naturally occurring linker attachment site and one or more additional mutations are also contemplated and form another aspect of the invention. Such Tethered Molecules can thus comprise a mutation that forms a site for the attachment of a linker molecule as well as another mutation to impart another desirable property to the Tethered Molecule.

As used herein, the term "linker attachment site" means a naturally or non-naturally occurring amino acid having a functional group with which a linker can be associated. In one example, a linker attachment site is a residue containing a thiol group, which can be associated with a PEG molecule.

6.A. FGF21 Polypeptides in a Tethered Molecule

When a Tethered Molecule comprises two FGF21 mutant polypeptides, the FGF21 mutant polypeptides can comprise one or more mutations introduced into the sequence, but the mutations need not be at the same amino acid position in each of the FGF21 mutant polypeptides. By way of example, if a Tethered Molecule comprises two FGF21 mutant polypeptides, one FGF21 mutant polypeptide may contain an H125C mutation, which may form an attachment point for a linker molecule. In contrast, the other FGF21 mutant polypeptide can contain a mutation at a position other than H125 which can serve as an attachment point for the linker tethering the two FGF21 mutant polypeptides together. Even if one or two FGF21 mutant polypeptides are employed, the linker can be attached at the N terminal end of the FGF21 mutant polypeptide; introduced attachment points need not necessarily be used.

When a Tethered Molecule comprises one or two naturally-occurring FGF21 polypeptides the linker can be attached at a point in the FGF21 polypeptide that is amenable to the attachment chemistry. For example, naturally occurring disulfide bonds can be reduced and the cysteine residues can serve as attachment points for a linker, such as PEG. In another embodiment, a linker can be attached to a FGF21 polypeptide at the N-terminus or on lysine sidechains.

One or both of the FGF21 mutant polypeptides of a Tethered Molecule can comprise a truncated FGF21 mutant polypeptide. As described herein, a truncated FGF21 mutant polypeptide can be prepared by removing any number of residues on either the N-terminus, the C-terminus or both the N- and C-termini.

Tethered Molecules can also comprise one or both FGF21 polypeptides which comprise a mutation in the polypeptide sequence that may not be preferred as a linker attachment site, but instead may impart some other desirable property to the Tethered Molecule. Thus, Tethered Molecules comprising one or more FGF21 mutant polypeptides into which a mutation imparting a desirable property to the Tethered Molecule form a further aspect of the present invention.

The activity of Tethered Molecules can be assayed in a variety of ways, for example, using an in vitro ELK-luciferase assay as described herein in Example 10.

The activity of the Tethered Molecules of the present invention can also be assessed in an in vivo assay, such as with ob/ob mice as shown in Example 12. Generally, to assess the in vivo activity of one or more of these polypeptides, the polypeptide can be administered to a test animal intraperitoneally. After one or more desired time periods, a blood sample can be drawn, and blood glucose levels can be measured.

As with all FGF21 mutants of the present invention, the FGF21 polypeptides that comprise a Tethered Molecule, which can be FGF21 mutant polypeptides, wild-type FGF21 polypeptides or a combination of both, can optionally comprise an amino-terminal methionine residue, which can be introduced by directed mutation or as a result of a bacterial expression process.

Those of ordinary skill in the art, familiar with standard molecular biology techniques, can employ that knowledge, coupled with the instant disclosure, to make and use the Tethered Molecules of the present invention. Standard techniques can be used for recombinant DNA, oligonucleotide synthesis, tissue culture, and transformation (e.g., electroporation, lipofection). See, e.g., Sambrook et al., *Molecular Cloning: A Laboratory Manual*, which is incorporated herein by reference for any purpose. Enzymatic reactions and purification techniques can be performed according to manufacturer's specifications, as commonly accomplished in the art, or as described herein. Processes for associating linkers with FGF21 polypeptides will depend on the nature of the linker, but are known to those of skill in the art. Examples of linker attachment chemistries are described herein. Guidance on how a Tethered Molecule of the present invention can be formed is provided herein, for example in Example 9.

Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses; chemical analyses; pharmaceutical preparation, formulation, and delivery; and treatment of patients.

6.B. Linkers in Tethered Molecules

Any linker can be employed in a Tethered Molecule to tether the two FGF21 mutant polypeptides together. Linker molecules can be branched or unbranched and can be attached to a FGF21 mutant polypeptide using various known chemistries, such as those described herein. The chemical structure of a linker is not critical, since it serves primarily as a spacer. The linker can be independently the same or different from any other linker, or linkers, that may be present in a Tethered Molecule (e.g., a Tethered Molecule comprising three or more FGF21 mutant or wild-type polypeptides). In one embodiment, a linker can be made up of amino acids linked together by peptide bonds. Some of these amino acids can be glycosylated, as is well understood by those in the art. For example, a useful linker sequence constituting a sialylation site is $X_1X_2NX_4X_5G$ (SEQ ID NO: 5), wherein $X_1$, $X_2$, $X_4$ and $X_5$ are each independently any amino acid residue. In another embodiment a linker molecule can be a PEG molecule of any size, such as 20 kDa, 30 kDa or 40 kDa.

In embodiments in which a peptidyl linker is present (i.e., made up of amino acids linked together by peptide bonds) that is made in length, preferably, of from 1 up to about 40 amino acid residues, more preferably, of from 1 up to about 20 amino acid residues, and most preferably of from 1 to about 10 amino acid residues. In one embodiment, the amino acid residues in the linker are selected from any the twenty canonical amino acids. In another embodiment the amino acid residues in the linker are selected from cysteine, glycine, alanine, proline, asparagine, glutamine, and/or serine. In yet another embodiment, a peptidyl linker is made up of a majority of amino acids that are sterically unhindered, such as glycine, serine, and alanine linked by a peptide bond. It is often desirable that, if present, a peptidyl linker be selected that avoids rapid proteolytic turnover in circulation in vivo. Thus, preferred peptidyl linkers include polyglycines, particularly $(Gly)_4$ (SEQ ID NO: 6); $(Gly)_5$ (SEQ ID NO: 7); poly(Gly-Ala); and polyalanines. Other preferred peptidyl linkers include GGGGS (SEQ ID NO: 8); GGGGSGGGGS (SEQ ID NO: 9); GGGGSGGGGSGGGGSGGGGSGGGGS (SEQ ID NO: 10) and any linkers used in the Examples provided herein. The linkers described herein, however, are exemplary; linkers within the scope of this invention can be much longer and can include other residues.

In embodiments of a Tethered Molecule that comprise a peptide linker moiety, acidic residues, for example, glutamate or aspartate residues, are placed in the amino acid sequence of the linker moiety. Examples include the following peptide linker sequences:

| | |
|---|---|
| GGEGGG; | (SEQ ID NO: 11) |
| GGEEEGGG; | (SEQ ID NO: 12) |
| GEEEG; | (SEQ ID NO: 13) |
| GEEE; | (SEQ ID NO: 14) |
| GGDGGG; | (SEQ ID NO: 15) |
| GGDDDGG; | (SEQ ID NO: 16) |
| GDDDG; | (SEQ ID NO: 17) |
| GDDD; | (SEQ ID NO: 18) |
| GGGGSDDSDEGSDGEDGGGGS; | (SEQ ID NO: 19) |
| WEWEW; | (SEQ ID NO: 20) |
| FEFEF; | (SEQ ID NO: 21) |
| EEEWWW; | (SEQ ID NO: 22) |
| EEEFFF; | (SEQ ID NO: 23) |
| WWEEEWW; or | (SEQ ID NO: 24) |
| FFEEEFF. | (SEQ ID NO: 25) |

In other embodiments, a peptidyl linker constitutes a phosphorylation site, e.g., $X_1X_2YX_3X_4G$ (SEQ ID NO: 26), wherein $X_1$, $X_2$, $X_3$ and $X_4$ are each independently any amino acid residue; $X_1X_2SX_3X_4G$ (SEQ ID NO: 27), wherein $X_1$, $X_2$, $X_3$ and $X_4$ are each independently any amino acid residue; or $X_1X_2TX_3X_4G$ (SEQ ID NO: 28), wherein $X_1$, $X_2$, $X_3$ and $X_4$ are each independently any amino acid residue.

Non-peptide linkers can also be used in a Tethered Molecule. For example, alkyl linkers such as —NH—$(CH_2)_s$—C(O)—, wherein s=2 to 20 could be used. These alkyl linkers can further be substituted by any non-sterically hindering group such as lower alkyl (e.g., $C_1$-$C_6$) lower acyl, halogen (e.g., Cl, Br), CN, $NH_2$, phenyl, etc.

Any suitable linker can be employed in the present invention to from Tethered Molecules. In one example, the linker used to produce Tethered Molecules described herein were homobifunctional bis-maleimide PEG molecules having the general structure:

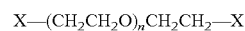

X—$(CH_2CH_2O)_n$$CH_2CH_2$—X where X is a maleimide group. In other embodiments, X can be an orthopyridyl-disulphide, an iodoacetamide, a vinylsulfone or any other reactive moiety known to the art to be specific for thiol groups. In yet another embodiment X can be an amino-specific reactive moiety used to tether two mutant polypeptides through either the N-terminus or an engineered lysyl group. (See, e.g., Pasut and Veronese, 2006, "PEGylation of Proteinsas Tailored Chemistry for Optimized Bioconjugates," *Adv. Polym. Sci.* 192:95-134).

In still another embodiment, a linker can have the general structure:

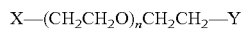

$$X-(CH_2CH_2O)_nCH_2CH_2-Y$$

where X and Y are different reactive moieties selected from the groups above. Such a linker would allow conjugation of different mutant polypeptides to generate Tethered heterodimers or hetero-oligomers.

In a further embodiment, a linker can be a PEG molecule, which can have a molecular weight of 1 to 100 kDa, preferably 10 to 50 kDa (e.g., 10, 20, 30 or 40 kDa) and more preferably 20 kDa. The peptide linkers can be altered to form derivatives in the same manner as described above.

Other examples of useful linkers include aminoethyloxyethyloxy-acetyl linkers as disclosed in International Publication No. WO 2006/042151, incorporated herein by reference in its entirety.

When forming a Tethered Molecule of the present invention, standard chemistries can be employed to associate a linker with a wild-type or mutant FGF21 molecule. The precise method of association will depend on the attachment site (e.g., which amino acid side chains) and the nature of the linker. When a linker is a PEG molecule, attachment can be achieved by employing standard chemistry and a free sulfhydryl or amine group, such as those found on cysteine residues (which can be introduced into the FGF21 polypeptide sequence by mutation or can be naturally occurring) or on lysine (which can be introduced into the FGF21 polypeptide sequence by mutation or can be naturally occurring) or N-terminal amino groups.

7. Chemical Modification of FGF21 Mutants

In an aspect of the present invention, FGF21 mutant polypeptides are chemically modified. The term "chemically modified" refers to a polypeptide (e.g., an FGF21 mutant polypeptide) that has been modified by the addition of a polymer at one or more sites on the polypeptide. Examples of chemically modified forms of a FGF21 mutant polypeptide include PEGylated and glycosylated forms of an FGF21 mutant polypeptide.

Chemically modified FGF21 mutant polypeptides of the present invention can comprise any type of polymer, including water soluble polymers, such as PEG. Exemplary polymers each can be of any molecular weight and can be branched or unbranched. The polymers each typically have an average molecular weight of between about 2 kDa to about 100 kDa (the term "about" indicating that in preparations of a water-soluble polymer, some molecules will weigh more and some less than the stated molecular weight). The average molecular weight of each polymer is preferably between about 5 kDa and about 50 kDa, more preferably between about 10 kDa and about 40 kDa, and most preferably between about 10 kDa and about 20 kDa.

Suitable water-soluble polymers or mixtures thereof include, but are not limited to, carbohydrates, polyethylene glycol (PEG) (including the forms of PEG that have been used to derivatize proteins, including mono-$(C_1-C_{10})$, alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules that can be used to prepare covalently attached FGF21 polypeptide mutant multimers. Also encompassed by the present invention are FGF21 mutants covalently attached to polysialic acid.

In some embodiments of the present invention, an FGF21 mutant polypeptide is covalently, modified to include one or more water-soluble polymers, including, but not limited to, polyethylene glycol (PEG), polyoxyethylene glycol, or polypropylene glycol. See, e.g., U.S. Pat. Nos. 4,640,835; 4,496,689; 4,301,144; 4,670,417; 4,791,192; and 4,179,337. In some embodiments of the present invention, an FGF21 mutant comprises one or more polymers, including, but not limited to, monomethoxy-polyethylene glycol, dextran, cellulose, another carbohydrate-based polymer, poly-(N-vinyl pyrrolidone)-polyethylene glycol, propylene glycol homopolymers, a polypropylene oxide/ethylene oxide co-polymer, polyoxyethylated polyols (e.g., glycerol), polyvinyl alcohol, or mixtures of such polymers.

In yet other embodiments of the present invention, a peptide or a protein can be conjugated to FGF21 in a site directed manner though the aforementioned engineered residues in order impart favorable properties to FGF21 (e.g. potency, stability, selectivity). Thus the present invention encompasses FGF21 mutant polypeptides conjugated to a hetero-protein or heteropeptide at an introduced polymer attachment site. Examples of suitable proteins include HSA and antibodies that do not bind to FGF21.

7.A. PEGylated FGF21 Mutant Polypeptides

In some embodiments of the present invention, an FGF21 mutant polypeptide is covalently-modified with PEG subunits. In some embodiments, one or more water-soluble polymers are bonded at one or more specific positions (for example, at the N-terminus) of the FGF21 mutant. In some embodiments, one or more water-soluble polymers are attached to one or more side chains of an FGF21 mutant; these side chains can be naturally occurring or can form a component of an engineered polymer attachment site. In some embodiments, PEG is used to improve the therapeutic capacity of an FGF21 mutant polypeptide. Certain such methods are discussed, for example, in U.S. Pat. No. 6,133,426, which is hereby incorporated by reference for any purpose.

In embodiments of the present invention wherein the polymer is PEG, the PEG group can be of any convenient molecular weight, and can be linear or branched. The average molecular weight of the PEG group will preferably range from about 2 kD to about 100 kDa, and more preferably from about 5 kDa to about 50 kDa, e.g., 10, 20, 30, 40, or 50 kDa. The PEG groups will generally be attached to the FGF21 mutant via acylation or reductive alkylation through a reactive group on the PEG moiety (e.g., an aldehyde, NHS, or maleimide, vinylsulfone, alkylhalide) to a reactive group on the FGF21 mutant (e.g., an amino or thiol group).

When the polymer(s) attached to a FGF21 mutant polypeptide is PEG, the PEGylation of a FGF21 mutant polypeptide of the present invention, can be specifically carried out using any of the PEGylation reactions known in the art. Such reactions are described, for example, in the following references: Zalipsky, 1995, *Functionalized Poly(ethylene glycol) for Preparation of Biologically Relevant Conjugates*, Bioconjugate Chemistry 6:150-165; Francis et al., 1992, *Focus on Growth Factors* 3: 4-10; European Patent Nos. 0 154 316 and 0 401 384; and U.S. Pat. No. 4,179,337. For example, when the target residue is a lysine residue (i.e., a residue with a reactive amine group) PEGylation can be carried out via an acylation reaction or an alkylation reaction with an amino-reactive polyethylene glycol molecule (or an analogous reactive water-soluble polymer) as described herein. For the acylation reactions, a selected polymer can have a single reactive ester group. For reductive alkylation, a selected polymer can have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714). Various reactive PEG polymers activated with different amino-specific moieties will also known to those of ordinary skill in the art and can also be employed as circumstances dictate.

In another example, when the target residue is a cysteine residue (i.e., a residue with a reactive sulfhydryl group) PEGylation can be carried out via standard maleimide chemistry. For this reaction, the selected polymer can contain one or more reactive maleimide groups or other thiol reactive moiety such as vinylsulfone, orthopyridyl-disulphide or iodoacetamide. See, e.g., Pasut & Veronese, 2006, "PEGylation of Proteins as Tailored Chemistry for Optimized Bioconjugates," *Adv. Polym. Sci.* 192:95-134; Zalipsky, 1995, "Functionalized Poly(ethylene glycol) for Preparation of Biologically Relevant Conjugates," *Bioconjugate Chemistry* 6:150-165, and Hermanson, *Bioconjugate Techniques*, $2^{nd}$ *Ed., Academic Press,* 2008, each of which is incorporated herein by reference.

In some embodiments of the present invention, a useful strategy for the attachment of the PEG group to a FGF21 mutant involves combining through the formation of a conjugate linkage in solution, a FGF21 mutant and a PEG moiety, each bearing a special functionality that is mutually reactive toward the other. The FGF21 mutant is "preactivated" with an appropriate functional group at a specific site. The precursors are purified and fully characterized prior to reacting with the PEG moiety. Ligation of the FGF21 mutant with PEG usually takes place in aqueous phase and can be easily monitored by SDS-PAGE or reverse phase analytical HPLC. Detailed analysis can be done by LC-MS based peptide mapping. Detailed analysis can be done by LC-MS based peptide mapping.

7.B. Polysaccharide FGF21 Mutant Polypeptides

Polysaccharide polymers are another type of water-soluble polymer that can be used for protein modification. Therefore, the FGF21 mutant polypeptides of the present invention can be attached to a polysaccharide polymer to form embodiments of the present invention. Thus, an engineered non-naturally occurring polymer attachment site in an FGF21 mutant polypeptide can comprise a residue to which a polysaccharide is attached. Dextrans are polysaccharide polymers comprised of individual subunits of glucose predominantly linked by alpha 1-6 linkages. The dextran itself is available in many molecular weight ranges, and is readily available in molecular weights from about 1 kD to about 70 kD. Dextran is a suitable water-soluble polymer for use as a vehicle by itself or in combination with another vehicle (e.g., Fc). See, e.g., International Publication No. WO 96/11953. The use of dextran conjugated to therapeutic or diagnostic immunoglobulins has been reported. See, e.g., European Patent Publication No. 0 315 456, which is hereby incorporated by reference. The present invention also encompasses the use of dextran of about 1 kDa to about 20 kDa.

7.C. Methods of Chemically Modifying a FGF21 Mutant Polypeptide

In general, chemical modification (e.g., PEGylation or glycosylation) can be performed under any suitable condition used to react a protein with an activated polymer molecule. Methods for preparing chemically modified FGF21 mutant polypeptides will generally comprise the steps of: (a) reacting the polypeptide with the activated polymer molecule (such as a reactive ester, maleimide or aldehyde derivative of the polymer molecule) under conditions whereby an FGF21 mutant polypeptide becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment of the present invention, chemically modified FGF21 mutant polypeptides can have a single polymer molecule at the amino-terminus, while in other embodiments an FGF21 mutant polypeptide can have two or more polymers associated with the primary sequence, for example one polymer at the N-terminus of the polypeptide and a second at another residue in the polypeptide. Alternatively, a FGF21 mutant can have two or more polymers associated at two different residues in the primary sequence but not at the N-terminus.

Generally, conditions that can be alleviated or modulated by the administration of the present chemically modified FGF21 mutant polypeptides include those described herein for the native FGF21 polypeptide. However, the chemically modified FGF21 mutant polypeptides disclosed herein can have additional activities, such as increased half-life, as compared to wild-type FGF21 and FGF21 mutants.

8. Therapeutic Compositions of FGF21 Mutants and Administration Thereof

Therapeutic compositions comprising FGF21 mutant polypeptides are within the scope of the present invention, and are specifically contemplated in light of the identification of Tethered Molecules, FGF21 mutant polypeptides and chemically modified FGF21 mutant polypeptides that exhibit enhanced properties. Such Tethered Molecule, FGF21 mutant polypeptide, and chemically modified FGF21 mutant polypeptide therapeutic compositions, can comprise a therapeutically effective amount of a Tethered Molecule, FGF21 mutant polypeptide or chemically modified FGF21 mutant polypeptide, which can be chemically modified, in a mixture with a pharmaceutically or physiologically acceptable formulation agent selected for suitability with the mode of administration.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., *Remington's Pharmaceutical Sciences* (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage (see, e.g., *Remington's Pharmaceutical Science*). Such compositions can influence the physical state, stability, rate of in vivo release, and rate of in vivo clearance of the Tethered Molecule, FGF21 mutant polypeptide (which can be truncated, capped or C-terminally mutated) or chemically modified FGF21 mutant polypeptide.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the present invention, Tethered Molecule, FGF21 mutant polypeptide and chemically modified FGF21 mutant polypeptide compositions can be prepared for storage by mixing the selected composition having the desired degree of purity with optional formulation agents (*Remington's Pharmaceutical Sciences*, supra) in the form of a lyophilized cake or an aqueous solution. Further, the Tethered Molecule, FGF21 mutant polypeptide and chemically modified FGF21 mutant polypeptide product can be formulated as a lyophilizate using appropriate excipients such as sucrose.

The pharmaceutical compositions of the present invention can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention can be in the form of a pyrogen-free, parenterally acceptable, aqueous solution comprising the desired Tethered Molecule, FGF21 mutant polypeptide or chemically modified FGF21 mutant polypeptide in a pharmaceutically acceptable vehicle. A particularly suitable vehicle for parenteral injection is sterile distilled water in which a Tethered Molecule, FGF21 mutant polypeptide or chemically modified FGF21 mutant polypeptide is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, Tethered Molecule, FGF21 mutant polypeptide or chemically modified FGF21 mutant polypeptide can be formulated as a dry powder for inhalation. Such inhalation solutions can also be formulated with a propellant for aerosol delivery. In yet another embodiment, solutions can be nebulized. Pulmonary administration is further described in International Publication No. WO 94/20069, which describes the pulmonary delivery of chemically modified proteins.

It is also contemplated that certain formulations can be administered orally. In one embodiment of the present invention, a Tethered Molecule, FGF21 mutant polypeptide (which can be truncated, capped or C-terminally mutated) or chemically modified FGF21 mutant polypeptide that is administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the Tethered Molecule, FGF21 mutant polypeptide (which can be truncated, capped or C-terminally mutated) or chemically modified FGF21 mutant polypeptide. Diluents, flavorings, low melting point waxes, vegetable oils, lubricants, suspending agents, tablet disintegrating agents, and binders can also be employed.

Another pharmaceutical composition can involve a therapeutically effective quantity of a Tethered Molecule, FGF21 mutant polypeptide (which can be truncated, capped or C-terminally mutated) or chemically modified FGF21 mutant polypeptide in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional Tethered Molecule, FGF21 mutant polypeptide or chemically modified FGF21 mutant polypeptide pharmaceutical compositions will be evident to those skilled in the art, including formulations involving Tethered Molecule, FGF21 mutant polypeptides or chemically modified FGF21 mutant polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art (see, e.g., International Publication No. WO 93/15722, which describes the controlled release of porous polymeric microparticles for the delivery of pharmaceutical compositions).

Additional examples of sustained-release preparations include semipermeable polymer matrices in the form of shaped articles, e.g., films, or microcapsules. Sustained release matrices can include polyesters, hydrogels, polylactides (U.S. Pat. No. 3,773,919 and European Patent No. 0 058 481), copolymers of L-glutamic acid and gamma ethyl-L-glutamate (Sidman et al., 1983, *Biopolymers* 22: 547-56), poly(2-hydroxyethyl-methacrylate) (Langer et al., 1981, *J. Biomed. Mater. Res.* 15: 167-277 and Langer, 1982, *Chem. Tech.* 12: 98-105), ethylene vinyl acetate (Langer et al., supra) or poly-D(−)-3-hydroxybutyric acid (European Patent No. 0 133 988). Sustained-release compositions can also include liposomes, which can be prepared by any of several methods known in the art. See, e.g., Epstein et al., 1985, *Proc. Natl. Acad. Sci. U.S.A.* 82: 3688-92; and European Patent Nos. 0 036 676, 0 088 046, and 0 143 949.

A Tethered Molecule, FGF21 mutant polypeptide or chemically modified FGF21 mutant polypeptide pharmaceutical composition to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

In a specific embodiment, the present invention is directed to kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

A therapeutically effective amount of a Tethered Molecule, FGF21 mutant polypeptide (which can be truncated, capped or C-terminally mutated) or chemically modified FGF21 mutant polypeptide pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the Tethered Molecule, FGF21 mutant polypeptide or chemically modified FGF21 mutant polypeptide is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 ng/kg to up to about 100 mg/kg or more, depending on the factors mentioned above. In other embodiments, the dosage can range from 0.01 mg/kg up to about 10 mg/kg, for example 0.05 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 2 mg/kg, 3 mg/kg, 4 mg/kg, 5 mg/kg, 6 mg/kg, 7 mg/kg, 8 mg/kg, 9 mg/kg or 10 mg/kg.

The frequency of dosing will depend upon the pharmacokinetic parameters of the Tethered Molecule, FGF21 mutant polypeptide or chemically modified FGF21 mutant polypeptide in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

10. Therapeutic Uses of FGF21 Polypeptide Mutants

The Tethered Molecules, FGF21 mutant polypeptides (which can be truncated, capped or C-terminally mutated) and chemically modified FGF21 mutant polypeptides of the present invention can be used to treat, diagnose, ameliorate, or prevent a number of diseases, disorders, or conditions, including, but not limited to metabolic disorders. In one embodiment, the metabolic disorder to be treated is diabetes. In another embodiment, the metabolic disorder is obesity. Other embodiments include metabolic conditions or disorders such as dyslipidimia; hypertension; hepatosteaotosis, such as non-alcoholic steatohepatitis (NASH); cardiovascular disease, such as atherosclerosis; and aging.

In application, a disorder or condition such as diabetes or obesity can be treated by administering a Tethered Molecule, FGF21 mutant polypeptide or chemically modified FGF21 mutant polypeptide as described herein to a patient in need thereof in the amount of a therapeutically effective dose. The administration can be performed as described herein, such as by IV injection, intraperitoneal injection, intramuscular injection, or orally in the form of a tablet or liquid formation. In most situations, a desired dosage can be determined by a clinician, as described herein, and can represent a therapeutically effective dose of the Tethered Molecule, FGF21 mutant polypeptide or chemically modified FGF21 mutant polypeptide. It will be apparent to those of skill in the art that a therapeutically effective dose of Tethered Molecule, FGF21 mutant polypeptide or chemically modified FGF21 mutant polypeptide will depend, inter alia, upon the administration schedule, the unit dose of antigen administered, whether the nucleic acid molecule or polypeptide is administered in combination with other therapeutic agents, the immune status and the health of the recipient. The term "therapeutically effective dose," as used herein, means that amount of Tethered Molecule, FGF21 mutant polypeptide or chemically modified FGF21 mutant polypeptide that elicits the biological or medicinal response in a tissue system, animal, or human being sought by a researcher, medical doctor, or other clinician, which includes alleviation of the symptoms of a disease or disorder being treated.

11. Antibodies

Antibodies and antibody fragments that specifically bind to the Tethered Molecules, FGF21 mutant polypeptides and chemically modified FGF21 mutant polypeptides of the present invention but do not specifically bind to wild-type FGF21 polypeptides are contemplated and are within the scope of the present invention. The antibodies can be polyclonal, including monospecific polyclonal; monoclonal (MAbs); recombinant; chimeric; humanized, such as complementarity-determining region (CDR)-grafted; human; single chain; and/or bispecific; as well as fragments; variants; or chemically modified molecules thereof. Antibody fragments include those portions of the antibody that specifically bind to an epitope on an FGF21 mutant polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a Tethered Molecule, FGF21 mutant polypeptide or chemically modified FGF21 mutant polypeptide generally are produced in animals (e.g., rabbits or mice) by means of multiple subcutaneous or intraperitoneal injections of the FGF21 mutant polypeptide and an adjuvant. It can be useful to conjugate an FGF21 mutant polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-Tethered Molecule, FGF21 mutant polypeptide or chemically modified FGF21 mutant polypeptide antibody titer.

Monoclonal antibodies directed toward Tethered Molecules, FGF21 mutant polypeptides or chemically modified FGF21 mutant polypeptides can be produced using any method that provides for the production of antibody molecules by continuous cell lines in culture. Examples of suitable methods for preparing monoclonal antibodies include the hybridoma methods of Kohler et al., 1975, *Nature* 256: 495-97 and the human B-cell hybridoma method (Kozbor, 1984, *J. Immunol.* 133: 3001; Brodeur et al., *Monoclonal Antibody Production Techniques and Applications* 51-63 (Marcel Dekker, Inc., 1987). Also provided by the invention are hybridoma cell lines that produce monoclonal antibodies reactive with Tethered Molecules, FGF21 mutant polypeptides or chemically modified FGF21 mutant polypeptides.

The anti-FGF21 mutant antibodies of the invention can be employed in any known assay method, such as competitive binding assays, direct and indirect sandwich assays, and immunoprecipitation assays (see, e.g., Sola, *Monoclonal Antibodies: A Manual of Techniques* 147-158 (CRC Press, Inc., 1987), incorporated herein by reference in its entirety) for the detection and quantitation of FGF21 mutant polypeptides. The antibodies will bind FGF21 mutant polypeptides with an affinity that is appropriate for the assay method being employed.

For diagnostic applications, in certain embodiments, anti-Tethered Molecule, FGF21 mutant polypeptide or chemically modified FGF21 mutant polypeptide antibodies can be labeled with a detectable moiety. The detectable moiety can be any one that is capable of producing, either directly or indirectly, a detectable signal. For example, the detectable moiety can be a radioisotope, such as $^3H$, $^{14}C$, $^{32}P$, $^{35}S$, $^{125}I$, $^{99}Tc$, $^{111}In$, or $^{67}Ga$; a fluorescent or chemiluminescent compound, such as fluorescein isothiocyanate, rhodamine, or luciferin; or an enzyme, such as alkaline phosphatase, β-galactosidase, or horseradish peroxidase (Bayer et al., 1990, *Meth. Enz.* 184: 138-63).

Competitive binding assays rely on the ability of a labeled standard (e.g., an FGF21 mutant polypeptide, or an immunologically reactive portion thereof) to compete with the test sample analyte (e.g., a Tethered Molecule, FGF21 mutant polypeptide or chemically modified FGF21 mutant polypeptide) for binding with a limited amount of anti-Tethered Molecule, FGF21 mutant polypeptide or chemically modified FGF21 mutant polypeptide antibody, depending on the analyte. The amount of Tethered Molecule, FGF21 mutant polypeptide or chemically modified FGF21 mutant polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies can conveniently be separated from the standard and analyte that remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody that is immobilized on a solid support, and thereafter a second antibody binds to the analyte, thus forming an insoluble three-part complex. See, e.g., U.S. Pat. No. 4,376,110. The second antibody can itself be labeled with a detectable moiety (direct sandwich assays) or can be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The anti-Tethered Molecule, FGF21 mutant polypeptide or chemically modified FGF21 mutant polypeptide antibodies of the present invention are also useful for in vivo imaging. An antibody labeled with a detectable moiety can be administered to an animal, preferably into the bloodstream, and the presence and location of the labeled antibody in the host assayed. The antibody can be labeled with any moiety that is detectable in an animal, whether by nuclear magnetic resonance, radiology, or other detection means known in the art.

The invention also relates to a kit comprising Tethered Molecules, FGF21 mutant polypeptides or chemically modified FGF21 mutant polypeptide antibodies and other reagents useful for detecting Tethered Molecule, FGF21 mutant polypeptide or chemically modified FGF21 mutant polypeptide levels in biological samples. Such reagents can include a detectable label, blocking serum, positive and negative control samples, and detection reagents.

EXAMPLES

The Examples that follow are illustrative of specific embodiments of the invention, and various uses thereof. They are set forth for explanatory purposes only, and should not be construed as limiting the scope of the invention in any way.

Example 1

Preparation of FGF21 Polypeptide Expression Constructs

A nucleic acid sequence encoding the mature FGF21 polypeptide was obtained by polymerase chain reaction (PCR) amplification using primers having nucleotide sequences corresponding to the 5' and 3' ends of the mature FGF21 sequence. Table 4 lists the primers that were used to amplify the mature FGF21 sequence.

TABLE 4

PCR Primers for Preparing FGF21 Construct

| Primer | Sequence | SEQ ID NO: |
|---|---|---|
| Sense | 5'-AGGAGGAATAACATATGCATCCA ATTCCAGATTCTTCTCC-3' | 33 |
| Antisense | 5'-TAGTGAGCTCGAATTCTTAGGA GCGTAGCTGG-3' | 34 |

The primers used to prepare the FGF21 expression construct incorporated restriction endonuclease sites for directional cloning of the sequence into a suitable expression vector (e.g., pET30 (Novagen/EMD Biosciences; San Diego, Calif.) or pAMG33 (Amgen; Thousand Oaks, Calif.)). The expression vector pAMG33 contains a low-copy number R-100 origin of replication, a modified lac promoter, and a kanamycin-resistance gene. The expression vector pET30 contains a pBR322-derived origin of replication, an inducible T7 promoter, and a kanamycin-resistance gene. While expression from pAMG33 was found to be higher, pET30 was found to be a more reliable cloning vector. Thus, the majority of the constructs described in the instant application were first generated in pET30 and then screened for efficacy. Selected sequences were then transferred to pAMG33 for further amplification.

The FGF21 sequence was amplified in a reaction mixture containing 40.65 µL dH$_2$O, 5 µL, PfuUltra II Reaction Buffer (10×), 1.25 µL dNTP Mix (40 mM-4×10 mM), 0.1 µL Template (100 ng/mL), 1 µL Primer1 (10 µM), 1 µL Primer2 (10 µM), and 1 µL PfuUltra II fusion HS DNA Polymerase (Stratagene; La Jolla, Calif.). Amplification reactions were performed by heating for two minutes at 95° C.; followed by ten cycles at 95° C. for 20 seconds, 60° C. for 20 seconds (with an additional 1° C. subtracted per cycle), and 72° C. for 15 seconds/kilobase of desired product; followed by 20 cycles at 94° C. for 20 seconds, 55° C. for 20 seconds, and 72° C. for 15 seconds/kilobase of desired product; followed by 72° C. for three minutes. Amplification products were digested with the restriction endonucleases NdeI and EcoRI; ligated into a suitable vector; and then transformed into competent cells.

As a result of the bacterial expression system employed, the expressed mature FGF21 polypeptide included an N-terminal methionine residue or a variant methionine residue such as fMet or gluconylated Met.

Example 2

Purification of Wild-Type FGF21 Polypeptides from Bacteria

In the Examples that follow, wild-type FGF21 polypeptides were expressed in a bacterial expression system. After expression, which is described below, the wild-type FGF21 polypeptides were purified as described in this Example, unless otherwise indicated.

To purify the wild-type FGF21 polypeptide from bacterial inclusion bodies, double-washed inclusion bodies (DWIBs) were solubilized in a solubilization buffer containing guanidine hydrochloride and DTT in Tris buffer at pH 8.5 and then mixed for one hour at room temperature, and the solubilization mixture was added to a refold buffer containing urea, arginine, cysteine, and cystamine hydrochloride at pH 9.5 and then mixed for 24 hours at 5° C. (see, e.g., Clarke, 1998, *Curr. Opin. Biotechnol.* 9: 157-63; Mannall et al., 2007, *Biotechnol. Bioeng.* 97: 1523-34; Rudolph et al., 1997, "Folding proteins," in *Protein Function: A Practical Approach* (Creighton, ed., New York, IRL Press), pp 57-99; and Ishibashi et al., 2005, *Protein Expr. Purif.* 42: 1-6).

Following solubilization and refolding, the mixture was filtered through a 0.45 micron filter. The refold pool was then concentrated approximately 10-fold with a 10 kD molecular weight cut-off Pall Omega cassette at a transmembrane pressure (TMP) of 20 psi, and dialfiltered with 3 column volumes of 20 mM Tris, pH 8.0 at a TMP of 20 psi.

The clarified sample was then subjected to anion exchange (AEX) chromatography using a Q Sepharose HP resin. A linear salt gradient of 0 to 250 mM NaCl in 20 mM Tris was run at pH 8.0 at 5° C. Peak fractions were analyzed by SDS-PAGE and pooled.

The AEX eluate pool was then subjected to hydrophobic interaction chromatography (HIC) using a Phenyl Sepharose HP resin. Protein was eluted using a decreasing linear gradient of 0.7 M to 0 M ammonium sulfate at pH 8.0 and ambient temperature. Peak fractions were analyzed by SDS-PAGE (Laemmli, 1970, *Nature* 227: 680-85) and pooled.

The HIC pool was concentrated with a 10 kD molecular weight cut-off Pall Omega 0.2 m$^2$ cassette to 7 mg/mL at a TMP of 20 psi. The concentrate was dialfiltered with 5 volumes of 10 mM KPO$_4$, 5% sorbitol, pH 8.0 at a TMP of 20 psi, and the recovered concentrate was diluted to 5 mg/mL. Finally, the solution was filtered through a Pall mini-Kleenpac 0.2 µM Posidyne membrane.

Example 3

Identification of FGF21 Mutants

Wild-type FGF21 has a relatively short half life, and in some cases this can be undesirable for the use of wild-type FGF21 as a therapeutic. Additionally, traditional methods of extending half life, such as PEGylation of the polypeptide are limited by the number and location of suitable PEGylation sites in the FGF21 sequence. In the wild-type FGF21 polypeptide sequence there are seven naturally occurring PEGylation sites, namely the alpha amino group, four lysine residues, and two cysteine residues. These sites are not ideal for PEGylation because the PEG molecule can adversely affect the ability of FGF21 to obtain its native structure, or it can adversely affect the interaction between FGF21 and its receptor or beta-klotho. In addition, with the exception of the alpha amino group, these reactive residues do not allow for the site specific PEGylation at a single targeted location. Accordingly, a directed and focused study was undertaken to identify residues within the wild-type FGF21 polypeptide that could be mutated to a residue suitable for chemical modification. Considerations in the study included the location of the residue in the FGF21 sequence, as well as its position on the protein surface.

Two different strategies were employed in an effort to identify individual residues in the wild-type FGF21 polypeptide that would be suitable for mutation to a residue useful for chemical modification, described herein.

Example 3.A

Mutation Candidates Identified Using a Homology Model

In the first strategy, a homology model was employed in a systematic rational protein engineering approach to identify residues with a high probability of having surface exposed sidechains that were likely to tolerate PEGylation without interfering with FGF21 activity. Since there are no published X-ray or NMR structures of FGF21 that could be used to identify such residues, a high resolution (1.3 Å) X-ray crystal structure of FGF19 (1PWA) obtained from the Protein Databank (PDB) was used to create a 3D homology model of FGF21 using MOE (Molecular Operating Environment; Chemical Computing Group; Montreal, Quebec, Canada) modeling software. FGF19 was chosen as a template, since among the proteins deposited in the PDB, FGF19 is the most closely related protein to FGF21 in terms of the amino acid sequence homology.

The FGF21 homology model was then extended to represent FGF-21 bound to an FGF receptor. This model was used to identify residues that would likely be exposed on the surface of the FGF21 molecule and available for reaction with an activated polymer (e.g., PEG) moiety, while avoiding those residues that might interfere with FGF21 interaction with its receptor. Considerations were also made for the sequence conservation of the residues between species as well as the biochemical properties of the native side chain. Residues identified as good candidates by this screen were ranked according to the estimated probability of successful PEGylation of this site with minimal disruption of activity. Residues in Group A reflect the best candidates, and residues in Group D reflect viable but less preferred candidates. Group A includes N121, H125, H112, R77, H87, E37 and K69. Group B includes R126, G113, D79, E91, D38, D46 and G120. Group C includes S71, D89, L86, T70, G39, T40, R36, P49, S48, S123, K122, A81, A111, E110 and R96. Finally, Group D includes Q18, R19, A26, Q28, E34, A44, A45, E50, L52, Q54, L55, K59, G61, L66, V68, R72, P78, G80, Y83, S85, F88, P90, A92, S94, L98, E101, D102, Q108, L114, H117, P119, P124, D127, P128, A129, P130, R131, and P140.

In addition, potential PEGylation sites within the amino and carboxy-terminal segments of the molecule were identified based on sequence alignments and the biochemical properties of the sidechains, since no three dimensional structural data is available for these portions of the molecule. Residues that were believed to be most suitable for mutation were identified and subsequently grouped according to how well the residues fit a set of selection criteria. With respect to the N-terminus of the FGF21 polypeptide sequence, residues 1-13 were evaluated, and D5 was determined to be the best candidate for mutation, with residues H1, P2, I3, P4 and S6 also determined to be viable. With respect to the C-terminus of the FGF21 polypeptide sequence, residues 141-181 were evaluated, and residues Y179 and R175 were determined to be the best candidates for mutation, with residues P143, P171, S172, Q173, G174, S176, P177, S178, A180, and S181 forming another group of candidates, and residues P144, A145, P147, E148, P149, P150, I152 A154, Q156 and G170 forming a third group of candidates for mutation.

Example 3.B

FGF21 Mutants Generated by Removing Undesired Naturally Occurring Polymer Attachment Sites The second strategy employed an amino-specific conjugation chemistry for coupling PEG to FGF21. Site-selective dual-PEGylation of potentially vacuologenic conjugates may significantly reduce their vacuologenic potential (see, e.g., U.S. Pat. No. 6,420,339). Accordingly, in one aspect of the present invention, site-selective dual-PEGylation of FGF21 is accomplished by mutating the protein so that only two primary amino groups remain for PEGylation.

The FGF21 protein contains four lysine and ten arginine residues as highlighted by bold (R and K residues) and underlining (K residues) in the wild-type FGF21 sequence (SEQ ID NO:4). The two naturally occurring cysteine residues are highlighted in bold and italic:

SEQ ID NO: 4
HPIPDSSPLLQFGGQVRQRYLYTDDAQQTEAHLEIREDGTVGGAADQS

PESLLQLKALKPGVIQILGVKTSRFL*C*QRPDGALYGSLHFDPEA*C*SFRE

LLLEDGYNVYQSEAHGLPLHLPGNKSPHRDPAPRGPARFLPLPGLPPA

PPEPPGILAPQPPDVGSSDPLSMVGPSQGRSPSYAS

The four naturally occurring lysines were first mutated to arginines to create a parent molecule containing only one primary amine group as an α-amino group at the N-terminus. This was tested for in vitro activity and found to be fully active. Next, selected arginines were step-wise replaced with lysine to create up to ten analogs containing a second primary amino group for PEGylation at various positions on the FGF21 molecule. An examination of the homology model of FGF21 bound to its receptor (as described in Example 3A) allowed ranking of the proposed conjugation sites as a function of their proximity to the putative receptor interface. Sites that appeared buried were not addressed.

The various positions were ranked and characterized as follows: (a) Sites that are solvent exposed and distal to the receptor interface: R36, R77, K122 & R126; (b) Sites that are solvent exposed and proximal to the receptor interface: K56, K59, K69, R72 & R175; and (c) Sites that are buried: R17, R19, R131 & R135.

The final constructs, each containing a single α-amino and ε-amino group were purified, and tested for activity both before and after conjugation with PEG as described in Examples 9 (conjugation) and 10 (in vitro activity assay).

Example 4

Identification of FGF21 Mutants Comprising a Single Mutation

A summary of FGF21 mutants comprising a single mutation that were generated through the rational protein engineering approach described above in Example 3.A and 3.B is provided in Table 3. These single mutants provide and incorporate a non-naturally occurring polymer attachment site, notably a cysteine or lysine residue. The side chains of these residues are particularly suited to chemical modification by the attachment of a polymer, such as a PEG molecule. It was recognized that in addition to the introduced non-naturally occurring polymer attachment site, a polymer could optionally be attached to the N-terminus of the protein, as desired.

Since the introduced residues were designed to maintain the wild-type levels of FGF21 biological activity, these FGF21 mutant polypeptides are expected to maintain FGF21 biological activity and yet still provide one or more non-naturally occurring polymer attachment sites. After chemical modification (e.g., PEGylation) these mutants are expected to have a longer in vivo half life than wild-type FGF21, while maintaining significant in vivo wild-type levels of biological activity.

The numbers of the positions targeted for mutagenesis are given in Table 5 and correspond to the residue position in the mature FGF21 protein, which consists of 181 amino acid residues. Nucleic acid sequences encoding the FGF21 mutant polypeptides listed in Table 5 below were prepared using the techniques described below.

TABLE 5

FGF21 Mutant Polypeptides Comprising a Single Mutation

| Residue Number | WT | Mutation | |
|---|---|---|---|
| 36 | R | K | R36K |
| 37 | E | C | E37C |
| 38 | D | C | D38C |
| 46 | D | C | D46C |
| 56 | K | R | K56R |
| 60 | K | R | K60R |
| 91 | E | C | E91C |
| 69 | K | C | K69C |
| 69 | K | R | K69R |
| 72 | R | K | R72K |
| 77 | R | C | R77C |
| 77 | R | K | R77K |
| 79 | D | C | D79C |
| 86 | H | C | H86C |
| 91 | E | C | E91C |
| 112 | H | C | H112C |
| 113 | G | C | G113C |
| 120 | G | C | G120C |
| 121 | N | C | N121C |
| 122 | K | R | K122R |
| 125 | H | C | H125C |
| 126 | R | C | R126C |
| 126 | R | K | R126K |
| 171 | P | G | P171G |
| 175 | R | C | R175C |
| 175 | R | K | R175K |
| 170 | G | C | G170C |
| 179 | Y | C | Y179C |

Example 5

Identification of FGF21 Mutants Comprising Two Mutations

Further analysis of the homology model and data obtained from the single cysteine mutants was performed in order to identify combinations of mutants that would provide two non-naturally occurring polymer attachment sites. Following chemical modification, these FGF21 mutants have two polymers (e.g., PEG molecules) attached to the polypeptide at desired locations. As with all the FGF21 mutant polypeptides of the present invention, a polymer can also be attached to the N-terminus of the polypeptide, depending on the nature of the polymer itself. A cartoon depicting a dually PEGylated FGF21 mutant is shown graphically in FIG. 1.

A summary of FGF21 mutants comprising two mutations that were generated through this rational protein engineering approach is provided in Table 6. These double mutants incorporate a non-naturally occurring polymer attachment site, notably a cysteine. The side chains of these residues are particularly suited to chemical modification by the attachment of a polymer, such as a PEG molecule. It was recognized that in addition to the introduced non-naturally occurring polymer attachment site, a polymer could optionally be attached to the N terminal of the protein, as desired.

Since the introduced residues were designed to maintain FGF21 biological activity, these FGF21 mutants are expected to preserve FGF21 biological activity and yet still provide one or more non-naturally occurring polymer attachment sites. After chemical modification (e.g., PEGylation) these mutants are expected to have a longer half life than wild-type FGF21, while maintaining substantial in vivo potency.

The numbers of the positions given in Table 6 correspond to the residue position in the mature FGF21 protein, which consists of 181 amino acid residues. Nucleic acid sequences encoding the FGF21 mutant polypeptides listed in Table 6 below were prepared using the techniques described below.

TABLE 6

FGF21 Mutant Polypeptides Comprising Two Mutations

| Residue 1 | WT | Mutation | Residue 2 | WT | Mutation | |
|---|---|---|---|---|---|---|
| 37 | E | C | 77 | R | C | E37C, R77C |
| 120 | G | C | 125 | H | C | G120C, H125C |
| 77 | R | C | 91 | E | C | R77C, E91C |
| 77 | R | C | 125 | H | C | R77C, H125C |
| 91 | E | C | 125 | H | C | E91C, H125C |
| 77 | R | C | 120 | G | C | R77C, G120C |
| 37 | E | C | 91 | E | C | E37C, E91C |
| 91 | E | C | 175 | R | C | E91C, R175C |
| 37 | E | C | 175 | R | C | E37C, R175C |
| 91 | E | C | 120 | G | C | E91C, G120C |
| 37 | E | C | 120 | G | C | E37C, G120C |
| 77 | R | C | 175 | R | C | R77C, R175C |
| 37 | E | C | 125 | H | C | E37C, H125C |
| 37 | E | C | 69 | K | C | E37C, K69C |
| 69 | K | C | 91 | E | C | K69C, E91C |
| 120 | G | C | 175 | R | C | G120C, R175C |
| 69 | K | C | 120 | G | C | K69C, G120C |
| 69 | K | C | 125 | H | C | K69C, H125C |
| 69 | K | C | 77 | R | C | K69C, R77C |
| 125 | H | C | 175 | R | C | H125C, R175C |
| 69 | K | C | 175 | R | C | K69C, R175C |
| 37 | E | C | 170 | G | C | E37C, G170C |

Example 6

Identification of FGF21 Mutants Comprising Three Mutations

As described above, non-naturally occurring polymer attachment sites can be introduced into the wild-type FGF21 polypeptide sequence. This affords the opportunity for site-selective chemical modification at desired locations in the polypeptide. In addition, it has previously been determined that residue P171 in the wild-type FGF21 sequence is susceptible to proteolytic degradation. Accordingly, by introducing combinations of the above modifications, plus a mutation at the P171 position, FGF21 molecules having both enhanced proteolytic stability and site-specific polymer attachment sites can be generated.

Further analysis of the homology model was performed in order to identify combinations of mutants that would provide two non-naturally occurring polymer attachment sites. Following chemical modification, these mutants would have two polymers (e.g., PEG molecules) attached to the polypeptide at desired locations. As with all the FGF21 mutant polypeptides of the present invention, a polymer can also be attached to the N-terminus of the polypeptide, depending on the nature of the polymer itself. The analysis included the evaluation of a mutation at the P171 position in addition to the two introduced polymer attachment sites, which was designed to enhance the proteolytic stability of the FGF21 mutant polypeptide, and provide selected polymer attachment sites and enhanced proteolytic stability, while at the same time maintaining or enhancing the in vivo biological activity of wild-type FGF21.

In a parallel study, a select subset of single mutations from Table 5, presented in Example 4, were combined with the stability enhancing P171 mutation for the purpose of PEGylating site selectively at both the α-amino N-terminus and the introduced cysteine mutation using site-selective mixed chemistries as previously described (see U.S. Pat. No. 6,420, 339, incorporated herein by reference). These double mutants were designated R77C/P171G and H125C/P171G and are the FGF21 triple mutant, this combination of mutations serves the function of enhancing FGF21 half life via the association of two polymers (e.g., PEG molecules) with the polypeptide sequence as well as enhancing the half life via the elimination of a proteolytic cleavage site.

Since the introduced residues were designed to maintain the in vivo wild-type levels of FGF21 biological activity, these FGF21 mutants are expected to maintain FGF21 biological activity and yet still provide unique non-naturally occurring polymer attachment sites. After chemical modification (e.g., PEGylation) these mutants are expected to have a longer half life than wild-type FGF21, while maintaining significant in vivo wild-type levels of biological activity.

The numbers of the positions given in Table 7 correspond to the residue position in the mature FGF21 protein, which consists of 181 amino acid residues. Nucleic acid sequences encoding the FGF21 mutant polypeptides listed in Table 7 were prepared using the techniques described herein.

TABLE 7

| FGF21 Mutant Polypeptides Comprising Three Mutations | | | | | | | | | |
|---|---|---|---|---|---|---|---|---|---|
| Residue 1 | WT | Mutation | Residue 2 | WT | Mutation | Residue 3 | WT | Mutation | |
| 37 | E | C | 77 | R | C | 171 | P | G | E37C, R77C, P171G |
| 91 | E | C | 125 | H | C | 171 | P | G | E91C, H125C, P171G |
| 77 | R | C | 120 | G | C | 171 | P | G | R77C, G120C, P171G |
| 37 | E | C | 91 | E | C | 171 | P | G | E37C, E91C, P171G |
| 91 | E | C | 175 | R | C | 171 | P | G | E91C, R175C, P171G |
| 37 | E | C | 175 | R | C | 171 | P | G | E37C, R175C, P171G |
| 91 | E | C | 120 | G | C | 171 | P | G | E91C, G120C, P171G |
| 37 | E | C | 120 | G | C | 171 | P | G | E37C, G120C, P171G |
| 77 | R | C | 175 | R | C | 171 | P | G | R77C, R175C, P171G |
| 37 | E | C | 125 | H | C | 171 | P | G | E37C, H125C, P171G | exemplary of any other combinations that might be contemplated using the mutations disclosed in Table 5 of Example 4.

A summary of FGF21 mutants comprising two mutations, in addition to a mutation at the P171 site, that were generated through this rational protein engineering approach is provided in Table 7. These mutants incorporate two non-naturally occurring polymer attachment sites, notably cysteine. The side chains of these residues are particularly suited to chemical modification by the attachment of a polymer, such as a PEG molecule. It was recognized that in addition to the introduced non-naturally occurring polymer attachment site, a polymer could optionally be attached to the N-terminus of the protein, as desired. The triple FGF21 mutants described include not only the introduced polymer attachment sites described above, but also a proteolytic stability inducing mutation at position 171. Following chemical modification of Example 7

Preparation and Expression of FGF21 Mutant Polypeptides

Constructs encoding the FGF21 mutants listed in Tables 3 (single mutations), 4 (double mutations) and 5 (triple mutations, i.e., double mutations+P171G), collectively "FGF21 mutants" in this Example, were prepared by PCR amplification of the wild-type FGF21 expression vector as described below (the construction of the wild-type FGF21 expression vector is described in Example 1). The goal of these experiments was to generate FGF21 mutants that comprise one or more non-naturally occurring polymer attachment sites, and in some cases are resistant to proteolysis. The chemically modified forms of these FGF21 mutants would be expected to exhibit longer half lives, and in some cases also resist proteolysis.

FGF21 mutant constructs were prepared using primers having sequences that are homologous to regions upstream and downstream of a codon (or codons) to be mutated. The primers used in such amplification reactions also provided approximately 15 nucleotides of overlapping sequence to allow for recircularization of the amplified product, namely the entire vector now having the desired mutant.

An exemplary FGF21 mutant construct, encoding an FGF21 mutant having a glutamic acid residue at position 170 instead of the native glycine residue (i.e., a G170E FGF21 mutant polypeptide) was prepared using the primers shown in Table 8.

TABLE 8

PCR Primers for Preparing Exemplary FGF21 Mutant

| Primer | Sequence | SEQ ID NO: |
|---|---|---|
| Sense | 5'-ATGGTGGAACCTTCCCAGGGCCGAAGC-3' | 29 |
|  | CTCCTCGGACCCTCTGAGCATGGTGGGACCTTCCCAGGGCCGAAGCCCCA | 30 |
|  | GAGGAGCCTGGGAGACTCGTACCACCCTGGAAGGGTCCCGGCTTCGGGGT | 31 |
| Antisense | 5'-GGAAGGTTCCACCATGCTCAGAGGGTCCGA-3' | 32 |

The primers shown in Table 6 allow for the substitution of the glycine residue with a glutamic acid residue as shown below, wherein the upper sequence is the sense primer (SEQ ID NO: 29), the second and third sequences (SEQ ID NOs: 30 and 31) are portions of an FGF21 expression construct, and the fourth sequence is the antisense primer (SEQ ID NO: 32):

5'-ATGGTGGAACCTTCCCAGGGCCGAAGC

CTCCTCGGACCCTCTGAGCATGGTGGGACCTTCCCAGGGCCGAAGCCCCA

GAGGAGCCTGGGAGACTCGTACCACCCTGGAAGGGTCCCGGCTTCGGGGT

AGCCTGGGAGACTCGTACCACCTTGGAAGG-5'

FGF21 mutant constructs were prepared using essentially the PCR conditions described in Example 1. Amplification products were digested with the restriction endonuclease DpnI, and then transformed into competent cells. The resulting clones were sequenced to confirm the absence of polymerase-generated errors.

FGF21 mutants were expressed by transforming competent BL21 (DE3) or BL21 Star (Invitrogen; Carlsbad, Calif.) cells with the construct encoding a particular mutant. Transformants were grown overnight with limited aeration in TB media supplemented with 40 μg/mL kanamycin, were aerated the next morning, and after a short recovery period, were induced in 0.4 mM IPTG. FGF21 mutant polypeptides were harvested by centrifugation 18-20 hours after induction.

As a result of the bacterial expression system employed, the FGF21 mutant polypeptides were expressed with an N-terminal methionine residue.

Example 8

Purification of FGF21 and FGF21 Mutant Polypeptides from Bacteria

In the Examples that follow, FGF21 mutant polypeptides were expressed in a bacterial expression system. After expression, which is described in Example 7, FGF21 mutant polypeptides were purified as described in this Example, unless otherwise indicated.

To purify the FGF21 mutant polypeptide from bacterial inclusion bodies, double-washed inclusion bodies (DWIBs) were solubilized in a solubilization buffer containing guanidine hydrochloride and DTT in Tris buffer at pH 8.5 and then mixed for one hour at room temperature, and the solubilization mixture was added to a refold buffer containing urea, arginine, cysteine, and cystamine hydrochloride at pH 9.5 and then mixed for 24 hours at 5° C. (see, e.g., Clarke, 1998, *Curr. Opin. Biotechnol.* 9: 157-63; Mannall et al., 2007, *Biotechnol. Bioeng.* 97: 1523-34; Rudolph et al., 1997, "Folding Proteins," in *Protein Function: A Practical Approach* (Creighton, ed., New York, IRL Press), pp 57-99; and Ishibashi et al., 2005, *Protein Expr. Purif.* 42: 1-6).

Following solubilization and refolding, the mixture was filtered through a 0.45 micron filter. The refold pool was then concentrated approximately 10-fold with a 5 kD molecular weight cut-off Pall Omega cassette at a transmembrane pressure (TMP) of 20 psi, and diafiltered with 3 column volumes of 20 mM Tris, pH 8.0 at a TMP of 20 psi.

The clarified sample was then subjected to anion exchange (AEX) chromatography using a Q Sepharose HP resin. A linear salt gradient of 0 to 250 mM NaCl in 20 mM Tris was run at pH 8.0 at 5° C. Peak fractions were analyzed by SDS-PAGE and pooled.

The AEX eluate pool was then subjected to hydrophobic interaction chromatography (HIC) using a Phenyl Sepharose HP resin. Protein was eluted using a decreasing linear gradient of 0.6 M to 0 M ammonium sulfate with 20 mM TRIS at pH 8.0 and ambient temperature. Peak fractions were analyzed by SDS-PAGE (Laemmli, 1970, *Nature* 227: 680-85) and pooled.

The HIC pool was concentrated with a 5 kD molecular weight cut-off Pall Omega 0.2 m² cassette to 7 mg/mL at a TMP of 20 psi. The concentrate was diafiltered with 5 column volumes of 20 mM TRIS, pH 8.0 at a TMP of 20 psi, and the recovered concentrate was diluted to about 5 mg/mL. Finally, the solution was filtered through a 0.22 μm cellulose acetate filter.

Example 9

Chemical Modification of FGF21 Mutants

Variants of FGF21 having cysteine substituted at the selected positions shown in Tables 3-5 were produced as described in Example 7, and the molecules were then subjected to a PEGylation reaction with a 20 kDa methoxy-PEG-maleimide. Unless indicated otherwise, all PEGylated FGF21 wild-type and mutant polypeptides disclosed herein comprise one or more 20 kDa methoxy PEG maleimide polymers.

Figure 2:
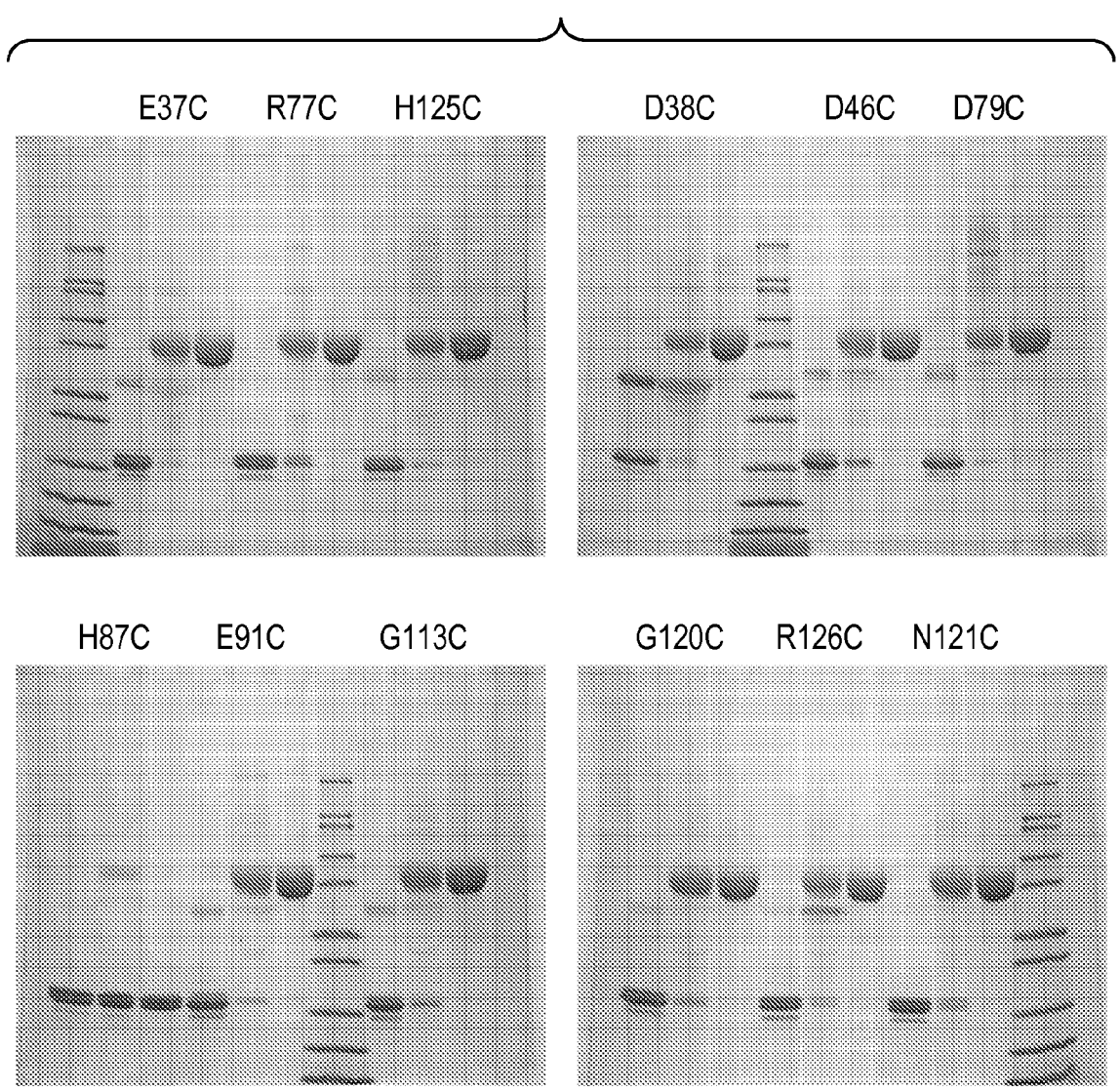
FIG. 2 comprises four SDS-PAGE gels, showing the degree of PEGylation of nine FGF21 mutants having a single engineered polymer attachment site that have been chemically modified with PEG, namely E37C, R77C and H125C (upper left), D38C, D46C and D79C (upper right), H87C, E91C, G113C (lower left) and G120C, R126C, N121C (lower right).
Figure 3:
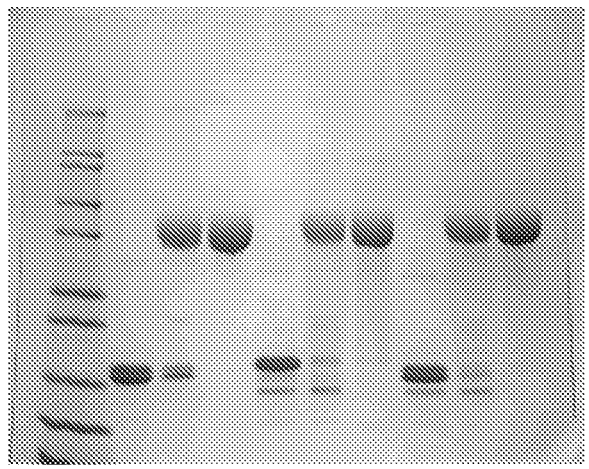
FIG. 3 comprises an SDS-PAGE gel, showing the degree of PEGylation of three FGF21 mutants having a single engineered polymer attachment site that have been chemically modified with a 20 kDa methoxy PEG maleimide molecule, namely K69C, R175C and Y179C.

The partially purified FGF21 molecules were then reduced using 5 molar equivalents of TCEP for 30 minutes at 25° C. The reduced FGF21 was then buffer exchanged in to 10 mM imidazole, pH 7.5 using a GE Healthcare Sephadex G25M column. The buffer exchanged FGF21 was then reacted with 5 molar equivalents of 20 kDa methoxy-PEG-maleimide for 30 minutes at 25° C. The resulting reaction mixture was then subjected to ion-exchange chromatography to isolate the mono-PEGylated species from multi-PEGylated and un-PEGylated molecules. Most of the FGF21 mutant polypeptides reacted well with the methoxy-PEG-maleimide and produced principally mono-PEGylated products in high yield (FIGS. 2 and 3).

For production of the Tethered Molecules, partially purified FGF21 molecules were reduced using 5 molar equivalents of TCEP for 30 minutes at 25° C. The reduced FGF21 was then buffer exchanged in to 10 mM imidazole, pH 7.5 using a GE Healthcare Sephadex G25M column. The buffer exchanged FGF21 was then reacted with 0.45 molar equivalents of 20 kDa PEG bis-maleimide for 60 minutes at 4° C. The resulting reaction mixture was then subjected to ion-exchange chromatography to isolate the Tethered Molecule from other undesirable reaction products. Frequently an additional ion-exchange purification step was required, which was accomplished by diluting the first ion-exchange pool in about 4 volumes of water and reapplying to the ion-exchange column.

Alternatively amine specific coupling to the N-terminus was achieved by reductive alkylation using methoxy-PEG-propionaldehyde as previously described (see U.S. Pat. No. 5,824,784). Briefly, mutant FGF21 at about 2 mg/ml was reacted overnight at 4 degrees C., with a 5-fold molar excess of 20 kD mPEG-propionaldehyde in acetate buffer pH 5.5 and 10 mM sodium cyanoborohydride. N-terminal PEGylation of any of the FGF21 wild-type and mutant molecules described herein can be achieved using this strategy.

When amine specific dual PEGylation was required at both the N-terminus and a mutant lysine, methoxyPEG-NHS(N-hydroxysuccinimidyl ester) was used. Briefly, mutant FGF21 at about 2 mg/ml was reacted for about 2 hours at 4° C. with a 5-fold molar excess (PEG:amino group) of 20 kD mPEG-NHS in bicine buffer, pH 7.5.

When applying a mixed chemistry approach to dual PEGylate FGF21 mutants at both the N-terminus and a mutant Cys position, both methoxy-PEG-propionaldehyde and methoxy-PEG-maleimide were used sequentially as previously described (see U.S. Pat. No. 6,420,339). Briefly, mutant FGF21 at about 2 mg/ml was reacted for about 2 hours with a 1.5-fold molar excess of 20 kD mPEG-maleimide in phosphate buffer at pH 6.5 at 4° C., then the pH was adjusted to about pH 5 and a 5-fold excess of 20 kD mPEG-propionaldehyde added with 10 mM sodium cyanoborohydride. The final reaction was allowed to continue at 4° C. overnight.

Purification of all the different reaction mixtures was by anion exchange chromatography in Tris buffer at pH 8 as previously described.

Example 10

In Vitro Activity of FGF21 Mutant Polypeptides and Chemically Modified FGF21 Mutant Polypeptides PEGylated FGF21 mutant polypeptides were then subjected to an in vitro assay to assess their activity, as compared to the un-PEGylated form of the FGF21 mutant polypeptide and N-terminally PEGylated FGF21.

One goal of these experiments was to identify FGF21 mutant polypeptides and chemically-modified FGF21 mutant polypeptides that preserve FGF21 activity in an ELK-luciferase in vitro assay. ELK-luciferase assays were performed using a recombinant human 293T kidney cell system, in which the 293T cells overexpress beta-klotho and luciferase reporter constructs. Beta-klotho is a co-receptor that is required by FGF21 for activation of its FGF receptors. The FGF receptors used in this assay are endogenous levels of FGF receptors expressed in 293T kidney cell. The luciferase reporter constructs contain sequences encoding GAL4-ELK1 and a luciferase reporter driven by a promoter containing five tandem copies of the Gal4 binding site (5×UAS-Luc). Luciferase activity is regulated by the level of phosphorylated Erk/ELK1, and is used to indirectly monitor and quantify FGF21 activity.

ELK-luciferase assays were performed by culturing the 293T cells in the presence of different concentrations of wild-type FGF21 or FGF21 mutant polypeptide for 6 hours, and then assaying the cell lysates for luciferase activity. FIGS. 4-6 and Tables 3-5 summarize the in vitro results obtained for several exemplary FGF21 mutant polypeptides, including those having one, two or three mutations.

Example 10.A

EC50 Values for PEGylated FGF21 Mutant Polypeptides Comprising One Mutation

Table 9 below summarizes the EC50 values of various FGF21 mutant polypeptides comprising two mutations, which introduce one non-naturally occurring polymer attachment sites at a specific, known location.

Various FGF21 mutant polypeptides were generated and the activity determined in the in vitro ELK-luciferase assay described herein. Table 9 summarizes the data obtained:

TABLE 9

Summary of EC50 for PEGylated FGF21 Mutant Polypeptides Comprising One Mutation

| Mutation | EC50 (nM) | WT EC50 (nM) | N-PEG20 EC50 (nM) |
| --- | --- | --- | --- |
| H125C | 4.5 | 2.8 | 36.7 |
| R77C | 4.9 | 3.9 | 43.3 |
| K69C | 5.3 | 2.8 | 36.7 |
| G120C | 6.0 | 2.8 | 36.7 |
| E37C | 6.9 | 3.9 | 43.3 |
| R175C | 7.9 | 0.9 | 21.5 |
| E91C | 8.3 | 3.9 | 43.3 |
| N121C | 9.2 | 3.9 | 43.3 |
| R126C | 10.0 | 2.8 | 36.7 |
| G113C | 12.0 | 3.9 | 43.3 |
| D38C | 13.1 | 2.8 | 36.7 |
| D79C | 20.4 | 3.4 | 40.0 |
| D46C | 27.8 | 3.9 | 43.3 |
| Y179C | 287.1 | 1.1 | 21.5 |

Table 9 summarizes the effect of PEGylation on the in vitro activity of some of the various FGF21 mutant polypeptides of the present invention.

FIGS. 4, 5 and 6 graphically depict the results and EC50 values for several PEGylated FGF21 mutants comprising a single point mutation. FIGS. 4 and 5 contain data on several of the FGF21 mutants for which data is presented in Table 9. More particularly, the upper plot of FIG. 4 shows the results of the ERK-luciferase assay performed on PEGylated E37C, R77C, E91C mutants and N-terminally PEGylated wild-type FGF21, as well as un-PEGylated FGF21. In the lower plot in FIG. 4, data is presented on PEGylated G113C, N121C, D46C mutants and N-terminally PEGylated wild-type FGF21, as well as un-PEGylated wild-type FGF21.

Turning to FIG. 5, in the upper plot data is presented for H125C, G120C, R126C mutants and N-terminally PEGylated wild-type FGF21, as well as un-PEGylated wild-type FGF21. In the lower plot, data is presented for D79C, D38C mutants and N-terminally PEGylated wild-type FGF21, as well as un-PEGylated wild-type FGF21.

Continuing with the upper plot of FIG. 6, graphical data is presented for PEGylated K69C and D79C mutants, as well as N-terminally PEGylated wild-type FGF21, and for un-PEGylated wild-type FGF21. In the lower plot of FIG. 6, data is presented for PEGylated R175C and Y179C mutants and N-terminally PEGylated wild-type FGF21, as well as un-PEGylated wild-type FGF21. Surprisingly, many of these molecules have in vitro activity close to that of the unPEGylated molecule.

Example 10.B

EC50 Values for Selected Arg/Lys FGF21 Mutants

As described in Example 3, a series of FGF21 mutant polypeptides was generated in which naturally-occurring polymer attachment sites (e.g., PEGylation sites) were removed by mutagenesis. In these FGF21 mutants reactive Lys groups were first mutated to arginine, leaving only the N-terminus α-amino group available for PEGylation. Next select arginine residues, either native or mutant, were converted one by one to lysine, thereby introducing a secondary PEGylation site at defined positions on the FGF21 surface. One goal of this strategy was to generate FGF21 mutant polypeptides in which a polymer (e.g., a PEG molecule) would be conjugated at one or more specific, known locations.

Various arginine/lysine FGF21 mutant polypeptides were generated and the activity determined in the in vitro ELK-luciferase assay described herein. Table 10 summarizes the data obtained:

TABLE 10

Summary of EC50 for PEGylated FGF21 Mutant Polypeptides Comprising Lysine/Arginine Mutations

| Construct | Type of PEG | In Vitro Activity $EC_{50}$ (nM) |
| --- | --- | --- |
| Native FGF21 | No PEG | 3 |
| Native FGF21 (N-terminus) | 1 x 20k | 43.3 |
| Native FGF21 (random) | 2 x 20k | 200 |
| FGF21(all K to all R) | 1 x 20k | nd |
| FGF21(all K to all R, R36K) | 2 x 20k | 73 |
| FGF21(all K to all R, R77K) | 2 x 20k | 175 |
| FGF21(K56/59/69R) | 2 x 20k | 500 |
| FGF21(K all R, R126K) | 2 x 20k | 38 |
| FGF21(K59R/K69R/K122R) | 2 x 20k | 499 |
| FGF21(K56R/K69R/K122R) | 2 x 20k | 215 |
| FGF21(K56R/K59R/K122R) | 2 x 20k | 531 |
| FGF21(all K to all R, R72K) | 2 x 20k | >1000 |
| FGF21(all K to all R, R175K) | 2 x 20k | >1000 |

Example 10.0

EC50 Values for Selected PEGylated FGF21 Mutant Polypeptides Comprising Two Mutations The activity of a number of FGF21 mutant polypeptides comprising two mutations was also examined in the ERK-luciferase assay described herein. These mutants were engineered to introduce two non-naturally occurring polymer attachment sites (in the form of a cysteine residue) and a mutation providing enhanced proteolytic stability (P171G) into the wild-type FGF21 sequence.

Various FGF21 mutant polypeptides were generated and the activity determined in the in vitro ELK-luciferase assay described herein. EC50 values from those experiments are shown below in Table 11.

TABLE 11

EC50 Values for Selected Chemically Modified FGF21 Mutant Polypeptides Comprising Two Mutations

| Mutations | EC50 (nM) |
| --- | --- |
| Native FGF21 | 3 |
| N-term PEG20K | 37 |
| E37C, R77C | 21 |
| G120C, H125C | 23 |
| R77C, E91C | 26 |
| R77C, H125C | 30 |
| E91, H125C | 32 |
| R77C, G120C | 34 |
| E37C, E91C | 36 |
| E91C, R175C | 46 |
| E37C, R175C | 50 |
| E91C, G120C | 54 |
| E37C, G120C | 55 |
| R77C, R175C | 62 |
| E37C, H125C | 64 |
| E37C, K69C | 67 |
| K69C, E91C | 69 |
| G120C, R175C | 118 |
| K69C, G120C | 119 |
| K69C, H125C | 164 |
| K69C, R77C | 180 |
| H125C, R175C | 200 |
| K69C, R175C | 318 |
| E37C, G170C | 163 |

In parallel, dual-PEGylated FGF21 mutants were prepared using single cysteine mutants derived from Example 10A, but also carrying the stability enhancing P171G mutation. These mutants were site-selectively PEGylated at both the N-terminus and the engineered cysteine using the mixed PEGylation chemistry as previously described (see U.S. Pat. No. 6,420, 339). Because the mixed PEGylation chemistry allows the discrimination between the N-terminus and cysteine conjugation sites, it is also possible to site-selectively couple different polymers to different sites. In this case, a series of conjugates were prepared wherein combinations of 5 kDa, 10 kDa and 20 kDa polymers were coupled to the N-terminus and a 20 kDa polymer was consistently coupled to the cysteine mutant. This allowed assessment of the impact of N-terminal PEGylation on FGF21 in vitro activity. These conjugates were all tested in the in vitro ELK-luciferase assay described here. The results are presented in Table 12.

TABLE 12

EC50 Values for Selected Chemically Modified FGF21 Mutant Polypeptides Comprising a Cysteine Mutation and a P171G Mutation

| Mutation | Type of PEG | EC50 (nM) |
| --- | --- | --- |
| R77C, P171G | 2 x 20k | 64 |
| H125C, P171G | 2 x 20k | 152 |
| H125C, P171G | 1 x 10k, 1 x 20k | 65 |
| H125C, P171G | 1 x 5k, 1 x 20k | 30 |

Example 10.D

EC50 Values for Selected Chemically Modified FGF21 Mutant Polypeptides Comprising Three Mutations The activity of a number of FGF21 mutant polypeptides comprising three mutations was also examined in the ERK-luciferase assay described herein. These mutants were engineered to introduce two non-naturally occurring polymer attachment sites (in the form of a cysteine residue) and a mutation providing enhanced proteolytic stability (P171G) into the wild-type FGF21 sequence.

Various FGF21 mutant polypeptides were generated and the activity determined in the in vitro ELK-luciferase assay described herein. Table 13 summarizes the data obtained:

TABLE 13

EC50 Values for Selected Chemically Modified FGF21 Mutant Polypeptides Comprising Three Mutations

| Mutations | Type of PEG | EC50 (nM) |
|---|---|---|
| E37C, R77C, P171G | 2X 20 kDa | 27 |
| E91, H125C, P171G | 2X 20 kDa | 37 |
| R77C, G120C, P171G | 2X 20 kDa | 35 |
| E37C, E91C, P171G | 2X 20 kDa | 30 |
| E91C, R175C, P171G | 2X 20 kDa | 155 |
| E37C, R175C, P171G | 2X 20 kDa | 162 |
| E91C, G120C, P171G | 2X 20 kDa | 34 |
| E37C, G120C, P171G | 2X 20 kDa | 35 |
| R77C, R175C, P171G | 2X 20 kDa | ND |
| E37C, H125C, P171G | 2X 20 kDa | 37 |

Surprisingly, the data indicates that the majority of these dual-PEGylated FGF21 mutant polypeptides have activity surpassing the N-terminally mono-PEGylated molecule.

Example 11

EC50 Values for Selected FGF21 Tethered Molecules

Figure 7:
FIG. 7 is a cartoon depicting a Tethered Molecule of the present invention.

The Tethered Molecules of the present invention comprise two FGF21 polypeptide sequences tethered together by a linker molecule. FIG. 7 graphically depicts an example of a Tethered Molecule. As described herein, it was predicted that these Tethered Molecules would provide longer half-lives, while still retaining a desirable level of biological activity.

Various Tethered Molecules were generated and the activity determined in the in vitro ELK-luciferase assay described here. The Tethered Molecules generated comprise FGF21 mutants in which the mutation introduces a linker attachment site. Several of the FGF21 mutants were double mutants and include the P171G mutation to enhance proteolytic stability. Conditions and procedures for this in vitro study were the same as those in Example 10. Table 14 summarizes the data obtained:

TABLE 14

EC50 Values for Selected FGF21 Tethered Molecules

| Mutations | Linker | EC50 (nM) |
|---|---|---|
| H125C, P171G | 20 kDa PEG | 0.21 |
| R77C, P171G | 20 kDa PEG | 0.25 |
| G120C, P171G | 20 kDa PEG | 0.51 |
| E37C, P171G | 20 kDa PEG | 0.36 |
| R175C, P171G | 20 kDa PEG | 0.36 |
| E91C, P171G | 20 kDa PEG | 0.20 |
| G170C | 20 kDa PEG | 0.47 |
| P171C | 20 kDa PEG | 0.21 |

It can be seem from the data in Table 14 that the Tethered Molecules possess a surprisingly high in vitro activity equal to or exceeding that of the unPEGylated molecule which, for reference, was determined to be 0.63.

Example 12

In Vivo Activity of Chemically-Modified FGF21 Mutant Polypeptides

FGF21 possesses a number of biological activities, including the ability to lower blood glucose, insulin, triglyceride, or cholesterol levels; reduce body weight; or improve glucose tolerance, energy expenditure, or insulin sensitivity. Following the initial in vitro evaluation described in Example 10, PEGylated FGF21 mutant polypeptides were further analyzed for in vivo FGF21 activity. PEGylated FGF21 polypeptides were introduced into insulin resistant ob/ob mice, and the ability of a particular PEGylated FGF21 polypeptide to lower blood glucose was measured. The procedure for the in vivo work was as follows.

The PEGylated FGF21 polypeptide to be tested was injected intraperitoneally into an 8 week old ob/ob mice (Jackson Laboratory), and blood samples were obtained at various time points following a single injection, e.g., 0, 6, 24, 72, 120, and 168 hours after injection. Blood glucose levels were measured with a OneTouch Glucometer (LifeScan, Inc. Milpitas, Calif.), and the results expressed as a percent change of blood glucose relative to the baseline level of blood glucose (i.e., at time 0).

The FGF21 mutants were generated as described herein and were chemically modified by the addition of two 20 kDa methoxy PEG maleimide molecules, one at each of the introduced polymer attachment sites, which were typically cysteine residues. The mutations were selected so as to provide discrete, known attachment points for two PEG molecules. PEGylation of the FGF21 mutants was achieved using the methods described herein.

Example 12.A

In Vivo Activity of N-Terminally PEGylated Wild-Type FGF21

Figure 8:
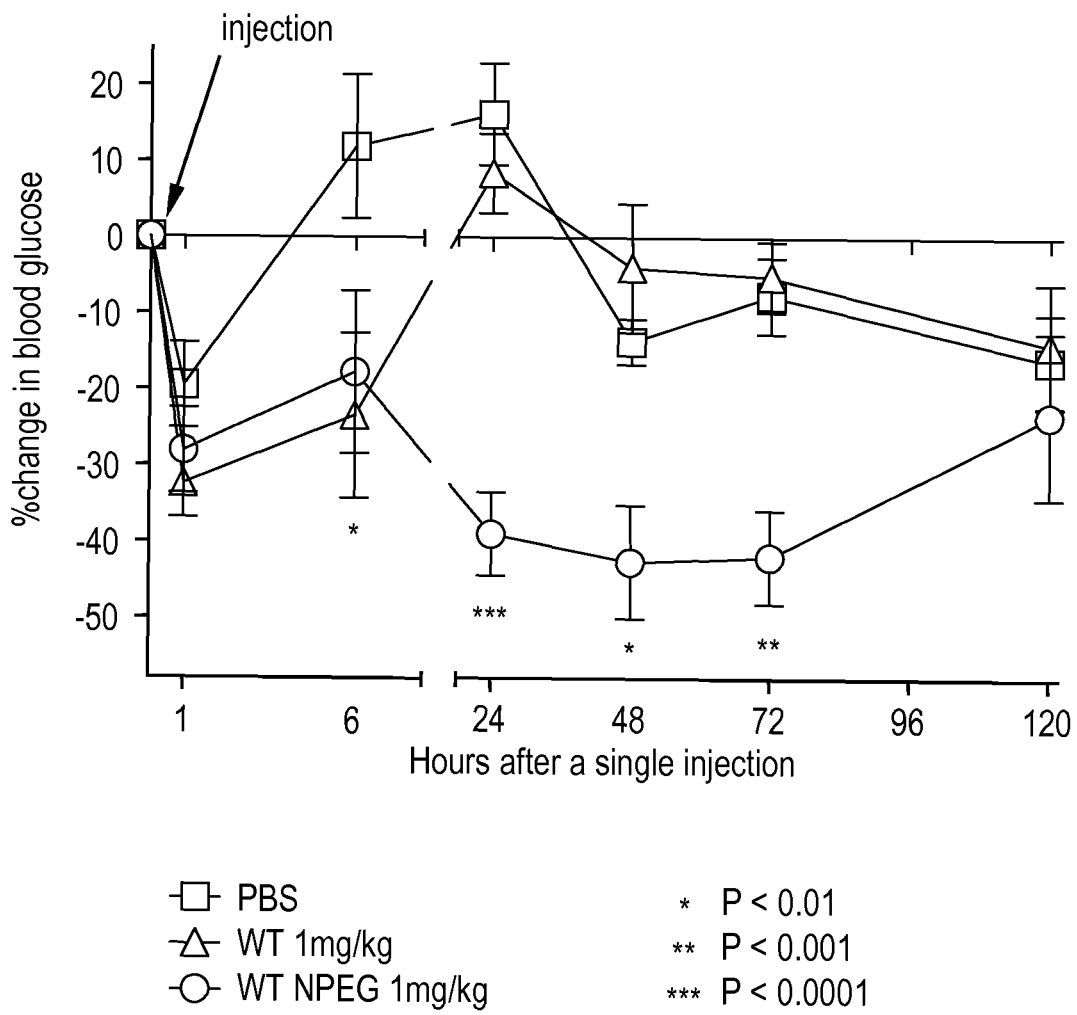
FIG. 8 is a plot depicting the percent change in blood glucose levels in mice from time 0 after a single injection of vehicle (PBS), wild-type FGF21 or N-terminally PEGylated wild-type FGF21.

Wild-type FGF21 that was chemically modified by PEGylation at the N-terminus of the polypeptide was studied in an ob/ob mouse model. Un-PEGylated wild-type FGF21 was also studied in the same experiment and PBS was used as a control. A single 20 kDa methoxy PEG maleimide molecule was used to N-terminally PEGylate wild-type FGF21. FIG. 8 demonstrates the results of this experiment.

Both native and N-terminally PEGylated wild-type FGF21 reduced blood glucose levels by 30-40% after a single injection. However, the blood glucose levels returned to baseline 24 hours after the injection of native wild-type FGF21. In contrast, N-terminally PEGylated wild-type FGF21 has sustained blood glucose-lowering activity for at least 72 hours. The results of this study indicate PEGylation of wild-type FGF21 prolongs the pharmacodynamic effects of native molecule.

Figure 9:
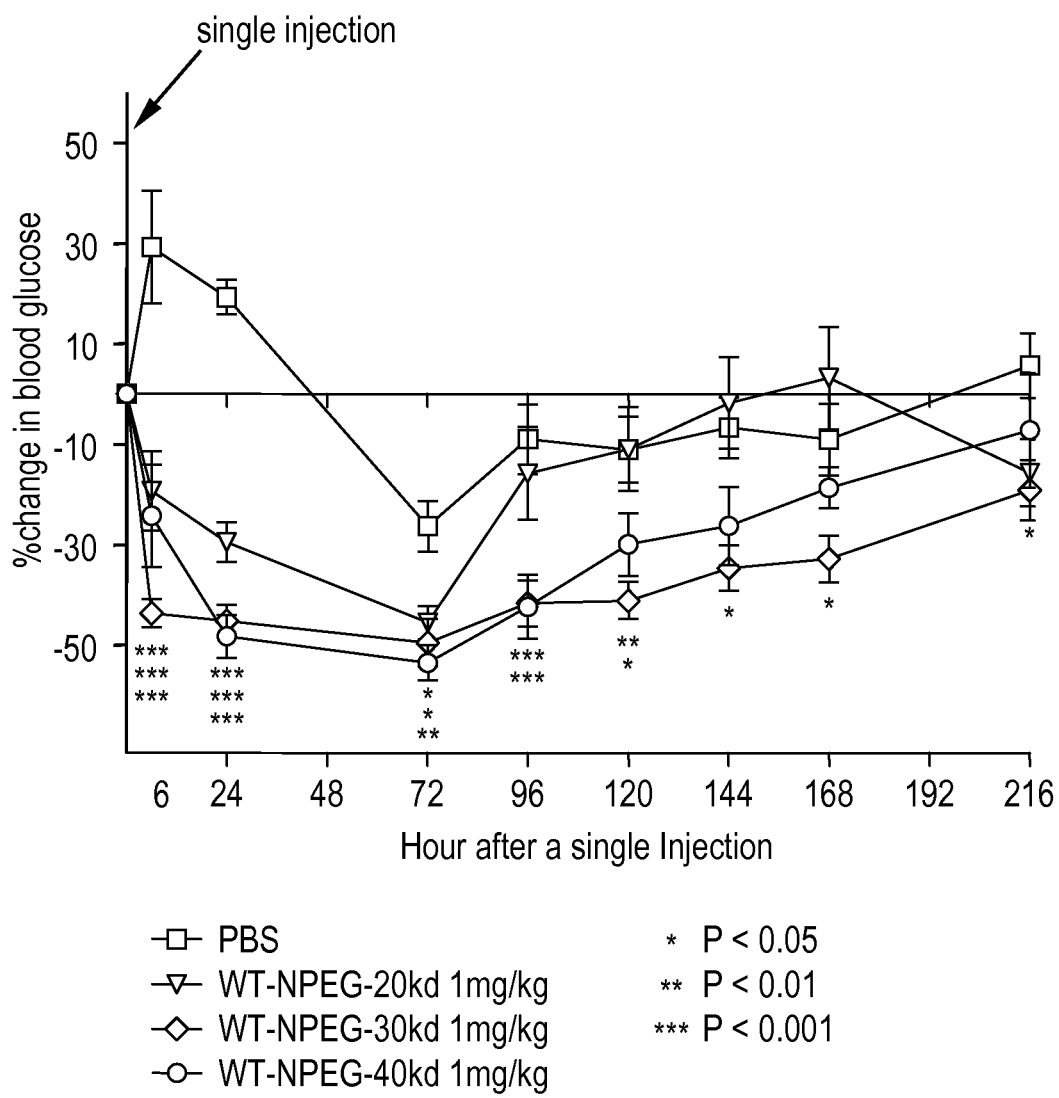
FIG. 9 is a plot depicting the percent change in blood glucose levels in mice from time 0 after a single injection of vehicle (PBS), or wild-type FGF21 that was N-terminally PEGylated with 20, 30 or 40 kDa methoxy PEG maleimide molecules.

Turning to FIG. 9, a dose response study was performed in an ob/ob mouse model using wild-type FGF21, which was PEGylated at the N-terminus with a 20, 30 or 40 kDa PEG molecule. FIG. 9 demonstrates that 30 and 40 kDa PEG molecules have greater and longer glucose lowering efficacy compared with 20 kDa PEG molecule, suggesting PEG size is positively correlated with in vivo pharmacodynamic effects.

Example 12.A.1

In Vivo Activity of Selected Chemically Modified FGF21 Mutant Polypeptides Conjugated at Both the N-Terminus and an Introduced Polymer Attachment Site Several chemically modified mutants of FGF21 that were site-selectively PEGylated at both the N-terminus and a second engineered site were studied in a mouse ob/ob model. These dual-PEGylated FGF21 constructs were all PEGylated at the N-terminus and a second site comprising either an engineered lysine as described in Example 4 or an engineered cysteine as described in Example 6.

A similar experiment was performed using a different group of PEGylated FGF21 mutant polypeptides. FIG. 10 comprises two plots showing the percent change in blood glucose levels of mice injected with vehicle (PBS), or the PEGylated forms of FGF21 mutants comprising polymer attachment mutations, namely FGF21 R77C, which was also N-terminally PEGylated, and FGF21 R126K, which was also N-terminally PEGylated (upper plot), and N-terminally PEGylated F77/P171G (lower plot), which were also PEGylated at the introduced polymer attachment sites. 20 kDa methoxy PEG maleimide molecules were used. The results of this experiment again confirm that the dually PEGylated FGF21 mutants demonstrate an enhanced pharmacodynamics relative to the wild type FGF21 protein with sustained glucose-lowering for at least 120 hours.

Example 12.B

In Vivo Activity of Selected Chemically Modified FGF21 Mutant Polypeptides Comprising Two or Three Mutations A number of chemically modified FGF21 mutant polypeptides were studied in a mouse ob/ob model. These mutants were chemically modified by the addition of two 20 kDa methoxy PEG maleimide molecules, one at each of the introduced cysteine residues, and in the case of FGF21 mutant polypeptides comprising a single mutation, at the N terminus of the polypeptide. The mutations were selected so as to provide discrete known attachment points for one or more PEG molecules. Some FGF21 mutants also included the P171G mutation to enhance proteolytic resistance. The PEGylated FGF21 mutant polypeptides were injected into the mice and the mice bled at intervals over a 9 day study.

Example 12.B.1

Effect on Glucose Levels

Figure 11:
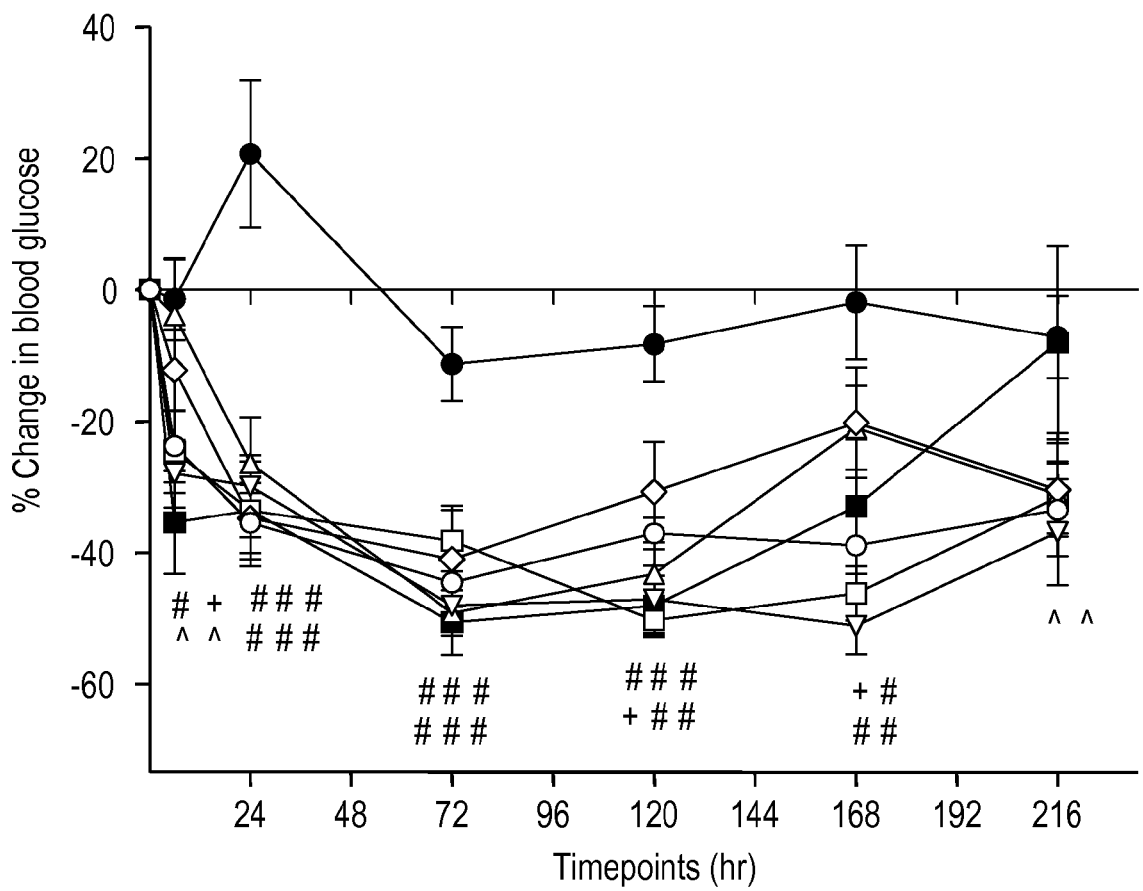
FIG. 11 is a plot showing the percent change in blood glucose levels in mice from time 0 after a single injection of vehicle (10 mM potassium phosphate, 5% sorbitol, pH 8) or FGF21 mutant polypeptides which were dually PEGylated with 20 kDa methoxy PEG maleimide molecules at introduced polymer attachment sites, namely E91C/H125C, E91C/R175C, E37C/G120C, E37C/H125C, and E37C/R175C; a fusion comprising an Fc molecule and a P171G FGF21 mutant polypeptide was also studied.

An experiment was performed using yet another group of PEGylated FGF21 mutant polypeptides. FIG. 11 is plot showing the percent change in blood glucose levels of mice injected with vehicle (PBS), or the dually PEGylated forms of FGF21 mutants comprising the mutations, namely E91/H125C, E91C/R175C, E37C/G120C, E37C/H125C, E37C/R175C; unPEGylated Fc-G170E FGF21 was also studied. 20 kDa methoxy PEG maleimide molecules were used. The results of this experiment again confirm that the dually PEGylated FGF21 mutants demonstrate an enhanced pharmacodynamics relative to the wild type FGF21 protein.

Figure 12:
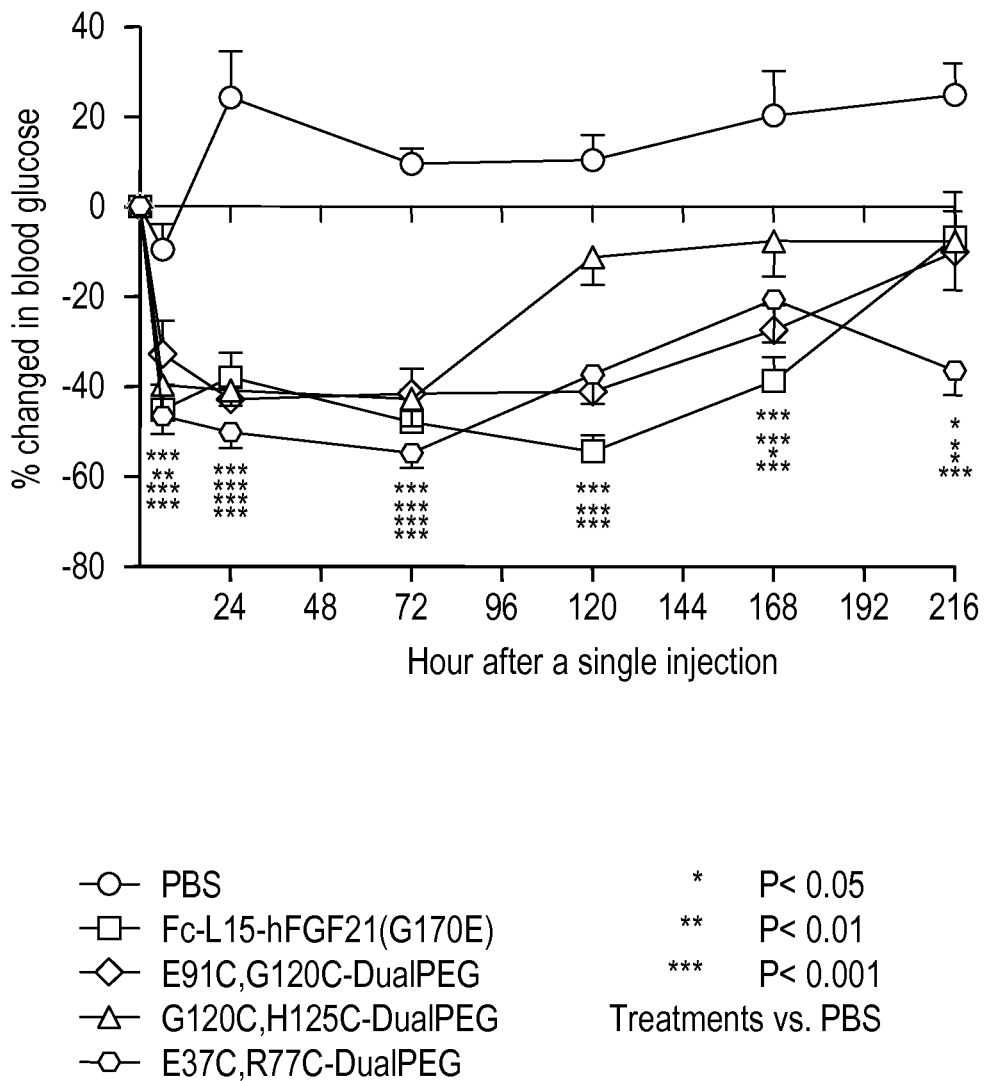
FIG. 12 is a plot showing the percent change in blood glucose levels in mice from time 0 after a single injection of vehicle (10 mM potassium phosphate, 5% sorbitol, pH 8) or FGF21 mutant polypeptides which were dually PEGylated with 20 kDa methoxy PEG maleimide molecules at introduced polymer attachment sites, namely E91C/H121C, G120C/H125C, or E37C/R77C; a fusion comprising an Fc molecule and a G170E FGF21 mutant polypeptide was also studied.

A similar experiment was performed using yet another group of PEGylated FGF21 mutant polypeptides. FIG. 12 is a plot showing the percent change in blood glucose levels of mice injected with vehicle (PBS), or the dually PEGylated forms of FGF21 mutants comprising the mutations, namely N-terminally PEGylated R77C which was also PEGylated at the introduced polymerization site, N-terminally PEGylated R126K which was also PEGylated at the introduced polymerization site, E91/G120C, G120C/H125C, and E37C/R77C; unPEGylated Fc-G170E FGF21 was also studied. 20 kDa methoxy PEG maleimide molecules were used. The results of this experiment confirm that the dually PEGylated FGF21 mutants demonstrate enhanced pharmacodynamics relative to the wild-type FGF21 protein.

Figure 13:
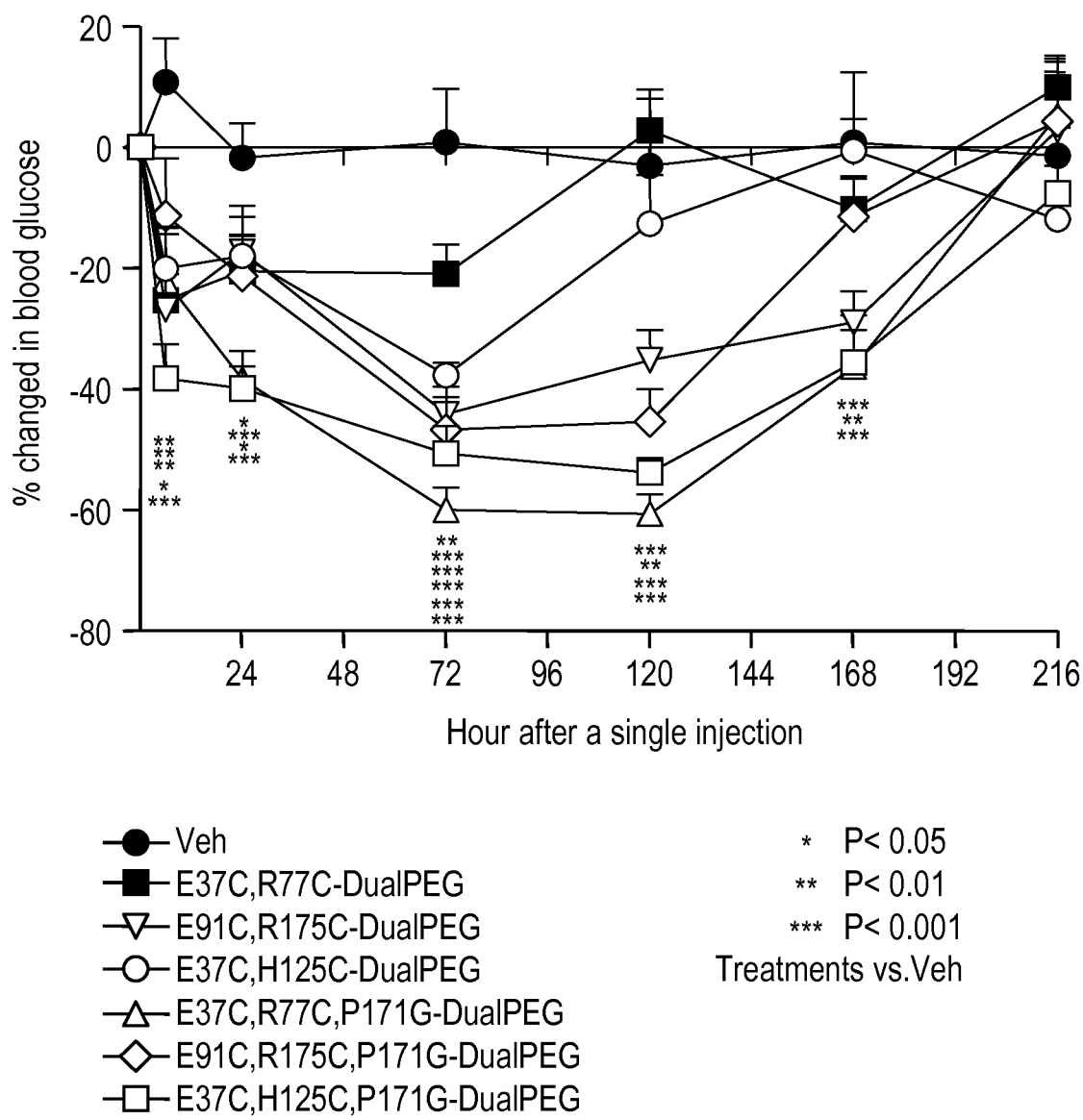
FIG. 13 is a plot showing the percent change in blood glucose levels in mice from time 0 after a single injection of vehicle (10 mM potassium phosphate, 5% sorbitol, pH 8) or FGF21 mutant polypeptides which were dually PEGylated with 20 kDa methoxy PEG maleimide molecules at introduced polymer attachment sites, namely E37C/R77C, E91C/R175C, E37C/H125C, E37C/R77C/P171G, E91C/R77C/P171G and E37C/R125C/P171G.

In another experiment, FIG. 13 shows the effect of the PEGylated FGF21 mutants on the blood glucose levels of the mice over the course of a 9 day study. This data demonstrates that the PEGylated molecules have enhanced in vivo potency compared to that of the native molecule. In FIG. 13, the results were generated with PEGylated E37C/R77C, E91C/R175C, E37C/H125C, E37C/R77C/P171G, E91C/R175C/P171G, and E37C/H125C/P171G FGF21 mutants, which were dually PEGylated at the introduced polymer attachment sites. The FGF21 mutants were modified with two 20 kDa methoxy PEG maleimide molecules in this study, and the vehicle used was 10 mM potassium phosphate, 5% sorbitol, pH 8.

As shown in FIG. 13, the three double mutant dually PEGylated molecules E37C/R77C; E91C/R175C; E37C/H125C reduced blood glucose levels, and the effects were maintained for 72 hours after a single injection. Interestingly, introducing P171G mutation further prolonged the in vivo actions and the maximal glucose-lowering activities were maintained for additional 2 days with total duration of action of 120 hours.

Figure 14:
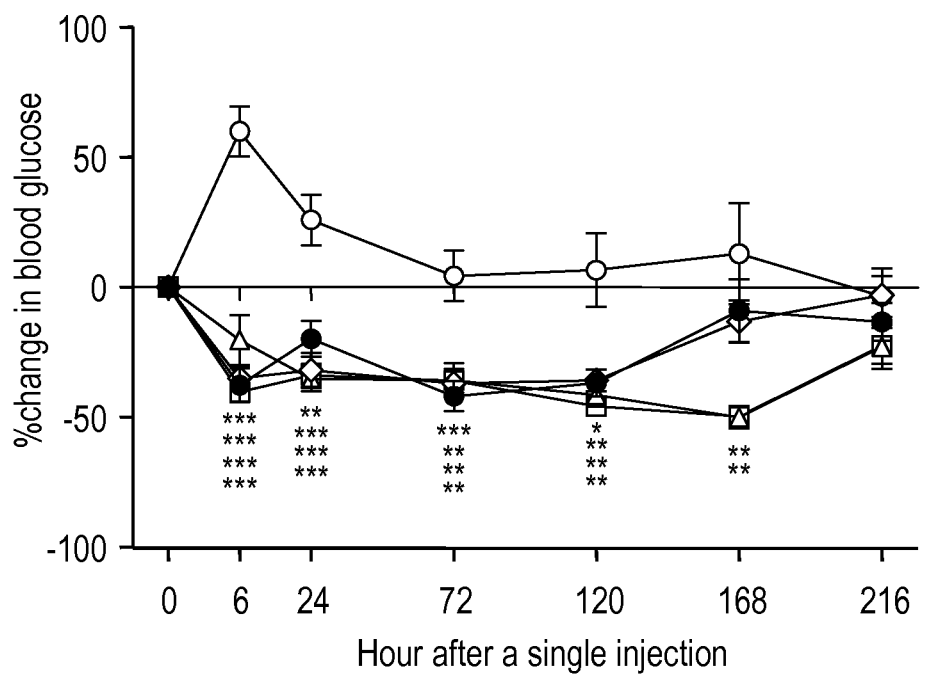
FIG. 14 is a plot showing the percent change in blood glucose levels in mice from time 0 after a single injection of vehicle (10 mM potassium phosphate, 5% sorbitol, pH 8), FGF21 mutant polypeptides which were dually PEGylated with 20 kDa methoxy PEG maleimide molecules at introduced polymer attachment sites, namely E37C/R77C/P171G and E91C/R125C/P171G, or Tethered Molecules comprising two identical FGF21 mutant polypeptides having the same introduced mutations, namely R77C/P171G (2×) and R78C/P172G (2×), which were joined together via a 20 kDa methoxy PEG maleimide molecules.

Additionally, the glucose lowering ability of several FGF21 polypeptides comprising three mutations were studied alongside several Tethered Molecules. The triple mutants used were E37C/R77C/P171G and E91C/H125C/P171G; the Tethered Molecules comprised two identical FGF21 mutant polypeptides comprising two mutations, namely E37C/P171G and R77C/P171G. 20 kDa methoxy PEG maleimide molecules were used for the dually PEGylated forms of FGF21, as well as for the linker molecule in the Tethered Molecule. The results of this experiment are shown in FIG. 14. Compared with the Tethered FGF21 mutants, the dually PEGylated mutants have further enhanced pharmacodynamics. The glucose lowering activity of the dually PEGylated mutants sustained for at least 168 hours as compared to 120 hours with the Tethered FGF21 mutants.

Figure 15:
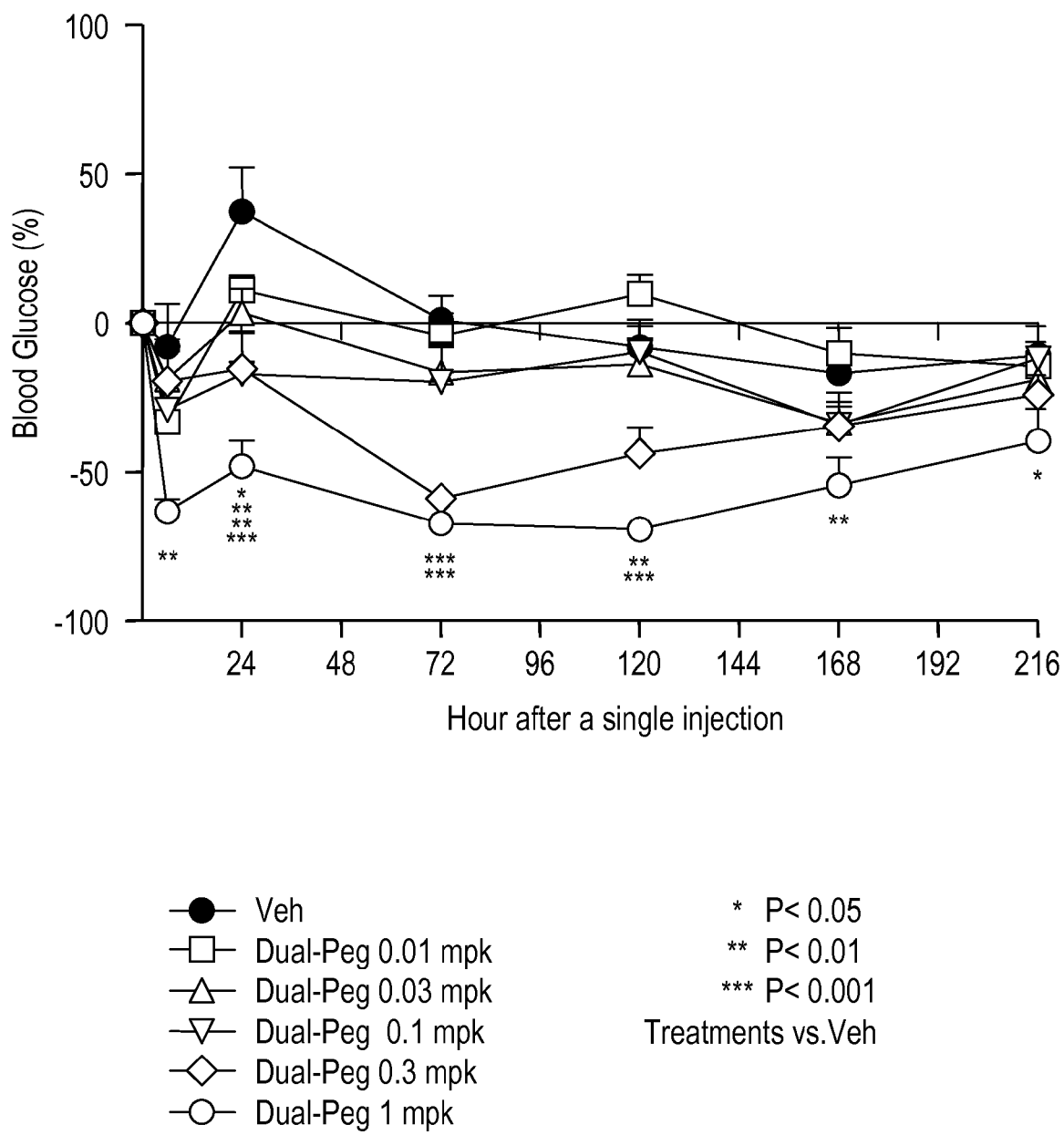
FIG. 15 is a plot showing the percent change in blood glucose levels in mice as a function of dose from time 0 after a single injection of vehicle (10 mM Tris HCl, 150 mM NaCl, pH 8.5), or an FGF21 mutant polypeptide which was dually PEGylated with 20 kDa methoxy PEG maleimide molecules at introduced polymer attachment sites, namely E37C/R77C/P171G, and administered at doses of 0.01 mg/kg, 0.03 mg/kg, 0.1 mg/kg, 0.3 mg/kg or 1 mg/kg.

FIG. 15 is a plot showing the percent change in blood glucose as a function of dose in ob/ob mice injected with vehicle (10 mM TRIS, 150 mM NaCl, pH 8.5) or different doses of a dually PEGylated E37C/R77C/P171G FGF21 mutant polypeptide over a nine day period. The results of this experiment demonstrate that the dually PEGylated triple mutant E37C/R77C/P171G reduced blood glucose levels in ob/ob mice in a dose-dependent manner. The dose level of 0.3 mg/kg nearly reached maximal glucose-lowering activity and the effects were maintained for at least 5 days. Further enhanced in vivo potency and duration of action were observed when the dose level increased to 1 mg/kg.

Example 12.B.2

Effect on Body Weight

Type 2 diabetes is often accompanied with increased adiposity and body weight. A therapeutic molecule would therefore preferably have the desirable effect of reducing body weight as well as the desirable effect of lowering blood glucose levels. Accordingly, many of the PEGylated FGF21 mutants described herein were evaluated for their effect on mice body weight.

To study the effect of various FGF21 mutant polypeptides on body weight, PEGylated wild-type and FGF21 mutant polypeptides were injected intraperitoneally into 8 week old ob/ob mice (Jackson Laboratory), and body weight was monitored at various time points following a single injection, e.g., 0, 24, 72, 120, and 168 hours after injection.

FIG. 16 shows the effect of the PEGylated FGF21 mutants on the weight of the mice over the term of the study. The results were generated using dually PEGylated E37C/R77C, E91C/R175C, E37C/H125C, E37C/R77C/P171 G, E91C/R175C/P171G, and E37C/H125C/P171G FGF21 mutant polypeptides. The FGF21 mutants were modified with 20 kDa methoxy PEG maleimide molecules in this study. These FGF21 mutants were also studied with respect to changes in glucose levels and those results are shown in FIG. 13. Taken together, this data demonstrates that the mice receiving the PEGylated FGF21 mutants gained less weight, relative to the vehicle control and that FGF21 mutant polypeptides comprising the proteolysis resistant mutation P171G are more efficacious than are their P171 wild-type counterparts.

Figure 17:
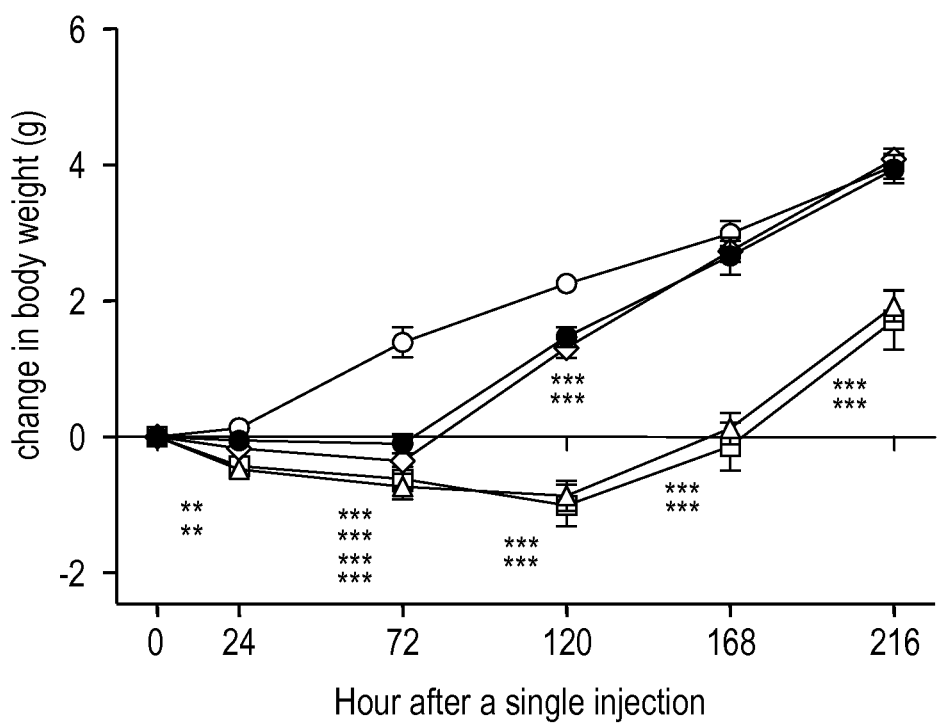
FIG. 17 is a plot showing body weight change in mice from time 0 after a single injection of vehicle (10 mM potassium phosphate, 5% sorbitol, pH 8), FGF21 mutant polypeptides which were dually PEGylated with 20 kDa methoxy PEG maleimide molecules at introduced polymer attachment sites, namely E37C/R77C/P171G and E91C/R125C/P171G, or Tethered Molecules comprising two FGF21 mutant polypeptides having the same introduced mutations, namely R37C/ P171G (2×) and R77C/P171G (2×), which were joined together via a 20 kDa methoxy PEG maleimide molecule.

FIG. 17 is plot showing the change in body weight of mice injected with vehicle, or the dually PEGylated forms of a FGF21 mutant comprising the mutations, namely E37C/R77C/P171 G; E91C/H125C/P171 G; R77C/P171G; and Tethered Molecules comprising in one case two E37C/P171G FGF21 mutant polypeptides and in another case two R77C/P171G FGF21 mutant polypeptides. 20 kDa methoxy PEG maleimide molecules were used in the PEGylated forms of FGF21, while 20 kDa PEG bis-maleimide was used for the Tethered Molecules. These FGF21 mutants were also studied with respect to changes in glucose levels and the results are shown in FIG. 14. Taken together, this data demonstrates that the mice receiving the PEGylated FGF21 mutants gained less weight, relative to the vehicle control. It was also observed that the dually PEGylated FGF21 mutant polypeptides were more efficacious in reducing body weight than the Tethered Molecules studied.

Figure 18:
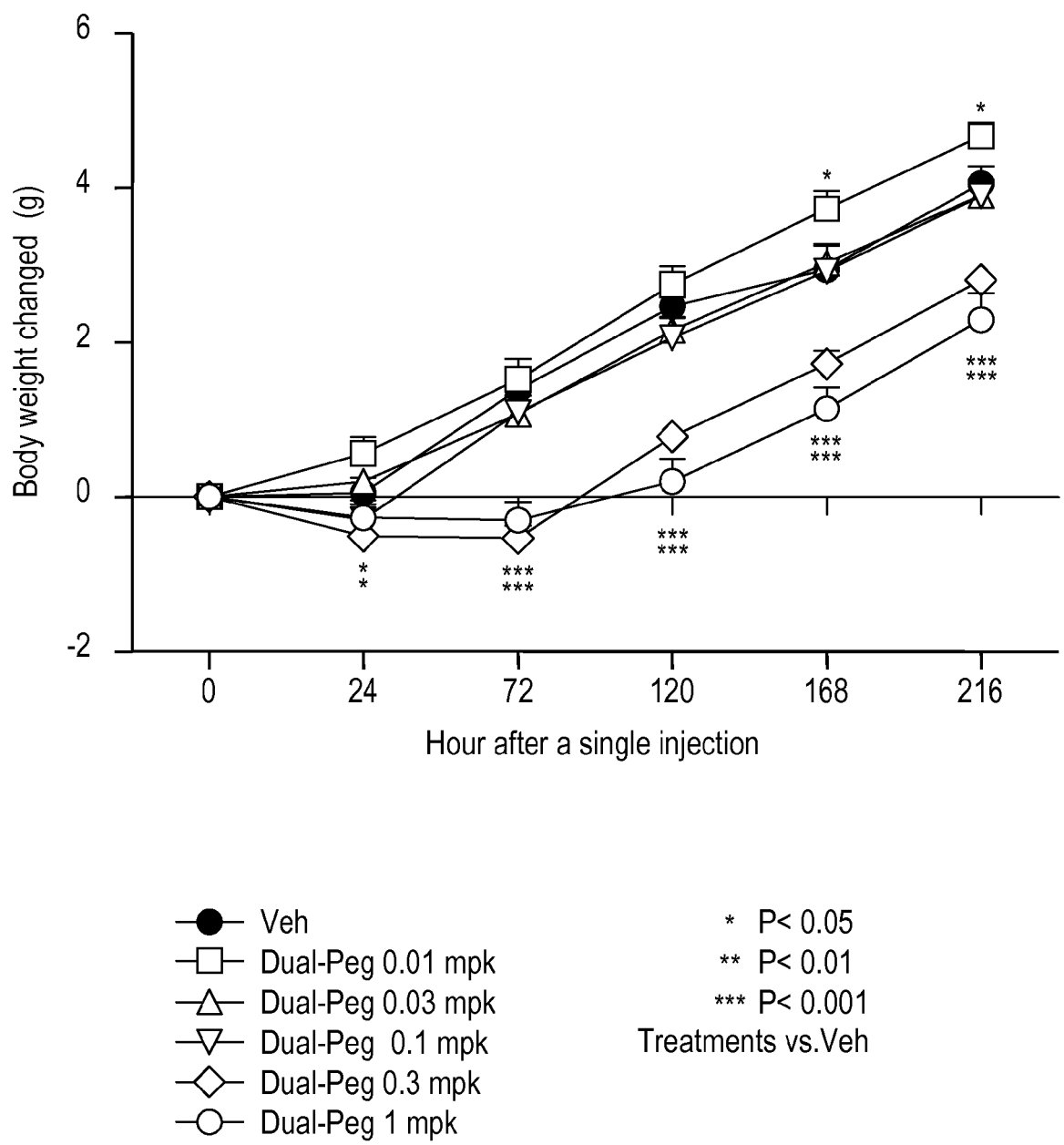
FIG. 18 is a plot showing body weight change in mice as a function of dose from time 0 after a single injection of vehicle (10 mM Tris HCl, 150 mM NaCl, pH 8.5), or an FGF21 mutant polypeptide which was dually PEGylated with 20 kDa methoxy PEG maleimide molecules at introduced polymer attachment sites, namely E37C/R77C/P171G, and administered at five different doses.

The effect of a dually PEGylated FGF21 mutant polypeptide on body weight was also examined in a multi-dose study. FIG. 18 is a plot showing the change in body weight as a function of dose in ob/ob mice injected with vehicle or different doses of dually PEGylated E37C/R77C/P171G over a nine day period. This FGF21 mutant was also studied with respect to changes in glucose levels and the results are shown in FIG. 15. Taken together, this data demonstrates that a dose level of 0.3 mg/kg is sufficient to reduce body weight gain in ob/ob mice after a single injection.

Example 13

Murine Kidney Vacuole Study

One consideration for employing PEG and other polymers to extend the half-life of a therapeutic protein is the possibility that the PEGylated molecule will form kidney vacuoles. This property of PEG is well-documented (see, e.g., Bendele, et al 1998, "Short Communication: Renal Tubular Vacuolation in Animals Treated with Polyethylene-glycol-conjugated Proteins," *Toxicological Sciences*, 42:152-157 and Conover et al., 1996, "Transitional Vacuole Formation Following a Bolus Infusion of PEG-hemoglobin in the Rat," *Art. Cells, Blood Subs., and Immob. Biotech.* 24:599-611) and can be unpredictable. A PEGylated molecule that induces the formation of kidney vacuoles typically, but not necessarily, renders the molecule less desirable as a therapeutic protein. In some circumstances kidney vacuolization is of less concern and can be tolerated. Accordingly, a long term kidney vacuole study was performed in mice.

FGF21 mutant polypeptides were generated as described herein. One study was designed and carried out as follows. Multiple PEGylated FGF21 molecules were administered once daily for 7 consecutive days via subcutaneous injection to female C57BL/6 mice (3/group) at a dose of 10 mg/kg; a vehicle control (10 mM $KHPO_4$, 150 mM NaCl, pH 8) and 2 positive controls were administered in the same manner. Detailed clinical observations were performed on all animals prior to each dose administration, and 1-2 hours post dose on days 1, 3, and 6; cage-side observations were collected 1-2 hours post dose on all other dosing days. Body weights were collected prior to each dose administration and at necropsy. The kidneys and liver were collected from all animals for histological evaluation. Table 15 summarizes the results of the study.

TABLE 15

Summary of Kidney Vacuole Study

| Molecule | Kidney | Liver |
|---|---|---|
| Vehicle | 0.0 | 0.0 |
| Positive Control | 3.7 | 0.0 |
| FGF21-1X-NT(PEG20K) | 2.0 | 0.0 |
| H126C 1X-PEG20K | 2.3 | 0.0 |
| R78C 1X-PEG20K | 2.3 | 0.0 |
| K70C 1X-PEG20K | 2.0 | 0.0 |
| G121C 1X-PEG20K | 2.0 | 0.0 |
| E38C 1X-PEG20K | 2.0 | 0.0 |
| R176C 1X-PEG20K | 3.0 | 0.0 |
| E92C 1X-PEG20K | 2.7 | 0.0 |
| N122C 1X-PEG20K | 2.0 | 0.0 |
| R127C 1X-PEG20K | 3.0 | 0.0 |
| G114C 1X-PEG20K | 2.7 | 0.0 |
| D80C 1X-PEG20K | 2.0 | 0.0 |
| D47C 1X-PEG20K | 3.0 | 0.0 |
| H112C 1X-PEG20K | 2.6 | 0.0 |
| K56R, K59R, K69R, K122R, R175K 2X-PEG20K | 0.0 | 0.0 |
| K56R, K59R, K69R, K122R, R77K 2X-PEG20K | 0.0 | 0.0 |
| K56R, K59R, K69R, K122R, R72K 2X-PEG20K | 0.0 | 0.0 |

Table 15 demonstrates the results of a 7-day murine vacuole study performed using vehicle (10 mM Tris, 150 mM NaCl, pH 8.5), N-terminally PEGylated form of FGF21, as well as PEGylated forms of FGF21 mutants comprising the mutations H125C, R77C, K69C, G120C, E37C, R175, E91C, N121C, R126C, G113C, D79C, D46C and H112C. Either one or two 20 kDa methoxy PEG maleimide molecules was used, as indicated in the table. The vacuole indices are a range with 0 being no observed change in vacuoles relative to control and 4 being severe vacuole formation. As is evident from Table 15, all of the mono-PEGylated FGF21 mutants induced the formation of kidney vacuoles. However, none of the dual-PEGylated FGF21 mutants induced vacuole formation. It was also noted that no vacuolization was observed in the livers of the mice.

Following the one week study, an 8 week chronic study was undertaken. In this study, various PEGylated FGF21 molecules were administered once weekly via subcutaneous injection for 8 weeks to female C57BL/6 mice (5/group) at doses of either 5 or 25 mg/kg; a vehicle control (10 mM Tris, 150 mM NaCl, pH 8.5) was administered in the same manner. All animals were observed for clinical signs once daily prior to dosing, and 1-2 hours post dose on dosing days; once daily on non-dosing days. Body weights were collected prior to each dose administration starting on Day 1 and then on the third day after each dose, and at necropsy. The kidneys, liver, and spleen were collected from all animals (moribund sacrifice and final euthanasia) for histological evaluation.

FIGS. 19A-19F is a series of plots showing weight change results observed during the eight week kidney vacuole study employing a vehicle (squares) and two doses of dual PEGylated, FGF21 mutants, namely 5 mg/kg (triangles) and 25 mg/kg (open circles). The FGF21 mutants studied include R77C, P171G (FIG. 19A); E37C, R77C, P171G (FIG. 19B); E37C, H125C, P171G (FIG. 19C); E91C, H125C, P171G (FIG. 19D); E37C, P171G (FIG. 19E) and R77C, P171G (FIG. 19F). In FIG. 19A, a mixed chemistry approach was employed, leading to N-terminal PEGylation of the FGF21 mutant as well as PEGylation at the introduced polymer attachment site, the non-naturally occurring cysteine at 77. In FIGS. 19B-19D, a single chemistry approach was employed, leading to PEGylation at the introduced polymer attachment sites, the non-naturally occurring cysteine residues (cysteines at positions 37 and 77 in FIG. 19B, positions 37 and 125 in FIG. 19C, and positions 91 and 125 in FIG. 19D). Finally, in FIGS. 19D and 19E, a single bis maleimide PEG was used to join two FGF21 mutants together at the non-naturally occurring cysteine residues (cysteine at position 37 in FIG. 21E and position 77 in FIG. 19F).

Figure 20:
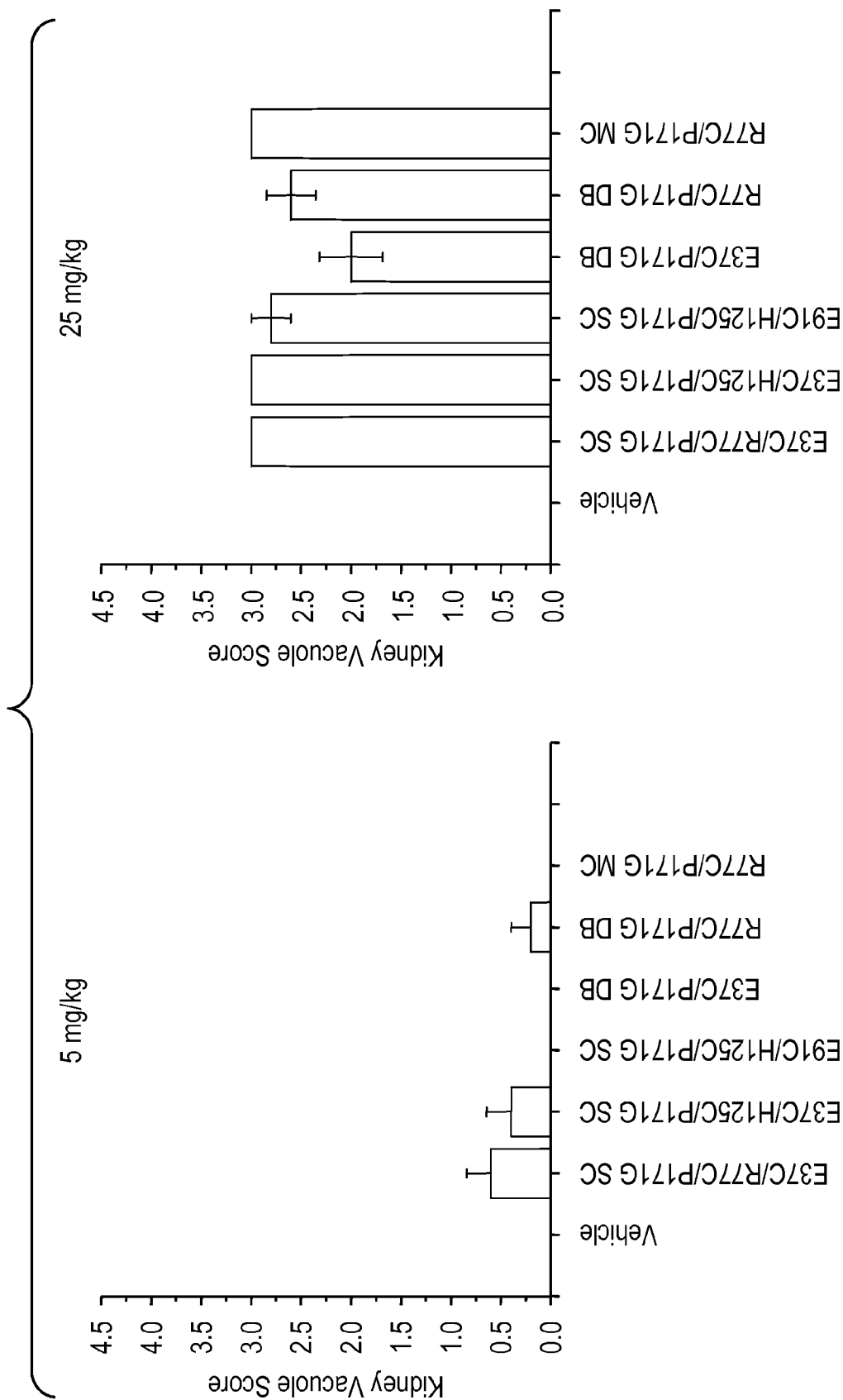
FIG. 20 comprises two bar graphs depicting the results of an eight week kidney vacuole study in mice injected with vehicle or an FGF21 mutant polypeptide which was dually PEGylated with 20 kDa methoxy PEG maleimide molecules at introduced polymer attachment sites, namely E37C/R77C/ P171G; E37/H125C/P171G; E91C/H125C/P171G; E37C/ P171G; R77C/P171G; and R77C/P171G; two different doses were tested.

FIG. 20 comprises two bar graphs showing the average score of kidney vacuoles observed during the eight-week kidney vacuole study for two doses, 5 and 25 mg/kg, of six singly or dually PEGylated FGF21 mutants. A score of 0 indicates no more vacuoles were observed than found in the control animals, while a score of 4 indicates severe vacuole formation relative to the control. The FGF21 mutants were the same as those described in FIG. 19A-19E. Thus, for one construct a mixed chemistry approach was employed, leading to N-terminal PEGylation of the FGF21 mutant as well as PEGylation at the introduced polymer attachment site, the non-naturally occurring cysteine at 77. A single chemistry approach was employed for three other constructs, leading to PEGylation at the introduced polymer attachment sites, the non-naturally occurring cysteine residues (cysteines at positions 37 and 77 in one construct, positions 37 and 125 in a second construct or positions 91 and 125 in a third construct). Finally, a single bis maleimide PEG was used to join two FGF21 mutants together at the non-naturally occurring cysteine residues (cysteine at position 37 or position 77). The P171G mutation was introduced into each of the six constructs.

While the present invention has been described in terms of various embodiments, it is understood that variations and modifications will occur to those skilled in the art. Therefore, it is intended that the appended claims cover all such equivalent variations that come within the scope of the invention as claimed. In addition, the section headings used herein are for organizational purposes only and are not to be construed as limiting the subject matter described.

All references cited in this disclosure are expressly incorporated by reference herein.

---

What is claimed is:

1. An isolated nucleic acid molecule comprising a nucleotide sequence encoding a polypeptide of SEQ ID NO: 4 having a lysine residue substitution at position 36 and at least one amino acid substitution that is: an arginine residue substitution at position 56, 59, 69, or 122; and wherein the isolated polypeptide comprises no more than five amino acid substitutions.

2. A vector comprising the nucleic acid molecule of claim 1.

3. A host cell comprising the vector of claim 2.

4. The host cell of claim 3 that is a eukaryotic cell.

5. The host cell of claim 3 that is a prokaryotic cell.

6. A process of producing a polypeptide encoded by the vector of claim 2 comprising culturing a host cell comprising the vector of claim 2 under suitable conditions to express the polypeptide, and optionally isolating the polypeptide.

7. A polypeptide produced by the process of claim 6.

8. The polypeptide of claim 7, further comprising a proline or glycine residue added to the C-terminus of the polypeptide.

9. The isolated polypeptide of claim 7, wherein the polypeptide is covalently linked to one or more polymers.

10. The isolated polypeptide of claim 9, wherein the polypeptide is covalently linked to one polymer.

11. The isolated polypeptide of claim 10, wherein the polymer is a water-soluble polymer.

12. The isolated polypeptide of claim 11, wherein the water-soluble polymer is polyethylene glycol (PEG), monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, or polyvinyl alcohol.

13. The isolated polypeptide of claim 12, wherein the water-soluble polymer is PEG.

14. The isolated polypeptide of claim 9, wherein the polymer is a branched polymer.

15. The isolated polypeptide of claim 8, wherein the polypeptide has a PEG moiety covalently linked to its amino-terminus.

16. The isolated polypeptide of claim 8, wherein the polypeptide is covalently linked to two polymers.

17. The isolated polypeptide of claim 16, wherein one of the two polymers is a water-soluble polymer.

18. The isolated polypeptide of claim 17, wherein the water-soluble polymer is polyethylene glycol (PEG), monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, or polyvinyl alcohol.

19. The isolated polypeptide of claim 18, wherein the water-soluble polymer is PEG.

20. The isolated polypeptide of claim 16, wherein one of the polymers is branched.

21. The isolated polypeptide of claim 16, wherein both of the polymers are branched.

22. The isolated polypeptide of claim 8, wherein the polypeptide has a PEG moiety covalently linked to its amino-terminus.

23. A pharmaceutical composition comprising the isolated polypeptide of claim 8 and a pharmaceutically acceptable formulation agent.

24. The pharmaceutical composition of claim 23, wherein the pharmaceutically acceptable formulation agent is a carrier, adjuvant, solubilizer, stabilizer, or anti-oxidant.

25. A method for lowering blood glucose levels, lowering insulin levels, lowering triglyceride levels, lowering cholesterol levels, or reducing body weight comprising administering to a human in need thereof the pharmaceutical composition of claim 24.

26. The method of claim 25, wherein the human has diabetes.

27. The method of claim 25, wherein the human has obesity.

28. A composition comprising a first polypeptide comprising the amino acid sequence of SEQ ID NO: 4 having a lysine residue substitution at position 36 and having at least one amino acid substitution that is: an arginine residue substitution at position 56, 59, 69, or 122; and wherein the isolated polypeptide comprises no more than five amino acid substitutions, and wherein the isolated polypeptide is joined by a linker to a second polypeptide comprising the amino acid sequence of SEQ ID NO: 4 having a lysine residue substitution at position 36 and having at least one amino acid substitution that is an arginine residue substitution at position 56, 59, 69, or 122; and wherein the second polypeptide-comprises no more than five amino acid substitutions.

29. The polypeptide of claim 28, wherein the first, second or both polypeptides further comprise a proline or glycine residue added to the C-terminus of the polypeptide.

30. The composition of claim 28, wherein the linker is a peptide.

31. The composition of claim 28, wherein the linker is a water insoluble polymer.

32. The composition of claim 31, wherein the water-soluble polymer is polyethylene glycol (PEG), monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, or polyvinyl alcohol.

33. The composition of claim 32, wherein the water-soluble polymer is PEG.

34. The composition of claim 28, wherein the first, second or both polypeptides are further covalently linked to one polymer, in addition to the linker.

35. The composition of claim 34, wherein the polymer is a water-soluble polymer.

36. The composition of claim 35, wherein the water-soluble polymer is polyethylene glycol (PEG), monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, or polyvinyl alcohol.

37. The composition of claim 36, wherein the water-soluble polymer is PEG.

38. The composition of claim 31, wherein the polymer is branched.

39. The composition of claim 28, wherein the composition has a single PEG moiety covalently linked to its amino-terminus.

40. The composition of claim 28, wherein the composition is covalently linked to two polymers.

41. The composition of claim 40, wherein one if the two polymers is a water-soluble polymer.

42. The composition of claim 41, wherein the water-soluble polymer is polyethylene glycol (PEG), monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, or polyvinyl alcohol.

43. The composition of claim 42, wherein the water-soluble polymer is PEG.

44. The composition of claim 40, wherein both of the polymers are water soluble polymers.

45. The composition of claim 44, wherein the water-soluble polymers are independently polyethylene glycol (PEG), monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, or polyvinyl alcohol and combinations thereof.

46. The composition of claim 45, wherein both of the water soluble polymers are PEG.

47. The isolated polypeptide of claim 40, wherein one of the polymers is branched.

48. The isolated polypeptide of claim 40, wherein both of the polymers are branched.

49. A pharmaceutical composition comprising the composition of claim 28 and a pharmaceutically acceptable formulation agent.

50. The pharmaceutical composition of claim 49, wherein the pharmaceutically acceptable formulation agent is a carrier, adjuvant, solubilizer, stabilizer, or anti-oxidant.

51. A method for lowering blood glucose levels, lowering insulin levels, lowering triglyceride levels, lowering cholesterol levels, or reducing body weight comprising administering to a human in need thereof the pharmaceutical composition of claim 49.

52. The method of claim 51, wherein the human has diabetes.

53. The method of claim 51, wherein the human has obesity.

* * * * *

SEQUENCE LISTING

```
<160> NUMBER OF SEQ ID NOS: 34

<210> SEQ ID NO 1
<211> LENGTH: 630
<212> TYPE: DNA
<213> ORGANISM: Homo sapiens

<400> SEQUENCE: 1
atggactcgg acgagaccgg gttcgagcac tcaggactgt gggtttctgt gctggctggt      60
cttctgctgg gagcctgcca ggcacacccc atccctgact ccagtcctct cctgcaattc     120
gggggccaag tccggcagcg gtacctctac acagatgatg cccagcagac agaagcccac     180
ctggagatca gggaggatgg gacggtgggg ggcgctgctg accagagccc cgaaagtctc     240
ctgcagctga aagccttgaa gccgggagtt attcaaatct gggagtcaa gacatccagg      300 ttcctgtgcc agcggccaga tggggccctg tatggatcgc tccactttga ccctgaggcc     360
tgcagcttcc gggagctgct tcttgaggac ggatacaatg tttaccagtc cgaagcccac     420
ggcctcccgc tgcacctgcc agggaacaag tccccacacc gggaccctgc accccgagga     480
ccagctcgct tcctgccact accaggcctg ccccccgcac ccccggagcc acccggaatc     540
ctggcccccc agcccccga tgtgggctcc tcggaccctc tgagcatggt gggaccttcc      600
cagggccgaa gccccagcta cgcttcctga                                      630

<210> SEQ ID NO 2
<211> LENGTH: 209
<212> TYPE: PRT
<213> ORGANISM: Homo sapiens

<400> SEQUENCE: 2

Met Asp Ser Asp Glu Thr Gly Phe Glu His Ser Gly Leu Trp Val Ser
1               5                   10                  15
```

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 3
<211> LENGTH: 546
<212> TYPE: DNA
<213> ORGANISM: Homo sapiens

<400> SEQUENCE: 3
caccccatcc ctgactccag tcctctcctg caattcgggg gccaagtccg gcagcggtac      60
ctctacacag atgatgccca gcagacagaa gcccacctgg agatcaggga ggatgggacg     120 gtgggggggcg ctgctgacca gagccccgaa agtctcctgc agctgaaagc cttgaagccg     180
ggagttattc aaatcttggg agtcaagaca tccaggttcc tgtgccagcg gccagatggg     240
gccctgtatg gatcgctcca ctttgaccct gaggcctgca gcttccggga gctgcttctt     300
gaggacggat acaatgttta ccagtccgaa gcccacggcc tcccgctgca cctgccaggg     360
aacaagtccc cacaccggga ccctgcaccc cgaggaccag ctcgcttcct gccactacca     420
ggcctgcccc ccgcaccccc ggagccaccg gaatcctggg cccccagcc ccccgatgtg      480 ggctcctcgg accctctgag catggtggga ccttcccagg ccgaagccc agctacgct      540 tcctga                                                                546

<210> SEQ ID NO 4
<211> LENGTH: 181
<212> TYPE: PRT
<213> ORGANISM: Homo sapiens

<400> SEQUENCE: 4

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His

```
                    20                  25                  30
Leu Glu Ile Arg Glu Asp Gly Thr Val Gly Ala Ala Asp Gln Ser
             35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 5
<211> LENGTH: 6
<212> TYPE: PRT
<213> ORGANISM: ARTIFICIAL SEQUENCE
<220> FEATURE:
<223> OTHER INFORMATION: Linker Sequence
<220> FEATURE:
<221> NAME/KEY: MISC_FEATURE
<222> LOCATION: (1)..(2)
<223> OTHER INFORMATION: X IS INDEPENDENTLY ANY AMINO ACID RESIDUE
<220> FEATURE:
<221> NAME/KEY: MISC_FEATURE
<222> LOCATION: (4)..(5)
<223> OTHER INFORMATION: X IS INDEPENDENTLY ANY AMINO ACID RESIDUE

<400> SEQUENCE: 5

Xaa Xaa Asn Xaa Xaa Gly
 1               5

<210> SEQ ID NO 6
<211> LENGTH: 4
<212> TYPE: PRT
<213> ORGANISM: ARTIFICIAL SEQUENCE
<220> FEATURE:
<223> OTHER INFORMATION: Linker Sequence

<400> SEQUENCE: 6

Gly Gly Gly Gly
 1

<210> SEQ ID NO 7
<211> LENGTH: 5
<212> TYPE: PRT
<213> ORGANISM: ARTIFICIAL SEQUENCE
<220> FEATURE:
<223> OTHER INFORMATION: Linker Sequence

<400> SEQUENCE: 7

Gly Gly Gly Gly Gly
 1               5
```

```
<210> SEQ ID NO 8
<211> LENGTH: 5
<212> TYPE: PRT
<213> ORGANISM: ARTIFICIAL SEQUENCE
<220> FEATURE:
<223> OTHER INFORMATION: Linker Sequence

<400> SEQUENCE: 8

Gly Gly Gly Gly Ser
1               5

<210> SEQ ID NO 9
<211> LENGTH: 10
<212> TYPE: PRT
<213> ORGANISM: ARTIFICIAL SEQUENCE
<220> FEATURE:
<223> OTHER INFORMATION: Linker Sequence

<400> SEQUENCE: 9

Gly Gly Gly Gly Ser Gly Gly Gly Gly Ser
1               5                   10

<210> SEQ ID NO 10
<211> LENGTH: 25
<212> TYPE: PRT
<213> ORGANISM: ARTIFICIAL SEQUENCE
<220> FEATURE:
<223> OTHER INFORMATION: Linker Sequence

<400> SEQUENCE: 10

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 11
<211> LENGTH: 6
<212> TYPE: PRT
<213> ORGANISM: ARTIFICIAL SEQUENCE
<220> FEATURE:
<223> OTHER INFORMATION: Linker Sequence

<400> SEQUENCE: 11

Gly Gly Glu Gly Gly Gly
1               5

<210> SEQ ID NO 12
<211> LENGTH: 8
<212> TYPE: PRT
<213> ORGANISM: ARTIFICIAL SEQUENCE
<220> FEATURE:
<223> OTHER INFORMATION: Linker Sequence

<400> SEQUENCE: 12

Gly Gly Glu Glu Glu Gly Gly Gly
1               5

<210> SEQ ID NO 13
<211> LENGTH: 5
<212> TYPE: PRT
<213> ORGANISM: ARTIFICIAL SEQUENCE
<220> FEATURE:
<223> OTHER INFORMATION: Linker Sequence

<400> SEQUENCE: 13

Gly Glu Glu Glu Gly
```

```
1               5

<210> SEQ ID NO 14
<211> LENGTH: 4
<212> TYPE: PRT
<213> ORGANISM: ARTIFICIAL SEQUENCE
<220> FEATURE:
<223> OTHER INFORMATION: Linker Sequence

<400> SEQUENCE: 14

Gly Glu Glu Glu
1

<210> SEQ ID NO 15
<211> LENGTH: 6
<212> TYPE: PRT
<213> ORGANISM: ARTIFICIAL SEQUENCE
<220> FEATURE:
<223> OTHER INFORMATION: Linker Sequence

<400> SEQUENCE: 15

Gly Gly Asp Gly Gly Gly
1               5

<210> SEQ ID NO 16
<211> LENGTH: 7
<212> TYPE: PRT
<213> ORGANISM: ARTIFICIAL SEQUENCE
<220> FEATURE:
<223> OTHER INFORMATION: Linker Sequence

<400> SEQUENCE: 16

Gly Gly Asp Asp Asp Gly Gly
1               5

<210> SEQ ID NO 17
<211> LENGTH: 5
<212> TYPE: PRT
<213> ORGANISM: ARTIFICIAL SEQUENCE
<220> FEATURE:
<223> OTHER INFORMATION: Linker Sequence

<400> SEQUENCE: 17

Gly Asp Asp Asp Gly
1               5

<210> SEQ ID NO 18
<211> LENGTH: 4
<212> TYPE: PRT
<213> ORGANISM: ARTIFICIAL SEQUENCE
<220> FEATURE:
<223> OTHER INFORMATION: Linker Sequence

<400> SEQUENCE: 18

Gly Asp Asp Asp
1

<210> SEQ ID NO 19
<211> LENGTH: 21
<212> TYPE: PRT
<213> ORGANISM: ARTIFICIAL SEQUENCE
<220> FEATURE:
<223> OTHER INFORMATION: Linker Sequence

<400> SEQUENCE: 19

Gly Gly Gly Gly Ser Asp Asp Ser Asp Glu Gly Ser Asp Gly Glu Asp
1               5                   10                  15
```

```
Gly Gly Gly Gly Ser
            20

<210> SEQ ID NO 20
<211> LENGTH: 5
<212> TYPE: PRT
<213> ORGANISM: ARTIFICIAL SEQUENCE
<220> FEATURE:
<223> OTHER INFORMATION: Linker Sequence

<400> SEQUENCE: 20

Trp Glu Trp Glu Trp
1               5

<210> SEQ ID NO 21
<211> LENGTH: 5
<212> TYPE: PRT
<213> ORGANISM: ARTIFICIAL SEQUENCE
<220> FEATURE:
<223> OTHER INFORMATION: Linker Sequence

<400> SEQUENCE: 21

Phe Glu Phe Glu Phe
1               5

<210> SEQ ID NO 22
<211> LENGTH: 6
<212> TYPE: PRT
<213> ORGANISM: ARTIFICIAL SEQUENCE
<220> FEATURE:
<223> OTHER INFORMATION: Linker Sequence

<400> SEQUENCE: 22

Glu Glu Glu Trp Trp Trp
1               5

<210> SEQ ID NO 23
<211> LENGTH: 6
<212> TYPE: PRT
<213> ORGANISM: ARTIFICIAL SEQUENCE
<220> FEATURE:
<223> OTHER INFORMATION: Linker Sequence

<400> SEQUENCE: 23

Glu Glu Glu Phe Phe Phe
1               5

<210> SEQ ID NO 24
<211> LENGTH: 7
<212> TYPE: PRT
<213> ORGANISM: ARTIFICIAL SEQUENCE
<220> FEATURE:
<223> OTHER INFORMATION: Linker Sequence

<400> SEQUENCE: 24

Trp Trp Glu Glu Glu Trp Trp
1               5

<210> SEQ ID NO 25
<211> LENGTH: 7
<212> TYPE: PRT
<213> ORGANISM: ARTIFICIAL SEQUENCE
<220> FEATURE:
<223> OTHER INFORMATION: Linker Sequence

<400> SEQUENCE: 25
```

Phe Phe Glu Glu Glu Phe Phe
1               5

<210> SEQ ID NO 26
<211> LENGTH: 6
<212> TYPE: PRT
<213> ORGANISM: ARTIFICIAL SEQUENCE
<220> FEATURE:
<223> OTHER INFORMATION: Linker Sequence
<220> FEATURE:
<221> NAME/KEY: MISC_FEATURE
<222> LOCATION: (1)..(2)
<223> OTHER INFORMATION: X IS INDEPENDENTLY ANY AMINO ACID RESIDUE
<220> FEATURE:
<221> NAME/KEY: MISC_FEATURE
<222> LOCATION: (4)..(5)
<223> OTHER INFORMATION: X IS INDEPENDENTLY ANY AMINO ACID RESIDUE

<400> SEQUENCE: 26

Xaa Xaa Tyr Xaa Xaa Gly
1               5

<210> SEQ ID NO 27
<211> LENGTH: 6
<212> TYPE: PRT
<213> ORGANISM: ARTIFICIAL SEQUENCE
<220> FEATURE:
<223> OTHER INFORMATION: Linker Sequence
<220> FEATURE:
<221> NAME/KEY: MISC_FEATURE
<222> LOCATION: (1)..(2)
<223> OTHER INFORMATION: X IS INDEPENDENTLY ANY AMINO ACID RESIDUE
<220> FEATURE:
<221> NAME/KEY: MISC_FEATURE
<222> LOCATION: (4)..(5)
<223> OTHER INFORMATION: X IS INDEPENDENTLY ANY AMINO ACID RESIDUE

<400> SEQUENCE: 27

Xaa Xaa Ser Xaa Xaa Gly
1               5

<210> SEQ ID NO 28
<211> LENGTH: 6
<212> TYPE: PRT
<213> ORGANISM: ARTIFICIAL SEQUENCE
<220> FEATURE:
<223> OTHER INFORMATION: Linker Sequence
<220> FEATURE:
<221> NAME/KEY: MISC_FEATURE
<222> LOCATION: (1)..(2)
<223> OTHER INFORMATION: X IS INDEPENDENTLY ANY AMINO ACID RESIDUE
<220> FEATURE:
<221> NAME/KEY: MISC_FEATURE
<222> LOCATION: (4)..(5)
<223> OTHER INFORMATION: X IS INDEPENDENTLY ANY AMINO ACID RESIDUE

<400> SEQUENCE: 28

Xaa Xaa Thr Xaa Xaa Gly
1               5

<210> SEQ ID NO 29
<211> LENGTH: 27
<212> TYPE: DNA
<213> ORGANISM: ARTIFICIAL SEQUENCE
<220> FEATURE:
<223> OTHER INFORMATION: Primer Sequence

<400> SEQUENCE: 29
atggtggaac cttcccaggg ccgaagc                                      27

```
<210> SEQ ID NO 30
<211> LENGTH: 50
<212> TYPE: DNA
<213> ORGANISM: ARTIFICIAL SEQUENCE
<220> FEATURE:
<223> OTHER INFORMATION: Primer Sequence

<400> SEQUENCE: 30
ctcctcggac cctctgagca tggtgggacc ttcccagggc cgaagcccca          50

<210> SEQ ID NO 31
<211> LENGTH: 50
<212> TYPE: DNA
<213> ORGANISM: ARTIFICIAL SEQUENCE
<220> FEATURE:
<223> OTHER INFORMATION: Primer Sequence

<400> SEQUENCE: 31
gaggagcctg ggagactcgt accaccctgg aagggtcccg gcttcggggt          50

<210> SEQ ID NO 32
<211> LENGTH: 30
<212> TYPE: DNA
<213> ORGANISM: ARTIFICIAL SEQUENCE
<220> FEATURE:
<223> OTHER INFORMATION: Primer Sequence

<400> SEQUENCE: 32
ggaaggttcc accatgctca gagggtccga                                30

<210> SEQ ID NO 33
<211> LENGTH: 40
<212> TYPE: DNA
<213> ORGANISM: ARTIFICIAL SEQUENCE
<220> FEATURE:
<223> OTHER INFORMATION: Primer Sequence

<400> SEQUENCE: 33
aggaggaata acatatgcat ccaattccag attcttctcc                     40

<210> SEQ ID NO 34
<211> LENGTH: 33
<212> TYPE: DNA
<213> ORGANISM: ARTIFICIAL SEQUENCE
<220> FEATURE:
<223> OTHER INFORMATION: Primer Sequence

<400> SEQUENCE: 34
tagtgagctc gaattcttag gaagcgtagc tgg                            33
```